(12) United States Patent
Brezoczky et al.

(10) Patent No.: US 9,278,034 B2
(45) Date of Patent: Mar. 8, 2016

(54) DEVICES AND METHODS FOR TREATING ACCIDENTAL BOWEL LEAKAGE

(71) Applicant: Butterfly Health, Inc., Los Gatos, CA (US)

(72) Inventors: Thomas Blasius Brezoczky, Los Gatos, CA (US); Karl Patrick Ronn, Palo Alto, CA (US); Kelly Lewis Brezoczky, Los Gatos, CA (US); Elizabeth Hodge Ronn, Palo Alto, CA (US); Steven B. Gold, Longboat Key, FL (US)

(73) Assignee: Butterfly Health, Inc., Los Gatos, CA (US)

( * ) Notice: Subject to any disclaimer, the term of this patent is extended or adjusted under 35 U.S.C. 154(b) by 111 days.

(21) Appl. No.: 13/754,809

(22) Filed: Jan. 30, 2013

(65) Prior Publication Data

US 2013/0197459 A1     Aug. 1, 2013

Related U.S. Application Data

(63) Continuation-in-part of application No. 29/422,461, filed on May 21, 2012, and a continuation-in-part of application No. 29/437,530, filed on Nov. 16, 2012.

(60) Provisional application No. 61/593,052, filed on Jan. 31, 2012, provisional application No. 61/649,749, filed on May 21, 2012.

(51) Int. Cl.
*A61F 13/47*     (2006.01)
*A61F 13/537*    (2006.01)
*A61F 13/56*     (2006.01)
(Continued)

(52) U.S. Cl.
CPC ......... *A61F 13/4704* (2013.01); *A61F 13/2011* (2013.01); *A61F 13/537* (2013.01); *A61F 13/5605* (2013.01); *A61F 13/82* (2013.01); *A61F 2013/1513* (2013.01)

(58) Field of Classification Search
CPC .................... A61F 13/4704; A61F 2013/1513; A61F 2013/15121; A61F 2013/4706
See application file for complete search history.

(56) References Cited

U.S. PATENT DOCUMENTS

| 1,897,952 | A | 2/1933 | Dupont |
| 2,064,431 | A | 12/1936 | Jurgensen |

(Continued)

FOREIGN PATENT DOCUMENTS

| EP | 1025823 A1 | 8/2000 |
| JP | 10-511280 A | 11/1998 |

(Continued)

OTHER PUBLICATIONS

International Search Report and Written Opinion received for PCT Patent Application No. PCT/US2013/023928 mailed on May 10, 2013, 11 pages.

(Continued)

*Primary Examiner* — Susan Su
(74) *Attorney, Agent, or Firm* — Morrison & Foerster LLP

(57) ABSTRACT

Described here are body liners and methods for treating accidental bowel leakage using one or more body liners. The body liners may be formed from one or more liner layers and in some instances may comprise one or more adhesive regions to connect the body liners to the skin of a wearer. The body liners may be configured to absorb fluid, and may selectively distribute fluid relative to the body liner.

17 Claims, 19 Drawing Sheets

(51) Int. Cl.
  *A61F 13/82* (2006.01)
  *A61F 13/20* (2006.01)
  *A61F 13/15* (2006.01)

(56) References Cited

U.S. PATENT DOCUMENTS

| | | | |
|---|---|---|---|
| 2,742,042 | A | 4/1956 | Flanders |
| 4,182,335 | A | 1/1980 | Matrullo |
| 4,484,919 | A | 11/1984 | Sohn et al. |
| 4,605,404 | A | 8/1986 | Sneider |
| 4,747,162 | A | 5/1988 | Yanagihara |
| 5,042,088 | A | 8/1991 | Sherrod et al. |
| H001511 | H | 12/1995 | Chappell et al. |
| 5,509,913 | A | 4/1996 | Yeo |
| 5,514,104 | A | 5/1996 | Cole et al. |
| 5,556,392 | A | 9/1996 | Koczab |
| 5,658,270 | A | 8/1997 | Lichstein |
| 5,695,484 | A | 12/1997 | Cox |
| 5,797,894 | A | 8/1998 | Cadieux et al. |
| 5,833,677 | A | 11/1998 | Sauer |
| 5,884,330 | A | 3/1999 | Erlich |
| 6,107,539 | A | 8/2000 | Palumbo et al. |
| 6,160,197 | A | 12/2000 | Lassen et al. |
| 6,254,584 | B1 | 7/2001 | Osborn, III et al. |
| 6,258,427 | B1 | 7/2001 | Kerins et al. |
| 6,313,371 | B1 | 11/2001 | Conant et al. |
| 6,406,464 | B1 | 6/2002 | Palumbo et al. |
| 6,409,714 | B2 | 6/2002 | Osborn, III et al. |
| 6,423,046 | B1 | 7/2002 | Fujioka et al. |
| 6,440,114 | B1 | 8/2002 | Bast et al. |
| 6,461,341 | B1 | 10/2002 | Bennett |
| 6,494,871 | B1 | 12/2002 | Lariviere et al. |
| D468,425 | S | 1/2003 | Edens et al. |
| 6,515,195 | B1 | 2/2003 | Lariviere et al. |
| 6,530,910 | B1 | 3/2003 | Pomplun et al. |
| D476,736 | S | 7/2003 | Hantke et al. |
| 6,592,892 | B1 | 7/2003 | Williams |
| 6,613,031 | B2 | 9/2003 | Glasgow et al. |
| 6,613,955 | B1 | 9/2003 | Lindsay et al. |
| 6,652,502 | B2 | 11/2003 | Bast et al. |
| 6,681,407 | B2 | 1/2004 | Martz |
| 6,709,423 | B1 | 3/2004 | Herrlein et al. |
| 6,716,203 | B2 | 4/2004 | Sorebo et al. |
| 6,890,325 | B2 | 5/2005 | Edens et al. |
| 6,929,628 | B2 | 8/2005 | George |
| 7,033,342 | B2 | 4/2006 | Mizutani et al. |
| 7,195,619 | B2 | 3/2007 | Manasek |
| 7,534,236 | B2 | 5/2009 | Mizutani et al. |
| 7,566,329 | B2 | 7/2009 | Rosenfeld et al. |
| 7,626,073 | B2 | 12/2009 | Catalan |
| 7,744,932 | B2 | 6/2010 | Faller et al. |
| 7,918,837 | B2 | 4/2011 | Rosenfeld |
| 7,928,279 | B2 | 4/2011 | Rosenberg |
| 7,941,872 | B2 | 5/2011 | Martz |
| 8,012,137 | B2 | 9/2011 | Lira et al. |
| 8,042,194 | B2 | 10/2011 | Connor |
| 8,062,275 | B2 | 11/2011 | Plentovich et al. |
| 8,062,277 | B2 | 11/2011 | Fleming |
| 8,084,063 | B2 | 12/2011 | Faller et al. |
| 8,084,066 | B2 | 12/2011 | Faller et al. |
| 8,157,779 | B2 | 4/2012 | Williams |
| 8,314,285 | B2 | 11/2012 | Veglio et al. |
| 8,591,488 | B2 | 11/2013 | Brezoczky et al. |
| 8,821,466 | B2 | 9/2014 | Brezoczky et al. |
| 8,979,814 | B2 | 3/2015 | Brezoczky et al. |
| 9,095,476 | B2 | 8/2015 | Brezoczky et al. |
| 2001/0027304 | A1* | 10/2001 | Mayer ............... 604/385.14 |
| 2002/0042599 | A1 | 4/2002 | Zhao et al. |
| 2002/0082580 | A1 | 6/2002 | Bennett |
| 2002/0188269 | A1* | 12/2002 | Edens et al. ......... 604/385.17 |
| 2003/0208170 | A1 | 11/2003 | D'Acchioli et al. |
| 2003/0216704 | A1 | 11/2003 | George |
| 2003/0233701 | A1 | 12/2003 | Martz |
| 2004/0068247 | A1* | 4/2004 | Connor ................ 604/387 |
| 2004/0162537 | A1 | 8/2004 | Manasek |
| 2004/0167479 | A1 | 8/2004 | Warren et al. |
| 2005/0182376 | A1 | 8/2005 | Fleming |
| 2005/0192549 | A1 | 9/2005 | Veglio et al. |
| 2005/0222548 | A1 | 10/2005 | Cinelli et al. |
| 2006/0142726 | A1 | 6/2006 | Tokumoto et al. |
| 2006/0200108 | A1 | 9/2006 | Mizutani et al. |
| 2006/0224133 | A1 | 10/2006 | Gannon et al. |
| 2006/0253092 | A1 | 11/2006 | Ponomarenko et al. |
| 2007/0135788 | A1* | 6/2007 | Damay et al. ........... 604/385.01 |
| 2009/0093784 | A1 | 4/2009 | Hansen et al. |
| 2009/0182296 | A1 | 7/2009 | Dennis et al. |
| 2009/0198203 | A1 | 8/2009 | Lira et al. |
| 2009/0204092 | A1 | 8/2009 | Loyd et al. |
| 2010/0057034 | A1 | 3/2010 | Dennis et al. |
| 2010/0152687 | A1 | 6/2010 | Carlozzi |
| 2010/0152693 | A1 | 6/2010 | Lira et al. |
| 2010/0168693 | A1 | 7/2010 | Edvardsen et al. |
| 2011/0092935 | A1 | 4/2011 | Hann et al. |
| 2011/0220128 | A1* | 9/2011 | Steinberg ............... 128/887 |
| 2012/0215195 | A1 | 8/2012 | Lira et al. |
| 2014/0088536 | A1 | 3/2014 | Brezoczky et al. |

FOREIGN PATENT DOCUMENTS

| | | |
|---|---|---|
| JP | 2002-540893 A | 12/2002 |
| JP | 2011-115516 A | 6/2011 |
| WO | 96/19169 A1 | 6/1996 |
| WO | 00/61039 A1 | 10/2000 |
| WO | 02/13877 A2 | 2/2002 |
| WO | 2007/134600 A1 | 11/2007 |
| WO | 2010/113398 A1 | 10/2010 |

OTHER PUBLICATIONS

B-SURE, "B-SURE Absorbent Pads", Birchwood Laboratories, Inc., 2012, 1 page.
Brezoczky et al., U.S. Appl. No. 13/754,787, filed Jan. 30, 2013, titled "Device and Methods for Treating Accidental Bowel Leakage", 100 pages.
Non Final Office Action received for U.S. Appl. No. 14/089,578, mailed on Mar. 11, 2014, 7 pages.
Non Final Office Action received for U.S. Appl. No. 14/089,606, mailed on Feb. 21, 2014, 12 pages.
Non Final Office Action received for U.S. Appl. No. 13/754,787, mailed on Jul. 25, 2013, 12 pages.
Notice of Allowance received for U.S. Appl. No. 13/754,787, mailed on Sep. 17, 2013, 8 pages.
Notice of Allowance received for U.S. Appl. No. 14/089,578, mailed on Apr. 23, 2014, 7 pages.
Notice of Allowance received for U.S. Appl. No. 14/089,606, mailed on Sep. 25, 2014, 8 pages.
Notice of Allowance received for U.S. Appl. No. 14/089,606, mailed on Feb. 17, 2015, 5 pages.
Non-Final Office Action received for U.S. Appl. No. 14/446,244, mailed on Dec. 1, 2014, 6 pages.
Office Action Received for Mexican Patent Application No. MX/a/2014/009181, mailed on Oct. 17, 2014, 1 page of Official Copy only (See Communication under 37 CFR § 1.98(a) (3)).
International Preliminary Report on Patentability received for PCT Patent Application No. PCT/US2013/023928, mailed on Dec. 18, 2014, 8 pages.
Extended European Search Report (includes Supplementary European Search Report and Search Opinion) received for European Patent Application No. 13744056.6, mailed on Jun. 29, 2015, 7 pages.
Notice of Allowance received for U.S. Appl. No. 14/446,244, mailed on Mar. 30, 2015, 5 pages.
Office Action received for Australian Patent Application No. 2013204189 mailed on Oct. 14, 2014, 3 pages.
Notice of Acceptance Received for African Patent Application No. 201405624, mailed on Aug. 12, 2015, 1 page.
Office Action received for Japanese Patent Application No. 2014-554976, mailed on May 22, 2015, 7 pages (4 page of English Translation and 3 pages of Official Copy).

* cited by examiner

DEVICES AND METHODS FOR TREATING ACCIDENTAL BOWEL LEAKAGE

CROSS-REFERENCE TO RELATED APPLICATIONS

This application claims priority to U.S. Provisional Patent Application Ser. No. 61/593,052, filed Jan. 31, 2012 and titled "ABL FLUSHABLE WIPE/BODY LINER", to U.S. Provisional Patent Application Ser. No. 61/649,749, filed on May 21, 2012 and titled "BODY LINER FOR ANAL LEAKAGE". This application is also a continuation-in-part of U.S. Design patent application No. 29/422,461, filed May 21, 2012 and titled "BODY LINER FOR ANAL LEAKAGE", and a continuation-in-part of U.S. Design patent application No. 29/437,530, filed Nov. 16, 2012 and titled "BODY LINER FOR ANAL LEAKAGE". The contents of each of these applications are hereby incorporated by reference in their entirety.

FIELD

Described here are body liners and methods for treating fecal incontinence.

BACKGROUND

Accidental bowel leakage (ABL), also known as fecal incontinence, is a widespread, debilitating condition, affecting millions worldwide. ABL is typically characterized by small amounts (typically about 1 ml or less) of viscoelastic bowel discharge including feces or otherwise-contaminated moisture, which may travel away from the anus to soil the gluteal cleft and potentially the sufferer's garments. As opposed to defecation (which occurs when the anus is opened by the anal sphincter muscles), the discharge associated with ABL may occur even when the sphincter muscles are clenched. ABL is often unpredictable, and has a significant impact on the quality of life for affected individuals. People at risk for ABL include, but are not limited to, mature persons with chronic bowel disturbances (e.g., diarrhea and IBS), who smoke, are obese, have neurological disorders (e.g., resulting from diabetes, MS, or spine and/or rectal injuries), or have undergone cholecystectomy, lower spine and/or rectal zone surgeries, women who have given birth, and men who have had prostrate treatment.

Current incontinence pads and devices do not provide an adequate solution for those suffering from ABL. Invasive approaches, including ostomy collectors, valves, plugs, and injectable gels can be intrusive, carry health risks, and may be excessive for instances of mild or moderate bowel leakage, where relatively small amounts of discharge (e.g., about 1 ml or less) is released. Traditional incontinence pads and diapers can be bulky, conspicuous, and embarrassing, and may not prevent fecal matter from exiting the intergluteal cleft. This may require additional cleanup, and may contribute to feelings of uncleanliness. Further, the bulk may make discreetly carrying replacements more difficult. A lack of satisfactory solutions may drive ABL sufferers to attempt makeshift solutions (e.g., wads of toilet paper placed in the intergluteal cleft, which are easily displaced during movement), or to avoid an active lifestyle altogether. Accordingly, it is desirable to provide discreet, non-invasive treatment devices for people suffering from ABL.

BRIEF SUMMARY

Described here are devices and methods for treating fecal incontinence. Generally, the devices described here comprise a body liner sized and configured to be placed at least partially within the intergluteal cleft. The body liner generally comprises at least one body liner layer and is configured to absorb fluid from a load of ABL. In some variations, the body liner has a body-facing surface and a rear surface opposite the body-facing surface, wherein the body liner is formed from a plurality of liner layers and comprises at least one adhesive region on the body-facing surface of the body liner. The plurality of liner layers may comprise a top sheet, a back sheet, and a core member, and each of the plurality of liner layers may be liquid absorbent. In some of these variations, the top sheet may form the body-facing surface of the body liner and the back sheet may form the rear surface of the body liner. The body-facing surface may have a higher coefficient of friction than a coefficient of friction of the rear surface. In other variations the body-facing surface may have a coefficient of friction less than that of the rear surface, or equal to that of the rear surface. In some variations, the coefficient of friction of the rear surface may be less than 0.15. In some of these variations, the coefficient of friction of the front surface is greater than 0.25.

In some variations when the body liner comprises a top sheet, a back sheet, and a core member, the core member may be positioned between the top sheet and the back sheet. The core member may be any suitable shape, such as, for example, circular or oval. The body liner may have any suitable shape, such as, for example, a butterfly shape, a rectangular shape, an oval shape, or the like. In some variations, the body liner may have a longitudinal axis, and the top sheet may have a shape comprising a first lobe on a first side of the longitudinal axis and a second lobe on a second side of the longitudinal axis. In some of these variations, the shape of the top sheet may further comprise a third lobe on the first side of the longitudinal axis and a fourth lobe on the second side of the longitudinal axis. In some of these variations, the back sheet may have a shape that is the same as the shape of the top sheet.

In some variations where the body liner comprises a top sheet and a back sheet, the back sheet and the top sheet may be at least partially bonded together. In some of these variations, the back sheet and top sheet may be bonded together around a periphery of the top sheet. In some of these variations, the back sheet and top sheet may be bonded together such that at least 80 percent of the top sheet remains unbonded. In some of these variations, the back sheet and top sheet may be bonded together such that at least 90 percent of the top sheet remains unbonded. In some variations the body liner may be configured to be flushable. In some of these variations, at least 90 percent of the body liner may be formed from one or more biodegradable materials.

In variations where the body liner comprises a top sheet, the top sheet may be configured to move fluid within the top sheet at a first wicking rate in a first direction, a second wicking rate in a second direction, and a third wicking rate in a third direction, wherein first and second directions are within a plane of the body liner, the first direction is perpendicular to the second direction, and the third direction is perpendicular to the plane of the body liner. In some of these variations, the top sheet may be configured such that the third wicking rate in the top sheet is greater than the first and second wicking rates in the top sheet. In some of these variations, the top sheet may be configured such that the first wicking rate in the top sheet is greater than the second wicking rate in the top sheet. In some of these variations, the body liner has a longitudinal axis along which the body liner may be folded when placed at least partially in the intergluteal cleft, and the first direction may be parallel to the longitudinal axis. In others of these variations, the body liner has a longitudinal axis along which the body liner is folded when placed at least partially in the intergluteal cleft, and the second direction may parallel to the longitudinal axis.

In variations where the body liner comprises a back sheet, the back sheet may be configured to move fluid within the back sheet at a first wicking rate in the first direction, a second wicking rate in the second direction, and a third wicking rate in the third direction, wherein the third wicking rate in the back sheet may be greater than the first wicking rate in back sheet and greater than the second wicking rate in the back sheet. In some of these variations, the third wicking rate in the back sheet may be the same as the third wicking rate in the top sheet. In others of these variations, the first wicking rate in the back sheet may be greater than the second wicking rate in the back sheet. In some of these variations, the first wicking rate in the top sheet may be greater than the second wicking rate in the top sheet.

In other variations of the devices described here, the devices may comprise a body liner sized and configured to be placed at least partially within the intergluteal cleft and having a body-facing surface and a rear surface opposite the body-facing surface, wherein the body liner is formed from at least one liner layer, wherein the body-facing surface has a coefficient of friction and the rear surface has a coefficient of friction. In some of these variations, the coefficient of friction of the body-facing surface is greater than the coefficient of friction of the rear surface. In others of these variations, the coefficient of friction of rear surface may be greater than the coefficient of friction of the body-facing surface. In yet other variations, the body-facing surface and rear surface may have equal coefficient of frictions. The body-facing and rear facing surfaces may have any suitable coefficients of friction. In some variations, the coefficient of friction of the body-facing surface may be greater than 0.25. In some of these variations, the coefficient of friction of the body-facing surface may be greater than 0.3. In some variations, the coefficient of friction of the rear surface may be less than 0.15. In some variations, the coefficient of friction of the rear surface may be less than 0.1. The body liner may, in some variations, comprise at least one adhesive region on the body-facing surface of the body liner When the body liner is formed from at least one liner layer, one or more portions of the body liner may be configured to be fluid absorbent. In some variations, each liner layer of the at least one liner layer may be fluid absorbent. In some variations, the at least one liner layer may comprise a top sheet and a core member, and one or both of the top sheet and core member may be fluid absorbent. In some of these variations, at least one liner layer further may comprise a back sheet, which in some variations may be positioned between the top sheet and the back sheet. The back sheet may also be fluid absorbent.

In some instances when the body liner is configured to absorb fluid, the body liner may be further configured to move fluid within the body liner at a first wicking rate in a first direction, a second wicking rate in a second direction, and a third wicking rate in a third direction, wherein the first and second directions are within a plane of the body liner, the first direction is perpendicular to the second direction, and the third direction is perpendicular to the plane of the body liner. In some of these variations, the third wicking rate in the body liner may be greater than the first wicking rate in the body liner and may be greater than the second wicking rate in the body liner. In some of these variations, the first wicking rate in the body liner may be greater than the second wicking rate in the body liner. In some of these variations, the body liner has a longitudinal axis along which the body liner may be folded when placed at least partially within the intergluteal cleft, and wherein the second direction is parallel to the longitudinal axis. In others of these variations, the body liner has a longitudinal axis along which the body liner may be folded when placed at least partially within the intergluteal cleft, wherein the first direction is parallel to the longitudinal axis. In some variations, the first wicking rate in the body liner may be greater than the second wicking rate in the body liner.

As mentioned above, the body liner may have any suitable shape. For example, in some variations, the body liner has a longitudinal axis along which the body liner may be folded when placed at least partially within the intergluteal cleft, and wherein the body liner may have a shape comprising a first lobe on a first side of the longitudinal axis and a second lobe on a second side of the longitudinal axis. In some of these variations, the shape of the body liner may further comprise a third lobe on the first side of the longitudinal axis and a fourth lobe on the second side of the longitudinal axis. In some variations, the rear surface of the body liner may be configured to have a reduced coefficient of friction (e.g., may be polished, may comprise one or more friction-reducing coatings, combinations thereof and the like). In other variations, the body-facing surface of the body liner may be configured to enhance the coefficient of friction of the body-facing surface (e.g., the body-facing surface may be textured or roughened, or the like). In some variations, the body liner may be configured to be flushable. In some variations, each liner layer of the at least one liner layer may be formed from one or more cellulosic materials.

In still other variations of the devices described here, the devices may comprise a body liner sized and configured to be placed at least partially within the intergluteal cleft, the body liner having a longitudinal axis along which the body may be folded when placed at least partially with the intergluteal cleft, a body-facing surface, and a rear surface opposite the body-facing surface, wherein the body liner is formed from at least one liner layer, wherein the body liner may be configured to move fluid within the body liner at a first wicking rate in a first direction, a second wicking rate in a second direction, and a third wicking rate in a third direction, wherein first and second directions are within a plane of the body liner, the first direction is perpendicular to the second direction, and the third direction is perpendicular to the plane of the body liner, and wherein the third wicking rate in the body liner is greater than the first wicking rate in the body liner and is greater than the second wicking rate in the body liner. In some of these variations, the first wicking rate in the body liner may be greater than the second wicking rate in the body liner. In some of these variations, the first direction may be parallel to the longitudinal axis. In others of these variations, the second direction may be parallel to the longitudinal axis.

In some variations the body liner may be configured such that when folded along the longitudinal axis, fluid applied to a portion of the body-facing surface on a first side of the longitudinal axis is transferred in the third direction to the a portion of the rear surface on the first side of the longitudinal axis, and may be further transferred to a portion of the rear surface on a second side of the longitudinal axis. In some variations, the body liner may comprise at least one adhesive region on the body-facing surface of the body liner. In some variations, each liner layer of the at least one liner layer may be fluid absorbent. The at least one liner layer may comprise a top sheet and a core member. In some of these variations, at least one liner layer may further comprise a back sheet. In some of these variations, the core member may be positioned between the top sheet and the back sheet. In some variations, the body-facing surface may have a coefficient of friction greater than a coefficient of friction of the rear surface.

In still other variations of the devices described here, a device may comprise a body liner sized and configured to be placed at least partially within the intergluteal cleft, the body liner having a longitudinal axis along which the body liner may be folded when placed at least partially with the intergluteal cleft, a body-facing surface, and a rear surface opposite the body-facing surface, wherein the body liner may be formed from at least one liner layer, wherein the body liner may be configured to move fluid within the body liner at a first wicking rate in a first direction, a second wicking rate in a second direction, and a third wicking rate in a third direction, wherein first and second directions are within a plane of the body liner, the first direction is perpendicular to the second direction, and the third direction is perpendicular to the plane of the body liner, and wherein the second wicking rate in the body liner is greater than the first wicking rate in the body liner. In some of these variations, the third wicking rate in the body liner is greater than the second wicking rate in the body liner. In others of these variations, the first direction is parallel to the longitudinal axis. In still others of these variations, the second direction is parallel to the longitudinal axis.

In some variations, the body liner may be configured such that when folded along the longitudinal axis, fluid applied to a portion of the body-facing surface on a first side of the longitudinal axis may be transferred in the third direction to the a portion of the rear surface on the first side of the longitudinal axis, and may be further transferred to a portion of the rear surface on a second side of the longitudinal axis. The body liner comprises at least one adhesive region on the body-facing surface of the body liner. In some variations, each liner layer of the at least one liner layer is fluid absorbent. The at least one liner layer may comprise a top sheet and a core member. In some of these variations, the at least one liner layer may further comprise a back sheet. In some of these variations, the core member may be positioned between the top sheet and the back sheet. In some instances, the body-facing surface may have a coefficient of friction greater than a coefficient of friction of the rear surface.

In yet other variations of the devices described here, the devices may comprise a body liner sized and configured to be placed at least partially within the intergluteal cleft, the body liner having a longitudinal axis along which the body is folded when placed at least partially with the intergluteal cleft, a latitudinal axis perpendicular to the longitudinal axis and intersecting the longitudinal axis at a target point, a body-facing surface, and a rear surface opposite the body-facing surface, wherein the body liner is formed from at least one liner layer, wherein the body liner has a shape comprising a first lobe, a second lobe, a third lobe, and a fourth lobe, wherein the first and second lobes are positioned on a first side of the longitudinal axis and the third and fourth lobes are positioned on a second side of a longitudinal axis. In some variations, the first and third lobes may be positioned on a first side of the latitudinal axis, and the second and fourth lobes may be positioned on a second side of the latitudinal axis. In some of these variations, a height of the first lobe along the longitudinal axis may be greater than a height of the second lobe along the longitudinal axis. In others of these variations, a height of the third lobe along the longitudinal axis may be greater than a height of the fourth lobe along the longitudinal axis.

In some variations, each liner layer of the at least one liner layer may be fluid absorbent. In some variations, the at least one liner layer may comprises a top sheet and a core member. In some of these variations, the core member may have a circular or oval shape, and the shape of the top sheet may be the same shape as the body liner. In some variations, the core member may have a shape that is the same as the overall shape of the body liner except that it is a smaller size. In some of these variations, the at least one liner layer further comprises a back sheet. In some of these variations, the core member may be positioned between the back sheet and the top sheet. In some of these variations, the back sheet and the top sheet may be at least partially bonded together. In some of these variations, the back sheet and top sheet may be bonded together around a periphery of the top sheet. In some of these variations, the back sheet and top sheet may bonded together such that at least 80 percent of the top sheet remains unbonded.

In some variations, the body-facing surface may have a higher coefficient of friction than a coefficient of friction of the rear surface. In some variations, the body liner may be configured to be flushable. In some variations the body liner may comprise at least one adhesive region on the skin-facing surface. In some variations the devices may further comprise a release liner removably attached to the body liner. In some variations, the body liner may be configured to move fluid within the body at a first wicking rate in a first direction, a second wicking rate in a second direction, and a third wicking rate in a third direction, wherein first and second directions are within a plane of the body liner, the first direction is perpendicular to the second direction, and the third direction is perpendicular to the plane of the body liner. In some of these variations, the body liner may be configured such that the third wicking rate in the body liner is greater than the first and second wicking rates in the body liner. In other variations, the body liner may be configured such that the first wicking rate in the body liner is greater than the second wicking rate in the body liner.

In still other variations of the devices described here, the devices may comprise a flushable body liner sized and configured to be placed at least partially within the intergluteal cleft and having a longitudinal axis, a body-facing surface and a rear surface opposite the body-facing surface, and at least one adhesive region on the body-facing surface of the body liner. In some of these variations, the at least one adhesive region may comprise a first adhesive region on a first side of the longitudinal axis and a second adhesive region on a second side of the longitudinal axis. The body liner may comprise a first adhesive zone on the body-facing surface on a first side of the longitudinal axis and a second adhesive zone on the body-facing surface on a second side of the longitudinal axis, wherein the body liner does not include adhesive regions outside of the first and second adhesive zones. In some of these variations, each of the first and second adhesive zones comprise an arc segment having an outer radius of curvature less than about 5.1 cm and an inner radius of curvature of at least about 1 cm. In some of these variations, the arc segments of each of the first and second adhesive zones may be separated from the longitudinal axis by a distance of at least 0.65 cm.

DETAILED DESCRIPTION

Figure 1A:
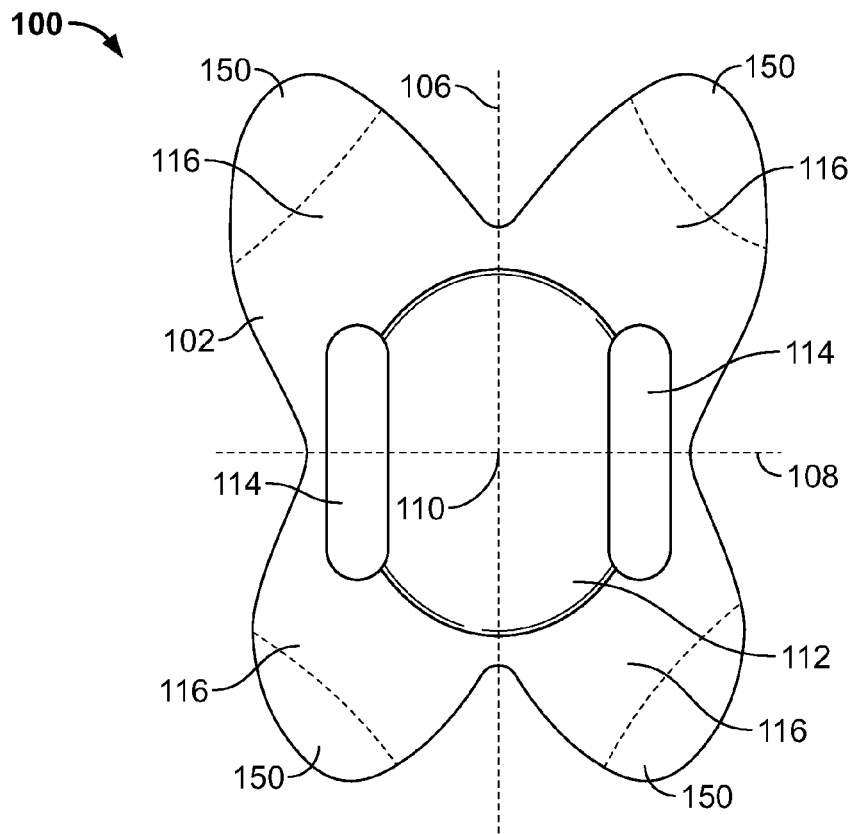
FIGS. 1A and 1B show a top view and a bottom view, respectively of a variation of the body liners described here.

Described here are body liners and methods of using body liners to treat accidental bowel leakage. These body liners, which may be absorbent and/or flushable, are generally sized and configured to be placed at least partially within the intergluteal cleft (i.e., between the buttocks) and near the anus. When placed at least partially within the intergluteal cleft, the body liners may provide a wearer with physical feedback which may reassure or otherwise provide emotional confidence to the wearer. In some instances, the body liners may include one or more features or may otherwise be configured to be promote maintenance of the body liner in a position at least partially within the intergluteal cleft, and may also be configured to help minimize the risk of displacement or dislodgement of the body liner (such as, for example, during movement of the wearer or during actions such as urination). For example, in some variations the body liners may comprise one or more adhesive regions which may adhere to the skin of the wearer (e.g., skin of the buttocks) to help maintain the placement and positioning of the body liner. The body liners described here may be worn while presenting little or no visual indication of use by the wearer, and may be of a sufficiently small size such that replacements may discreetly carried by a wearer (e.g., in a pocket or purse). Additionally, the body liners may be configured to be retrieved in a manner that does not require wearers to reach into the intergluteal cleft or otherwise soil their fingers. Accordingly, the body liners described here may present a discreet, comfortable, and sanitary treatment option for ABL.

When placed at least partially within the intergluteal cleft, the body liners described here may be configured to absorb and retain accidental anal discharge. This discharge may include small amounts of fecal matter having relatively high water content. Accordingly, the body liners may be configured to be at least partially fluid absorbent, such that the body liner is capable of absorbing fluid from the anal discharge. By absorbing fluid from anal leakage, the body liners can dewater the feces, which may act to immobilize any fecal matter that the body liner may be unable to absorb (e.g., by virtue of the size and/or consistency of the fecal matter). Placing an absorbent portion of the body liner at or near the anus may allow the body liner to dewater anal discharge before the discharge can move too far from the anus, which may help reduce the risk of soiling a wearer's undergarments or other clothing as well as minimizing odors that may otherwise occur by spread of fecal matter. Additionally, immobilizing discharge at or near the anus may give a wearer time to find a restroom and may provide for discreet disposal. Limiting the spread or movement of the discharge may allow for reduced cleanup, providing a hygienic treatment option.

The body liners may be formed from one or more liner layers, and some or all of the liner layers may be configured to be fluid absorbent. Generally, an absorbent liner layer may be configured to absorb and at least partially retain fluid that contacts the liner layer, and may be configured to transfer fluid to adjoining absorbent liner layers as appropriate. In some of the variations in which a body comprises multiple liner layers, each of the liner layers is at least partially fluid absorbent. In these variations, the body liner may not include any fluid impermeable layer. It should be appreciated, however, that these body liners may be packaged with one or more fluid-impermeable release liners that may be removed prior to placement of the body liner in the intergluteal cleft. Additionally, as will be described in more detail below, in some variations one or more portions of the body liner (namely a portion or portion configured to extend out of the intergluteal cleft) may be configured to have a reduced absorbency.

The body liners are generally configured as a substantially flat sheet having a body-facing surface and a rear surface opposite the body-facing surface, and which may be folded when placed in the intergluteal cleft. The body liners, however, may vary in thickness along the length and/or width of the body liner, and may have one or more features (e.g., a barrier member or the like) which may project or otherwise extend from the body-facing surface and/or rear surface of the body liner. When the body liner is folded for placement at least partially within the intergluteal cleft, such folding may position the body-facing surface of the body liner in contact with the wearer's skin (e.g., the skin of the buttocks) and to position the rear surface of the body liner into contact with itself (i.e., at least a portion of the rear surface on one side of the fold may contact at least a portion the rear surface on the other side of the fold). When a body liner comprises one or more adhesive regions (as will be described in more detail below) on the body-facing surface of the body liner, folding the body liner at least partially into the intergluteal cleft may position the one or more adhesive regions such that they adhere to the skin of the wearer's buttocks, which may help position and hold the body liner in place relative to the skin and anus of the wearer.

The one or more liner layers of the body liner may define the body-facing and rear surfaces of the body liners described here. For example, when the body liner comprises a single liner layer, the liner layer may have a body-facing side and a rear side opposite the body-facing side. Since the liner layer is the only layer of the body liner, the body-facing side of the liner layer may form the body-facing surface of the body liner and the rear side of the liner layer may form the rear surface of the body liner. In variations where the body liner comprises multiple liner layers (e.g., a top sheet and/or a core member and/or a back sheet, such as will be described in more detail below), each liner layer may have a body-facing side and a rear side opposite the body-facing side. The body-facing sides of some or all of the liner layers may form the body-facing surface of the body liner, while the rear sides of some or all of the liner layers may form the rear surface of the body liner. For example, in some variations where a body liner includes a top sheet and a core member that is smaller than the top sheet and attached thereto, the body-facing side of the top sheet may form the body-facing surface of the body liner. The rear surface of the body liner, however, may be formed from a combination of the rear side of the core member as well as the portions of the rear side of the top sheet that are not covered by the core member. In another example, a body liner may comprise a top sheet, a back sheet having the same size and shape as the top sheet, and a core member enclosed therebetween. In these variations, a body-facing side of the top sheet may form the body-facing surface of the body liner while a rear side of the back sheet may form the rear surface of the body liner. The core member, by virtue of its enclosure between the top sheet and the back sheet, may not form any portion of the external surfaces of the body liner.

The body liners described here may include any suitable number of liner layers. In some variations, the body liner may comprise a single liner layer. In other variations, the body liner may comprise a plurality of liner layers. In some variations, the body liner may comprise two liner layers. In some of these variations, the body liner may comprise only two liner layers. In other variations, the body liner may comprise three liner layers. In some of these variations, the body liner may comprise only three liner layers. It should be appreciated that when the body liners are described here as having a specific number of liner layers (e.g., a single liner layer, only two liner layers, etc.), it should be appreciated that that the body liner may be packaged with one or more removable release liners that are removed prior to use, as described in more detail below, but that the release liners are not considered a liner layer. It should also be appreciated that the body liner may comprise one or more coatings, barrier members, or the like and that these additional features are not considered a separate body liner layer.

When the body liners described here comprise multiple liner layers, the body liners generally comprise a top sheet, and may further comprise a core member and/or a back sheet. For example, in some variations, a body liner may comprise a first liner layer and a second liner layer, such that the first liner layer is a top sheet, and the second layer is a core member. In some of these variations, the only liner layers of the body liner are the top sheet and the core member (i.e., the body liner does not include any additional liner layers). In other variations, a body liner may comprise a first liner layer and a second liner layer, wherein the first liner layer is a top sheet and the second liner layer is a back sheet. In some of these variations, only liner layers of the body liner are the top sheet and the back sheet are the only liner layers. In still other variations, the body liner may not include a top sheet. For example, in some variations a body liner may comprise a core member as a first liner layer and a back sheet as a second liner layer, and may not include a top sheet.

In some variations, the body liners described here may comprise at least three liner layers. For example, in some variations, the body liner may comprise a first layer, a second layer, and a third layer, wherein the first layer is a top sheet, the second layer is a core member, and the third layer is a back sheet. In some of these variations, the only liner layers of the body liner are the top sheet, core member, and back sheet. In other variations, the body liner may comprise one or more additional liner layers. For example, in some variations a body liner may comprise two or more core members. The top sheets, core members, and back sheets suitable for use with the body liners described here will each be described in more detail below, but it should be appreciated that when a body liner is described here as including a top sheet, core member, and/or back sheet, the body liner may include any combination of top sheets, core members and/or back sheets such as those described below.

Top Sheet

In variations where a body liner includes is a top sheet, the top sheet is typically the topmost layer of the body liner (although it should be appreciated, as described above, that one or more release liners may be temporarily attached to the top sheet). When a body liner including a top sheet is placed in the intergluteal cleft, the top sheet may be placed into contact with skin of the buttocks. Accordingly, it may be desirable to configure the top sheet from a soft and comfortable material. In some instance the top sheet may be formed from one or more nonwoven materials. For example, in some variations the top sheet may be formed from one or more air-laid non-woven materials, such as Gladfelter DT075.100. In other variations, the top sheet may be formed from one or spun-laid or spun-bound materials, wet-laid materials, electrostatically-laid materials, combinations thereof or the like. In still other variations, the top sheet may be formed from one or more woven materials. The top sheet is preferably formed from one or more biodegradable materials, which may contribute to the flushability of the body liner, as will be described in more detail below. In some instances, the top sheet may be configured to increase the softness of the top sheet. For example, in some variations one or more needles, combs, air jets and/or water jets may separate fibers of the top sheet layer to increase the loft of the top sheet.

The top sheet is also preferably configured to be fluid absorbent, and may be configured to have any suitable absorbency. For example, in some variations the top sheet may have an absorbency of at least about 15 g/g. When a body comprises a top sheet and a back sheet and/or core member, the top sheet may be configured to transfer fluid absorbed by the top sheet to the back sheet and/or core member, such as will be described in more detail below. In these instances, it may be also desirable for the top sheet to retain at least a portion of the fluid absorbed by the top sheet. Some individuals may not realize when an incidence of ABL has occurred. By retaining fluid within the top sheet, the soiled portions of the top sheet may feel wet to the skin contacting the top sheet (as opposed to a dry sensation provided by the top sheet when the body liner is unsoiled), which may provide an indication to the wearer that an anal leakage incident has occurred and that the body liner should be replaced. This indication may occur prior to the spread of odor (which may be minimized by the body liner immobilizing leakage near the anus), and this may allow the wearer to avoid a potentially embarrassing incident.

The top sheet may have any suitable size and shape, such as will be described in more detail below. For example, the top sheet may have a circular shape, an oval shape, a rectangular shape, a lobed shape (e.g. a butterfly shape), or the like. The body liner may have a thickness, which may at least partially depend on the number of liner layers of a body liner. For example, in some variations where a body liner comprises a single liner layer including a top sheet, the top sheet may have a thickness of about 1.5 mm, between about 1.25 and about 1.75 mm, or the like. In some variations where a body liner comprises a plurality of liner layers (e.g., a top sheet and a core member and/or a back sheet), the top sheet may have a thickness of about 0.5 mm, between about 0.25 and about 0.75 mm, or the like.

In variations, the top sheet may configured such that one or more portion of the body liner may be at least partially viewed therethrough (e.g., the top sheet may be porous and/or formed from one or more partially-translucent materials). In variations where the body liner comprises a top sheet, a back sheet, and a core member positioned between the top sheet and the back sheet, top sheet may be configured to allow for visualization of the core member through the top sheet.

Core Member

When the body liners described here comprise one or more core members, core members are typically positioned beneath the top sheet of the body liner. The core members are preferably configured to absorb fluid, and may have any suitable absorbency. For example, in some variations the core member has an absorbency of at least 20 g/g. When a body liner comprises a top sheet and a core member, the core member may have an absorbency equal to that of a top sheet. In other variations, the core member may have a greater absorbency than the top sheet. For example, in some variations a body liner may comprise a core member having a greater absorbency than a top sheet, wherein the top sheet has an absorbency of at least about 15 g/g and the core member has an absorbency of at least about 20 g/g. The core member may be formed from any suitable non-woven or woven material, such as described in more detail above. In some variations, the core member may be preferably formed from a non-entangled, wet-laid pulp, such as EAM Novathin® J1400. The core member may preferably be formed from one or more biodegradable materials, which may contribute to the flushability of the body liner, as described in more detail below.

When positioned beneath a top sheet, the core member may receive and absorb fluid from the top sheet. Additionally, in variations where the body liner comprises a top sheet, a core member, and a back sheet, at least some of the fluid absorbed by the core member may be transferred to the back sheet. The core member may have any suitable thickness. In some variations, the core member may have a thickness of at least 1 mm. In other variations, the core member may have a thickness of at least 2 mm. The thickness of the core member may be increased to increase the absorbency of the body liner.

Back Sheet

When the body liners described here comprise a back sheet, the back sheet is typically the bottom-most layer of the body liner. In variations where the body liner additionally comprises one or more core members, the core members may be positioned between the top sheet and the back sheet. The back sheet is also preferably configured to be fluid absorbent. For example, in some variations the back sheet may have an absorbency of at least about 1 g/g. The back sheet may have an absorbency greater than that that of the top sheet, equal to that of the top sheet, or less than that of the top sheet. In variations where the body liner comprises one or more core members, the back sheet may have an absorbency greater than that that of the core member, equal to that of the core member, or less than that of the core member. For example, in some variations the back sheet may have an absorbency less than both the top sheet and the core member. Generally, it may be preferable to configure that back sheet to have greater structural integrity than the top sheet and/or core member.

When the back sheet is fluid absorbent, the back sheet typically receives fluid from top sheet and/or a core member (in variations in which the body liner comprises a core member). When the body liner is folded and placed in the intergluteal cleft, a portion of the back sheet on one side of the fold may be placed in contact with a portion of the back sheet on the other side of the fold. An absorbent body liner may be able to transfer fluid from the back sheet on one side of the fold to the back sheet on the other side of the fold by virtue of this contact.

The back sheet may be made from any suitable non-woven or woven materials, such as described in more detail above. For example, in some variations the back sheet may formed from one or more hydroentangled non-woven materials, such as, for example Suominen WL784450. The back sheet is preferably formed from one or more biodegradable materials, which may contribute to the flushability of the body liner. The back may have any suitable size. For example, the back sheet may have a thickness of about 1 mm, between about 0.5 mm and about 1.5 mm, or the like. In some variations, the back sheet may be configured such that one or more portions of the body liner may be at least partially visualized through the back sheet, such as described above. For example, in variations where the body liner comprises a top sheet, a back sheet, and a core member positioned between the top sheet and the back sheet, the back sheet may be configured to allow for visualization of the core member through the back sheet.

Exemplary Body Liner Construction

Figure 1B:
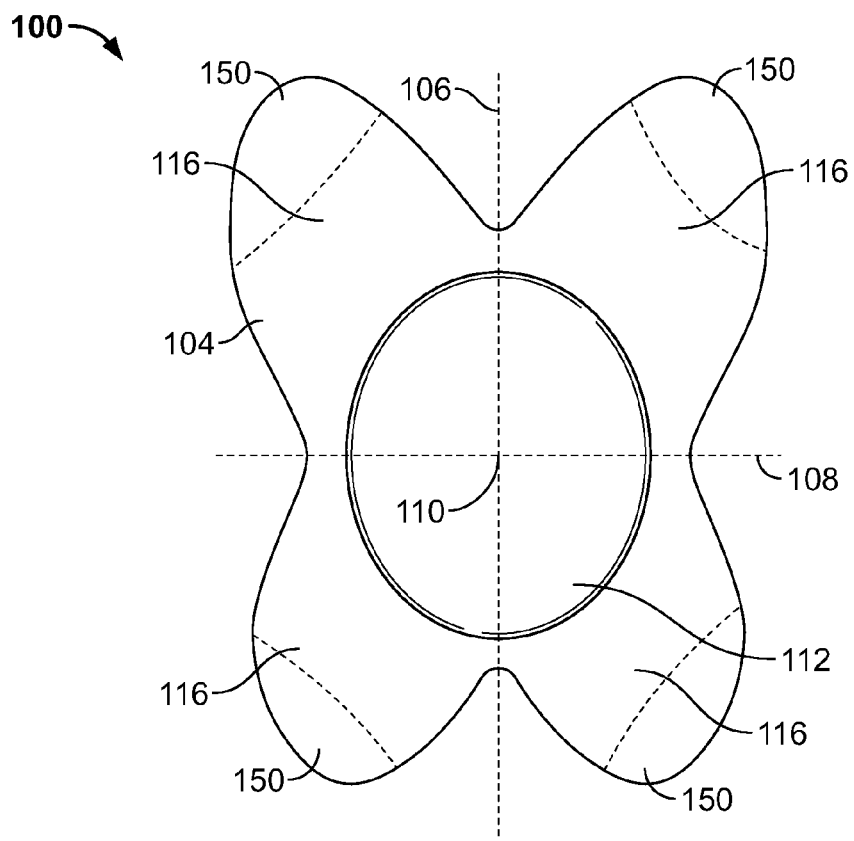

FIGS. 1A-1E depicts an illustrative variation of the body liners described here. FIGS. 1A and 1B show top and bottom views, respectively of a variation of a body liner (100). The body liner (100) may have a body-facing surface (102) (as shown in FIG. 1A) and a rear surface (104) (shown in FIG. 1B) opposite the body-facing surface (102). The body liner (100) may include a longitudinal axis (106) and a lateral axis (108) within the plane of the body liner (100). The longitudinal (106) and lateral (108) axes are orthogonal, and may intersect at a target point (110). When the body liner (100) is placed at least partially within the intergluteal cleft, it is intended that the body liner be positioned such that the target point (110) is positioned over the anus at or near the anus of the wearer and the body liner (100) be folded substantially along the longitudinal axis (106). It should be appreciated that the longitudinal axis, the lateral axis, and the target point are relative terms which may be useful in describing the size, shape, and features of the body liners described here. While the target point (110) is shown in FIGS. 1A and 1B as positioned near the center of the body liner (100), it should be appreciated that in some instances it may be desirable to configure a body liner such that the target point is offset from the center of the body liner. For example, in some variations a target point may positioned closer to a front end of the body liner than a back end of the body liner, which may facilitate urination when the body liner is in place.

Also shown in FIGS. 1A and 1B is a target zone (112). Generally, a target zone (112) surrounds the target point (110) and is intended as the primary region of the body liner for receiving bowel leakage. When the target zone (112) receives a load of bowel leakage, the target zone (112) may be configured to dewater and immobilize the leakage. It may be desirable to configure the body liner (100) to allow the target zone (112) to dewater an anticipated ABL load. For example, the target zone (112) may be configured to dewater an ABL load of at least about 0.05 ml. In some of these variations, the target zone (112) may be configured to dewater an ABL load of 0.25 ml or more, and in some of these variations the target zone (112) may be configured to dewater an ABL load of 5 ml or more. The target zone (112) may be any suitable size or shape. In some variations, the target zone (112) may have an area between about 25 $cm^2$ and about 55 $cm^2$. In some of these variations, the target zone (112) may preferably have an area between about 30 $cm^2$ and about 50 $cm^2$. In some of these variations, the target zone (112) may have an area between about 35 $cm^2$ and about 45 $cm^2$. In some instances that target zone may have at least a 3 cm radius from the target point. The target zone (112) may be oval, rectangular, hourglass shaped, irregularly shaped, or the like, as will be described in more detail below.

Additionally, in some variations it may be desirable to limit the amount of absorbed fluid that travels beyond the target zone (112). For example, when one or more portions of the body liner is configured to extend at least partially from the intergluteal cleft (e.g., so that a wearer can grasp the exposed portion or portions to remove the body liner), limiting the ability of fluid absorbed to travel past the target zone and to the exposed portions of the body liner may reduce the likelihood that the wearer will soil his or her fingers when removing the body liner (100). While the target zone (112) is shown in FIGS. 1A and 1B as being centered on the target point (110), the target zone (112) need not be. In some variations, the boundaries of the target zone may be defined by the boundaries of a core member, such as will be described in more detail below.

The target zone of a body liner may be configured to have one or more properties that are different than those of surroundings portions of the body liner. In some variations, the target zone of a body liner may be configured to have a greater absorbency than surrounding portions of the body liner. For example, in some variations the target zone may have a thickness greater than the thickness of surrounding portions of the body liner, which may allow for greater fluid absorption relative to thinner portions of the body liner. Additionally or alternatively, the target zone may include one or more additional liner layers which may increase the absorbency of the target zone. Additionally or alternatively, the target zone may be formed from a different material or materials than the material or materials of the surrounding portions of the body liner. In these variations, the material or combination of materials forming the target zone may be more absorbent than the material or combination of materials forming the surrounding portions of the body liner. Additionally or alternatively, the target zone may be imbedded with one or more absorbent particles, such as one or more super absorbent polymers, which may increase the absorbency of the target zone.

The body liner (100) shown in FIGS. 1A and 1B has a target zone (112) having an oval shape, but it should be appreciated that the body liners described here (including the body liner (100)) may have a target zone having any suitable shape (e.g., a circular shape, a square or rectangular shape, a triangular shape, an hourglass shape, an irregular shape, or the like). Additionally, the body liner (100) shown in FIGS. 1A and 1B is shown as having an overall butterfly shape having four lobes (116) extending from the target zone (112), it should be appreciated that the body liners described here may have any suitable shape, such as will be described in more detail below.

In some instances, it may be desirable to configure the body liners described here to avoid contact with or occlusion of the genitals of the wearer. For example, in instances in which a female wearer positions a body liner at least partially in the intergluteal cleft to position a target point at the intergluteal cleft, it may be desirable to configure the body liner to not occlude the vagina. If a portion of the body liner occludes the vagina or is positioned too close to the vagina, the body liner may absorb urine or menstrual fluid from the vagina, which may require removal of the body liner. In other variations, contact between the body liner and the genitals may cause bunching of the body liner and/or discomfort to the wearer. Accordingly, the body liner may be configured to avoid contact with or occlusion of genitals. For example, in the illustrative variation of the body liner (100) shown in FIGS. 1A and 1B, the length of the body liner (100) along the longitudinal axis (106) between the target point (110) and the front end of the body liner (100) may be less than the distance between the anus and the genitals. In some variations the length of the body liner (100) along the longitudinal axis (106) between the target point (110) and the front end of the body liner (100) may be less may be less than about 3.5 cm.

Figure 1C:
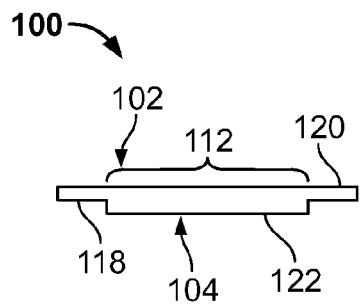
FIGS. 1C-1E depict cross-section side views of variations of the body liner shown in FIGS. 1A and 1B.
Figure 1D:
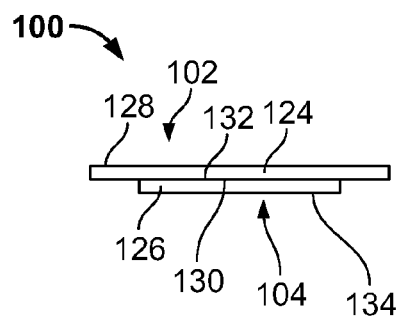
Figure 1E:
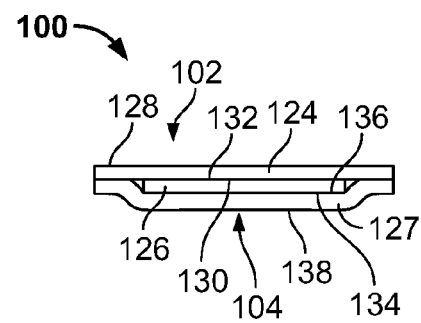

The body liner (100) shown in FIGS. 1A and 1B may be formed from one or more liner layers, such as discussed briefly above. FIGS. 1C-1E depict different variations in which the body liner (100) may be formed from one or more liner layers. FIG. 1C depicts a cross-sectional side view (taken along the longitudinal axis (106)) of a variation in which the body liner (100) may be formed from a first liner layer (118) (e.g., a top sheet such as those described above). In some of these variations, the first liner layer (118) may be the only liner layer of the body liner (100). As shown in FIG. 1C, the first liner layer (118) may have a body-facing side (120) and a rear side (122) opposite the body-facing side (120). The body-facing side (120) of the first liner layer (118) may form the body-facing surface (102) of the body liner (100) and the rear side (122) of the first liner layer (118) may form the rear surface (104) of the body liner (100). In some variations, such as that shown in FIG. 1C, the first liner layer (118) may have a greater thickness in the target zone (112) than in the surrounding portions of the body liner (100). The increased thickness of the target zone (112) may increase the overall absorbency of the target zone (112). It should be appreciated, however, that in other instances the target zone (112) may have the same thickness as or a smaller thickness than surrounding portions of body liner (for example, in instances where the target zone (112) may comprise one or more absorbent agents imbedded therein).

FIG. 1D depicts a cross-sectional side view (taken along the longitudinal axis (106)) of a variation in which the body liner (100) may comprise two liner layers. As shown there, the body liner (100) may comprise a top sheet (124) and a core member (126). In some of these variations, the top sheet (124) and core member (126) may be the only liner layers of the body liner. The top sheet (124) and the core member (126) may be any combination of the top sheets and core members such as those described in more detail above. The top sheet (124) and core member (126) may each have a body-facing side ((128) and (132), respectively) and a rear side ((130) and (134), respectively) opposite the body-facing side. At least a portion of the body-facing side (132) of the core member (126) may be attached to the rear side (130) of the top-sheet (124) to connect the liner layers, as will be described in more detail below. In the variation shown in FIG. 1D, the body-facing side (128) of the top sheet (124) may form the body-facing surface (102) of the body liner (100), while the rear side (134) of the core member (126) and the portion of the rear side (130) of the top sheet (124) not covered by the core member (126) may form the rear surface (104) of the body liner (100). Additionally, in some of these variations, the size and shape of the core member (126) may define the boundaries of the target zone (112).

FIG. 1E depicts a cross-sectional side view (taken along the longitudinal axis)) of a variation in which the body liner (100) may comprise three liner layers. As shown there, the body may comprise a top sheet (124) and a core member (126) (which are labeled as set forth in FIG. 1D), and may further comprise a back sheet (127). In some variations, the top sheet (124), core member (126), and back sheet (127) may be the only liner layers of the body liner. The back sheet (127) may have a body-facing side (136) and a rear side (138) opposite the body-facing side (136). In the variation shown in FIG. 1E, the core member may be enclosed between the top sheet (124) and the back sheet (127). In these variations, top sheet (124) and back sheet (127) may be connected, as will be described in more detail below. In some of these variations, the core member (126) may also be attached to top sheet (124) and/or the back sheet (127). In the variation shown in FIG. 1E, the body-facing side (128) of the top sheet (124) may form the body-facing surface (102) of the body liner (100) and the rear side (138) of the back sheet (127) may form the rear surface (104) of the body liner (100). In some of these variations, the size and shape of the core member (126) may define the boundaries of the target zone (112).

As shown in FIG. 1A, the body liner (100) may comprise one or more adhesive regions (114) on the body-facing surface (102) of the body liner (100). In the variation shown in FIG. 1A, the body liner (100) has an adhesive region (114) on each side of the longitudinal axis (106), although it should be appreciated that in some variations the body liner (100) may only have one or more adhesive regions (114) on one side of the longitudinal axis (106). In some variations, the body liner (100) may have one or more adhesive regions that cross the longitudinal axis (106). In still other variations, the body liner (100) may not comprise any adhesive regions. The size, shape, and placement of adhesive regions for use with the body liners described here will be described in more detail below.

Body Liner Retrieval

The body liners described here may be constructed and arranged to allow for removal of the body liner from the intergluteal cleft. Specifically, it may be desirable to configure the body liners to allow for removal of the body liner while minimizing the likelihood that the wearer soils his or her fingers during removal of the body liner. For example, one or more retrieval devices may be attached to the body liner. In some of these variations, a string, ribbon, tab, or the like may be attached to one or more portions of the body liner (e.g., via an adhesive, welding, or the like). In these variations, when the body liner is placed at least partially within the intergluteal cleft, the string or ribbon may be positioned to extend at least partially out of the intergluteal cleft. To remove the body liner (e.g., after a bowel leakage incident), a wearer may pull on the string or ribbon to pull the body liner away from the intergluteal cleft.

In some variations, the body liner may be sized and configured to extend at least partially from the intergluteal cleft when positioned. For example, in variations in which the body liner comprises one or more lobes, one or more of the lobes may extend at least partially from the intergluteal cleft.

Figure 1F:
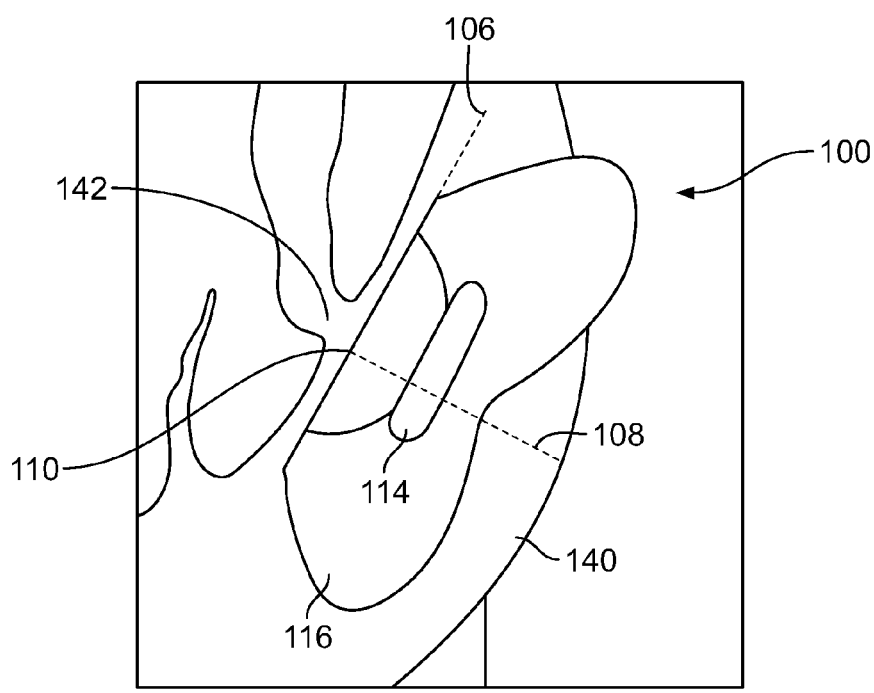
FIG. 1F shows the body liner of FIGS. 1A and 1B placed at least partially in the intergluteal cleft.

FIG. 1F shows the illustrative variation of the body liner (100) (described above with respect to FIGS. 1A and 1B) placed at least partially within the intergluteal cleft (140). As shown there, the body liner (100) may be folded along the longitudinal axis (106) and positioned such that the target point (110) is positioned at or near the anus (142). The body liner (100) may be sized such that when the target point (110) is positioned at or near the anus (142), at least a portion of one or more of the lobes (116) may extend at least partially outside of the intergluteal cleft. The portion of the body liner that extends from the intergluteal cleft is preferably large enough to allow a wearer to grasp the exposed portion of the body liner. In some of these variations, the body liner may be sized and configured such that at least a portion of the body liner (e.g., one or more lobes) extends at least 1 cm from the intergluteal cleft when the target point (110) is positioned at or near the anus (142)). The wearer of the body liner may grab one or more of the exposed portions of the body liner, and may pull on the body liner to remove the body liner from the intergluteal cleft. By allowing the wearer to remove the body liner without reaching into the intergluteal cleft, a wearer is less likely to soil his or her fingers when removing the body liner.

While it may be desirable for at least a portion of the body liner to extend from the intergluteal cleft, it may also be desirable to limit the amount of extension of the body liner from the intergluteal cleft. If the body liner extends too far from the intergluteal cleft, clothing may catch or snag the body liner (e.g., when putting on or removing undergarments or pants) which may dislodge or displace the body liner from its intended position. Accordingly, in some variations the body liner may be sized, configured, and positioned such that at least a portion of the body liner extends out of the intergluteal cleft and the portions of the body liner extending out of the intergluteal cleft extend less than about 2.5 cm from the intergluteal cleft. In some of these variations, at least a portion of the portions of the body liner extending out of the intergluteal cleft may extend at least 1 cm out of the intergluteal cleft.

When the body liners described here are configured to extend at least partially from the intergluteal cleft, such as described immediately above, it may be desirable to limit the absorbance of the exposed portions of the body liner. In these variations, decreasing the absorbance of the exposed portions of the body liner may reduce the ability of absorbed fluid to reach the exposed portions of the body liner, thereby reducing the likelihood that a wearer will grab a soiled portion of the body liner during removal of the body liner. In some variations, the exposed portions of the body liner may be crimped, crushed, or otherwise compressed to reduce the absorbance of the exposed portions. For example, when the body liner comprises one or more lobes that are configured to extend at least partially from the intergluteal cleft (such as lobes (116) of the body liner (100) described above with respect to FIG. 1F), the lobes may be crimped, crushed, or otherwise compressed. Additionally or alternatively, the exposed portions of the body liner may be covered by one or more fluid-impervious materials. In these variations, if fluid absorbed by the body liner reaches the exposed portions of the body liner, the fluid-impervious covering may prevent fluid from being transferred to the wearer's fingers. For example, in some of the variation of the body liner (100) described above with respect to FIGS. 1A and 1B, lobes (116) may comprise coated regions (150) which may be coated with one or more fluid-impervious materials. While each of the lobes (116) are shown in FIGS. 1A and 1B as having a coated region (150), it should be appreciated that only some of the lobes (e.g., only the lobes on a first side of the lateral axis (108), only the lobes on a first side of the longitudinal axis (106), or the like) may comprise a coated region (150).

Flushability

In some variations, the body liners described here may be configured to be entirely flushable. Panty liners, menstrual pads and incontinence pads generally are not flushable, by virtue of their relatively large size and/or the presence of fluid-impermeable layers. When a product is not flushable, a wearer must find alternative means of disposal for the product, or risk clogging a toilet by attempting to flush the device (which may create an embarrassing situation for the wearer). The odors associated with anal leakage may make discreet disposal of fecal incontinence pads difficult, especially in public restrooms where trash receptacles are generally not provided in individual stalls. Accordingly, it may be desirable to configure the body liners described here to be flushable for discreet disposal in a toilet.

When the body liners described here are configured to be flushable, they may be configured to be flushable based on INDA and/or EDANA guidelines (e.g., the body liner may clear properly-maintained toilets and pipe systems under expected product usage conditions and may be compatible with existing wastewater disposal systems). In some of these variations, the body liner may be configured to dispersible based on INDA and/or EDANA guidelines. In some variations, the body liner may be configured to use little or no non-biodegradable materials. In some of these variations, less than 10% of the mass of the body liner may be formed from non-biodegradable materials. In some of these variations, less than 5% of mass of the body liner may formed from non-biodegradable materials. In some variations, each of the liner layers is formed from one or more biodegradable materials (each liner layer may be formed from the same biodegradable material or combination of biodegradable materials, or different liner layers may be formed from different biodegradable materials or combinations of biodegradable materials). In some variations, each of the liner layers is formed from a dispersible material. In some variations where the body liner comprises one or more adhesive regions, one or more adhesives of the adhesive regions may be the only non-biodegradable component of the body liner. In these variations, the size and placement of adhesive regions may be configured so as to not interfere with the flushability of the body liners.

When a body liner is configured to be flushable, the body liner is preferably made using materials that facilitate or otherwise promote dissolution of the product when disposed in a toilet. For example, in variation where a body liner comprises two or more liner layers that may be at least partially bonded together, as will be described in more detail below, the liner layers may be bonded using one or more water-soluble resins. The liner layers of the flushable body liners are preferably made of cellulosic materials, such as one or more woven or nonwoven materials formed using cellulosic fibers. These cellulosic materials need not include long synthetic fibers, which may promote dispersibility of the body liner. For example, in variations where a body liner comprises a combination of a top sheet, a core member, and/or a back sheet such as those described above, each of the liner layers may be formed from one or more cellulosic materials. Because the body liners are typically removed shortly after soiling, the body liner may be removed prior to significant dissolution of the dissolvable or dispersible body liner components. When the body liner is packaged with one or more release liners, it should be appreciated that the release liner need not be flushable, although the release liner may also be flushable.

It may also be desirable to minimize the overall size of a body liner to facilitate flushing of the body liner. By placing a target point (and in some instances a target zone) of the body liner at or near the anal opening, the body liner may trap ABL loads near the anal opening, which may allow the overall bulk of the body liners to be reduced relative to panty liners, diapers, and the like. Additionally, in some variations, the body liners may be impregnated with one or more absorbent materials (e.g., one or more super-absorbent polymers) which may allow for increased absorption by the body liner without significantly increasing the overall bulk of body liner. In these variations, any liner layer or liner layers (e.g., a top sheet, a back sheet, a core member, combinations thereof, or the like) may be impregnated with these polymers. It should be appreciated, however, that the body liner described here may be able to immobilize and/or absorb a load of anal leakage without the need for super absorbent polymers. Furthermore, in variations of the body liners described here that do not include a fluid-impermeable layer, the absence of a fluid-impermeable layer may reduce the size of the body liners (and also may remove the flushing liability that may occur due to the layer's fluid impermeability).

Multi-Ply Construction

When the body liners described here comprise a plurality of liner layers, some or all of the plurality of liner layers may be connected in any suitable manner. The layers may be formed individually from the respective raw materials for each layer. For example, in some variations, a top sheet layer may be formed from an airlaid non-woven material having a high loft and softness, a core member layer may be formed from a wet-laid non-woven material, and a back sheet may be formed from a hydroentangled non-woven material. The individual layers of the body liner may be placed in contact with each other, and may be connected in one or more manners. For example, two core layers may be bonded together using one or more adhesives. Additionally or alternatively, two layers may be mechanically connected.

When two liners layers are connected using one or more adhesives, one or more adhesives may be applied to one or both of the liner layers and the liner layers may be placed into contact with each other such that the one or more adhesive joins the liner layers. The adhesive may be any suitable adhesive (e.g., one or more hot melt adhesives such as DEMRA-TAK H 542B, Henkel EASYMELT® 34-375C, one or more solvent-based adhesives, one or more water-based adhesives, one or more energy-, heat-, or chemically-cured adhesives, combinations thereof and the like) and may be applied in any suitable manner (e.g., spray application, slot die coating, or the like). Rolling drums, one or more presses, or the like may be used to apply pressure to the liner layers. In some instances, these devices may be heated or cooled to help control the adhesive properties.

When the two layers are mechanically connected, they may be connected in any suitable manner, such as, for example, sewing, embossing, crimping, ultrasonic bonding, thermal bonding, needle punching, entanglement (e.g., fluid entanglement), or the like. For example, in some instances, two or more layers may be joined via entanglement. In these instances, a needle or other penetrating mechanism (e.g., a high pressure air or water stream) may penetrate through the liner layers to entangle fibers of the liner layers. Additionally or alternatively, the penetration mechanism may drive one or more long fibers through the liner layers to mechanically tie the liner layers together.

For example, in some variations where the body liner comprises a top sheet and a core member in contact with the top sheet, such as described in more detail below, the core member may be connected directly to the top sheet. In some variations, the core member may be bonded to the top sheet using one or more adhesives. For example, in some variations, the core member may be bonded to the top sheet using a water soluble resin. Additionally or alternatively, the core member may be mechanically connected to the top sheet, such as described in more detail above.

In variations where a body liner further comprises a core member and a back sheet in contact with the core member, the core member may be attached to the back sheet in any manner such as described immediately above. In variations where a body liner comprises a top sheet, a back sheet, and a core member positioned between the top sheet and the back sheet, any or all of the liner layers may be joined together in any suitable manner such as those described above (e.g., adhesive bonding and/or mechanical connection). For example, in some of these variations, the top sheet and back sheet may be directly connected, and the core member may be attached to one or both of the top sheet and back sheet.

When the core member is enclosed between a top sheet and a back sheet, the core member need not be directly attached to either the top sheet or the back sheet. In these variations, the top sheet and the back sheet may be connected to enclose and retain the core member in between the top sheet and back sheet. It may still be desirable for the core member to be attached to the top sheet and/or back sheet to help prevent relative movement between the core member and the top and back sheets. In these instances, only a small portion of the core member need be attached to the top sheet and/or the back sheet. For example, in some variations, the core member may be directly connected to the back sheet (e.g., using adhesive bonding and/or mechanical connection) such that less than about 15% of the surface area of the core member may be attached to the back sheet. Additionally or alternatively, the core member may be directly connected to the top sheet (e.g., using adhesive bonding and/or mechanical connection) such that less than about 15% of the surface area of the core member may be attached to the top sheet.

In variations where a body liner comprises a back sheet and a top sheet (and, in some variations, a core member positioned therebetween), the back sheet and the top sheet may be directly connected and/or indirectly connected (e.g., connected via a common attachment to a liner layer such as a core member). In some instances, it may be desirable for the back sheet and the top sheet to be substantially unconnected. For example, friction between folded-over rear surfaces may cause the body liner to slip relative to skin of the buttocks during movement, which may result in bunching or displacement of the body liner, as described in more detail above. When the top sheet and back sheet are largely unconnected, the top sheet may be able to slip relative to the back sheet during wearer movement, and this movement may help prevent dislodgement and/or bunching of the body liner (especially in variations where the rear surface of the body liner has a low coefficient of friction). Additionally, adhesive bonding between liner layers may interfere with the ability of the body liner to absorb fluid, may affect the flushability of the liner layer, and/or may increase the stiffness of the body liner (which may decrease the level of comfort provided by the body liner). Accordingly, it may be desirable to join liner layers while minimizing the proportion of the surface area of the liner layers that are connected. In some variations, the top sheet and the back sheet may be connected such that at least 80 percent of surface areas of the top sheet and back sheet remain unconnected. In some of these variations, at least 90 percent of the surface areas of the top sheet and the back sheet remain unconnected.

When the back sheet and top sheet are directly connected, they may be connected in any suitable manner such as described in more detail above (e.g., via adhesive bonding and/or mechanical attachment). In some variations, the back sheet and the top sheet may be connected around the periphery of the top sheet and/or back sheet. In some of these variations, the back sheet and the top sheet may be connected around the entire periphery of the top sheet and/or back sheet. In variations where the top sheet and the back sheet have the same shape, the top sheet and the back sheet may be joined around the peripheries of both the top sheet and the back sheet. In variations where the top sheet is larger than the back sheet, the top sheet and back sheet may be joined around the periphery of the back sheet, or vice versa.

When multiple layers are joined to form a body liner, the shape of the body liner may be created before or after the liner layers are joined. For example, in some variations the shape of individual liner layers may be set prior to joining the liner layers (e.g., individual liner layers may be cut to the desired shape of the body liner prior to construction of the body liner) or the body liner may be set into a desired shape after the liner layers have been joined (e.g., the multi-layer construction may be cut into the desired body liner shape). Additionally, in some instances (such as described in more detail below), one or more adhesive regions may be applied to the body liner. The body liner or individual liner layers may be cut in any suitable manner, such as die cutting, laser cutting, water jet cutting, or the like.

Absorption

As mentioned above, the body liners described here may be configured to be fluid absorbent. The body liners described here may be able to absorb any suitable amount of fluid, depending on the size and materials of the body liners. In some variations, a body liner may have an overall absorbency index of at least about 1.25 g/g. When fluid is absorbed by the body liner, the absorbent material may be configured acquire, distribute, and store fluid absorbed by the liner (e.g., via porosity and/or capillarity of the materials). In some variations, at least a portion of the body liner may be configured to be absorbent such that is may pass body fluid from a body-facing surface to an opposite-facing rear surface of the body liner. In these variations, the body liner may be configured to wick or otherwise transfer fluid via rear surface-to-rear surface contact between body liner portions of different sides of a fold line (such as when folded along a longitudinal axis such as described in more detail above), such as when the rear surfaces of body liner include absorbent materials. When the body liners described here comprise a plurality of liner layers (e.g., a top sheet and a back sheet and/or core member), some or all of the liner layers may be configured to be fluid absorbent. In some variations, each of the liner layers may be configured to be fluid absorbent. In these variations, the body liner may be able to transfer fluid from a body-facing surface through the plurality of liner layers and to a rear surface of the body liner (e.g., each liner layer may be able to transfer fluid from a body-facing side of the liner layer to a rear side of the liner layer). Additionally, the absorbent nature of the body liner (and the liner layers thereof) may allow for gas to pass therethrough, which may thereby provide breathability of the body liner and reduce of moisture by the body liner.

Figure 2A:
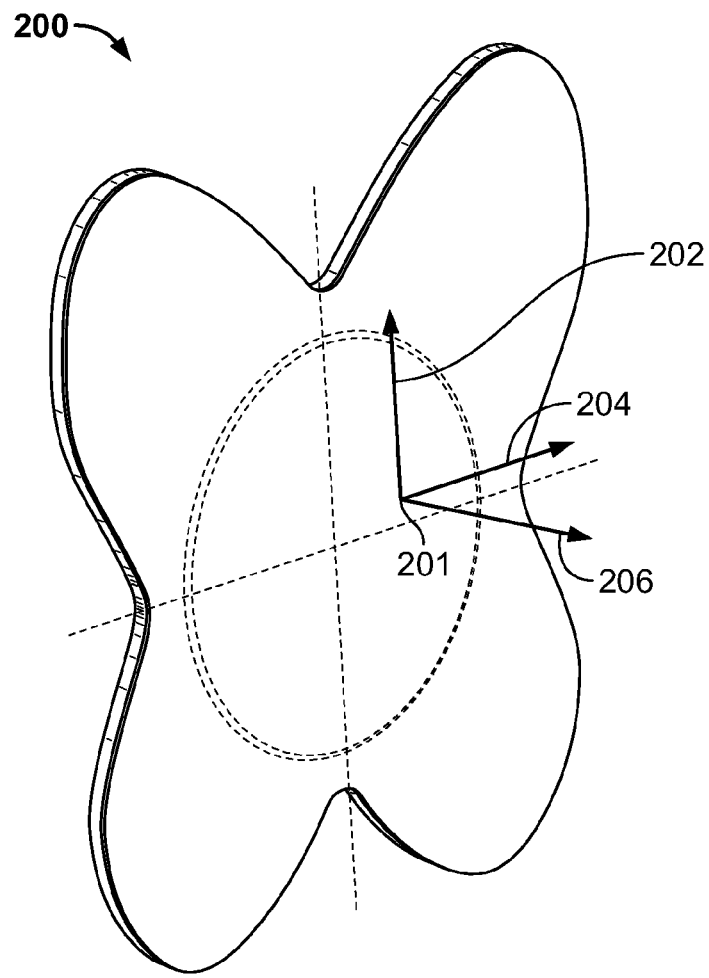
FIG. 2A depicts a side view of an illustrative variation of the body liners described here.

In some variations above, it may be desirable to configure the body liner to selectively distribute fluid absorbed by the body liner. Specifically, the body liner may be configured to have different fluid wicking rates in different directions. FIG. 2A shows a perspective view of an illustrative variation of a body liner (200). The body liner (200) may be any of the body liners described hereinthroughout, and may have any suitable size, shape, and configuration of features. As shown in FIG. 2A, movement of fluid at a given point (201) may be divided into three component directions (i.e., a first direction (202), a second direction (204), and a third direction (206)). As shown there, the first (202) and second (204) directions may be perpendicular to each other within the plane of the body liner (200). The third direction (206) may be perpendicular to the plane of the body liner (200) (and may thereby be perpendicular to both the first (202) and second (204) directions) and may extend across the thickness of the body liner (200). The body liners described here may be configured to selectively control the rate of fluid movement in the first, second, and third directions.

For example, in some variations, it may be desirable to configure a body liner (or one or more liner layers of a body liner) such that fluid moves more quickly through the thickness of a body liner (or liner layer thereof) than it does within the plane of the body liner (or liner layer thereof). For example, in the illustrative variation of the body liner (200) shown in FIG. 2A, the body liner (200) may have a wicking rate in the third direction (206) that is greater than wicking rates in the first (202) and second (204) directions. In these instances, fluid that contacts the body liner (e.g., from a load of bowel leakage) may pass more quickly through the body liner (e.g., from a skin-facing surface of the body liner toward a rear surface of the body liner) than it spreads across the body liner. This may promote absorption across the thickness of the body liner and may reduce the spreading of the fluid load when applied to the body liner. Reducing spread of the fluid absorbed by the body liner may reduce the likelihood that fluid will reach the exterior portion of the body liner, thereby reducing the likelihood that a wearer will touch a soiled portion of the body liner when removing the body liner.

Figure 2B:
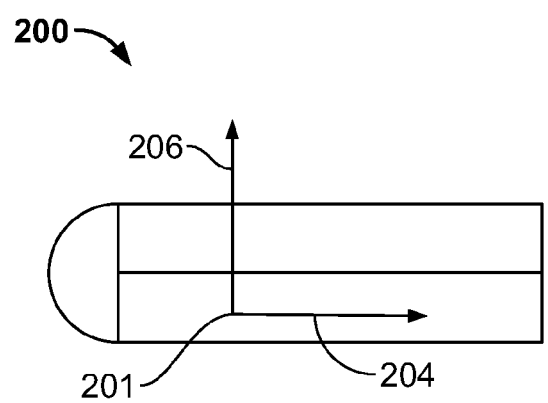
FIG. 2B depicts a front view of the body liner of FIG. 2A.

Additionally, when the body liner is substantially folded back on itself (e.g., folded along the longitudinal axis when placed at least partially in the intergluteal cleft), the fluid that contacts the body liner on one side of the fold line may be transferred through the thickness of body liner and may be further transferred to a portion of the body liner on the other side of the fold (e.g., via the rear surface-to-rear surface contact). For example, FIG. 2B shows a front view of the body liner (200) shown in FIG. 2A, in which the body liner (200) has been folded in half along a longitudinal axis (not shown). As shown there, fluid passing in the third direction (206) relative to point (201) will move toward the opposite half of the body liner along the third direction (206), and may be absorbed by the opposite half of the body liner along the third direction (206). This may increase the overall amount of fluid that is absorbed in the third direction (206), which may further reduce the amount of fluid that may spreads in the first (202) and second (204) directions for a given fluid load. This may help to localize fluid relative to its initial contact point, which is typically close to the anus. When one or more portions of the body liner extends at least partially out of the intergluteal cleft, this localization may reduce the likelihood that fluid reaches the exposed portion or portions of the body liner.

In some variations it may be desirable to configure the body liner (or a liner layer thereof) to transfer fluid at different rates within the plane of the body liner (or liner layer thereof). For example, in variations where the body liner comprises one or more air-laid non-woven materials, the fibers of the material may be laid such that fibers are more aligned in a first direction than a second direction. For example, in the illustrative variation of the body liner (200) shown in FIGS. 2A and 2B, a wicking rate in the first direction (202) may be greater than a wicking rate in the second direction (204) (or vice versa). In these variations, a fluid load applied to the body liner (200) may spread more in the first direction (202) than in the second direction (204). This may find particular utility in instances where one or more portions of a body liner extend beyond the intergluteal cleft to act as a retrieval portion which the wearer can grasp and pull to remove the body liner from the intergluteal cleft. In these variations, it may be desirable to minimize the likelihood that fluid reaches the retrieval portions of the body liners. For example, in the variation of the body liner (100) described above with respect to FIGS. 1A-1E, the body liner (100) may be configured such that at least a portion of one or more of these lobes (116) may extend at least partially from the intergluteal cleft when the body liner (100) is placed at least partially within the intergluteal cleft. These exposed portions of the lobes (116) are positioned either above or below the lateral axis (108). Accordingly, in these variations, it may be desirable to configure the body liner (100) such that a wicking rate in a direction parallel to lateral axis (108) is greater than a wicking rate in a direction parallel to the longitudinal axis (106). In these variations, when a load of anal leakage contacts the body liner (e.g., in the target zone (112)), fluid from the load may spread across the width of the body liner faster than it spreads along the length of the body liner. Accordingly, a smaller amount of fluid may spread along the longitudinal axis toward the lobes (116), which may decrease the likelihood that fluid will be able to travel far enough to reach the exposed portions of the lobes (116).

When the body liners described here are configured to have a wicking rate in a first direction within a plane of the body liner (e.g., first direction (202) of body liner (200)) that is greater than a wicking rate in a second direction within a plane of the body liner (e.g., second direction (204) of the body liner (200)), the first and second directions may be any suitable direction in the body liner. For example, in some of the variations, the first direction may be parallel to the longitudinal axis and the second direction may be parallel to the lateral axis (e.g., fluid may travel along the longitudinal axis faster than it travels along the lateral axis). In others of these variations, the first direction may be parallel to the lateral axis, and the second direction may be parallel to the longitudinal axis (e.g., fluid may travel along the lateral axis faster than it travels along the longitudinal axis). In still others of these variations, the first direction may be angled relative to the longitudinal axis. In these variations, the angle between the first direction and the longitudinal axis may be any suitable angle (e.g., about 30 degrees, about 45 degrees, about 60 degrees, or the like). Because the first and second directions are perpendicular to each other, the angle between the second direction and the lateral axis may be the same as the angle between the first direction and the longitudinal axis.

When the body liners described here are configured to have a wicking rate in a first direction within a plane of the body liner (e.g., first direction (202) of body liner (200)) that is greater than a wicking rate in a second direction within a plane of the body liner (e.g., second direction (204) of the body liner (200)), the wicking rate across the thickness of the body liner (e.g., third direction (204) of the body liner (200)) may be any suitable value relative to the wicking rates in the first and second directions. For example, in some variations, the wicking rate in the third direction may be greater than the wicking rates of both the first and second directions, such as described in more detail above. In other variations, the wicking rate in the third direction may be approximately equal to the wicking rate in the first direction. In still other variations, the wicking rate in the third direction may be less than the wicking rate in the first direction, but may be greater than the wicking rate in the second direction. In yet other variations, the wicking rate in the third direction may be approximately equal to the wicking rate in the second direction. In still other variations, the wicking rate in the third direction may be less than the wicking rates in both the first and second directions. It should be appreciated that while described above as having different wicking rates in the first, second, and/or third directions, it should be appreciated that in some variations, a body liner (or a liner layer thereof) may be configured to uniformly distribute absorbed fluid (e.g., the wicking rates in each direction of the body liner are approximately equal).

In variations where the body liner comprises a plurality of layers, any or all of the liner layers may be configured to selectively distribute fluid in any manner as described above. The movement of fluid within each liner layer may be characterized based on wicking rates in three component directions, specifically a first direction in a plane of the body liner, a second direction in a plane of the body liner that is perpendicular to the first direction, and a third direction extending through the thickness of the body liner and perpendicular to both the first and second directions, such as described above. The wicking rate for a given direction in one liner layer may be the same as or different from the wicking rate for that direction in another liner layer.

For example, in some variations where a body liner comprises a top sheet, the top sheet may be configured to have a wicking rate in the top sheet in the third direction that is greater than a wicking rate in the top sheet in the first direction and greater than a wicking rate in the top sheet in the second direction. In these variations, fluid may be transferred across the thickness of the top sheet more quickly than it spreads across the body liner, which may allow for effective transfer of fluid from the top sheet to one or more additional liner layers (e.g., a core member and/or a back sheet). In some of these variations the wicking rate in the first direction may be greater than the wicking rate in the second direction, or vice versa. In others of these variations, the wicking rate in the first direction may be equal to wicking rate in the second direction.

In other variations, the top sheet may be configured to have a wicking rate in the top sheet in the third direction that is less than a wicking rate in the top sheet in the first direction and less than a wicking rate in the top sheet in the second direction. In these variations, absorbed fluid may spread across the top sheet faster than it is transferred across the thickness of the top sheet. In some of these variations the wicking rate in the first direction may be greater than the wicking rate in the second direction, or vice versa. In others of these variations, the wicking rate in the first direction may be equal to wicking rate in the second direction.

In still other variations the top sheet may be configured to have a wicking rate in the top sheet in a third direction that is less than a wicking rate in the top sheet in a first direction and greater than a wicking rate in the top sheet in a second direction. In yet other variations, the top sheet may be configured to have a wicking rate in the top sheet in a third direction that is equal to the wicking rate in the top sheet in the first direction. In some of these variations, the top sheet may be configured such that a wicking rate in the top sheet in the second direction is greater than the wicking rates in the first and third directions. In others of these variations, the top sheet may be configured such that a wicking rate in the top sheet in the second direction is less than the wicking rates in the first and third directions. In still other variations, the top sheet may be configured to uniformly distribute fluid within the top sheet (i.e., the top sheet may be configured such that a wicking rate in the top sheet in the third direction is equal to a wicking rate in the top sheet in the first direction and a wicking rate in the top sheet in a second direction).

In some variations where a body liner comprises a core member, the core member may be configured to have a wicking rate in the core member in the third direction that is greater than a wicking rate in the core member in the first direction and greater than a wicking rate in the core member in the second direction (which may prioritize absorption through the thickness of the core member over spreading of the fluid sample across the core member, such as discussed above). In some of these variations the wicking rate in the first direction may be greater than the wicking rate in the second direction, or vice versa. In others of these variations, the wicking rate in the first direction may be equal to wicking rate in the second direction.

In other variations, the core member may be configured to have a wicking rate in the core member in the third direction that is less than a wicking rate in the core member in the first direction and less than a wicking rate in the core member in the second direction (which may prioritize spread of the fluid over absorption across the thickness of the core member). In some of these variations the wicking rate in the first direction may be greater than the wicking rate in the second direction, or vice versa. In others of these variations, the wicking rate in the first direction may be the same as the wicking rate in the second direction.

In still other variations the core member may be configured to have a wicking rate in the core member in a third direction that is less than a wicking rate in the core member in a first direction and greater than a wicking rate in the core member in a second direction. In yet other variations, the core member may be configured to have a wicking rate in the core member in a third direction that is equal to the wicking rate in the core member in the first direction. In some of these variations, the core member may be configured such that a wicking rate in the core member in the second direction is greater than the wicking rates in the first and third directions. In others of these variations, the core member may be configured such that a wicking rate in the core member in the second direction is less than the wicking rates in the first and third directions. In still other variations, the core member may be configured to evenly distribute fluid (e.g., may be configured such that a wicking rate in the core member in the third direction is equal to that a wicking rate in the core member in the first direction and a wicking rate in the core member in a second direction).

In some variations where a body liner comprises a back sheet, the back sheet may be configured to have a wicking rate in the back sheet in the third direction that is greater than a wicking rate in the back sheet in the first direction and greater than a wicking rate in the back sheet in the second direction (which may prioritize absorption through the thickness of the back sheet over spreading of the fluid sample across the core member, such as discussed above). In some of these variations the wicking rate in the first direction may be greater than the wicking rate in the second direction, or vice versa. In others of these variations, the wicking rate in the first direction may be the same as the wicking rate in the second direction.

In other variations, the back sheet may be configured to have a wicking rate in the back sheet in the third direction that is less than a wicking rate in the back sheet in the first direction and less than a wicking rate in the back sheet in the second direction (which may prioritize spread of the fluid across the back sheet over absorption through the thickness of the back sheet). In some of these variations, the wicking rate in the first direction may be greater than the wicking rate in the second direction, or vice versa. In others of these variations, the wicking rate in the first direction may be equal to wicking rate in the second direction.

In still other variations the back sheet may be configured to have a wicking rate in the back sheet in a third direction that is less than a wicking rate in the back sheet in a first direction and greater than a wicking rate in the back sheet in a second direction. In yet other variations, the back sheet may be configured to have a wicking rate in the back sheet in a third direction that is the same as the wicking rate in the back sheet in the first direction. In some of these variations, the back sheet may be configured such that a wicking rate in the back sheet in the second direction is greater than the wicking rates in the first and third directions. In others of these variations, the back sheet may be configured such that a wicking rate in the back sheet in the second direction is less than the wicking rates in the first and third directions. In still other variations, the back sheet may be configured to evenly distribute fluid (e.g., may be configured such that a wicking rate in the back sheet in the third direction is equal to that a wicking rate in the back sheet in the first direction and a wicking rate in the back sheet in a second direction.

When the body liners described here comprise a plurality of liner layers (e.g., a top sheet and a core member, a top sheet and a back sheet, or a top sheet, a core member, and a back sheet), the liner layers may be configured to transfer fluid in any combination of manners described above. For example, in some variations where a body liner comprises a top sheet, a back sheet, and a core member, the top sheet may be configured to have a wicking rate in the top sheet in the third direction that is greater than a wicking rate in the top sheet in the first direction and greater than a wicking rate in the top sheet in the second direction. Similarly, the back sheet may be configured to have a wicking rate in the back sheet in the third direction that is greater than a wicking rate in the back sheet in the first direction and greater than a wicking rate in the back sheet in the second direction. In some of these variations, both the top sheet and the back sheet may be configured to have wicking rates in the top sheet and back sheet, respectively, in the first direction that are greater than the wicking rates in the top sheet and back sheet, respectively, in the second direction. In others of these variations, the top sheet may be configured to have a greater wicking rate in the top sheet in the first direction than a wicking rate in the second direction and the back sheet may be configured to distribute fluidly evenly between the first and second directions, or vice versa. The core member may be configured to distribute fluid evenly within the core (e.g., the core member may be configured to have equal wicking rates in each of the first, second, and third directions) or may be configured to selectively transfer fluid such as described in more detail above. In some variations, the core member may be configured to have a wicking rate in the core member in the third direction that is greater than a wicking rate in the core member in the first direction and greater than a wicking rate in the core member in the second direction. The wicking rates in a given direction (e.g., in the third direction) in each of the top sheet, back sheet, and core member may all be the same, or may be different.

In some instances, it may be desirable to configure the body liners described here such that fluid spreads faster in the body liner (i.e., within the plane of the body liner, in the first and second directions as described above) near the rear surface than it spreads near the body-facing surface. In these instances, when an ABL load contacts and is absorbed by the body liner, a larger portion of the fluid load will be absorbed and retained near the rear surface of the body liner. The absorbed bowel leakage may be more concentrated toward the rear surface of the body liner (which is folded over itself) and may result in a smaller visible soiled "spot" on the body-facing surface of the body liner, which may provide the wearer with an additional sense of security and reduce the likelihood that fecal matter absorbed by the body liner may rub off against the skin during removal of the body liner. In variations where the body liner comprises a single liner layer, the liner layer may be configured to spread fluid in the plane of the liner layer faster toward the rear surface than it spreads fluid near the body-facing surface. For example, the liner layer is formed from one or more non-woven materials, the fibers of the liner layer may have a higher distribution of horizontally-oriented fibers near the rear surface than near the body-facing surface, which promote spreading near the rear surface. In variations where the body liner comprises a plurality of liner layers, different liner layers may be configured to spread fluid at different rates. For example, in variations where the body liner comprises a top sheet, a core member, and optionally a back sheet, the core member may be configured to spread fluid in the plane of the body liner faster than the top sheet spreads fluid in the plane of the body liner. In variations where the body liner comprises a back sheet, the back sheet may be configured to spread fluid in the plane of the body liner faster than the top sheet and/or core member spreads fluid.

Body Liner Shape

The body liners described here may have any suitable shape, such as, for example, a circular or oval shape, a rectangular shape, a triangular shape, an hourglass shape, a lobed shape (e.g., a butterfly shape), an irregular shape, combinations thereof and the like. It should be appreciated that regardless of the shape of the body liner, the body liner may be configured to have any combination of features and liner layers described hereinthroughout. The overall shape of the body liner may be a factor of the shape of some or all of the liner layers. For example, in variations where a body liner comprises a single liner layer, the shape of the body liner may be the same as the shape of the single liner layer. In variations where a body liner comprises a plurality of liner layers, the shape of the body liner may be dependent on how the individual liner layers are positioned with respect to each other. For example, in some instances the largest liner layer may define the overall shape of the body liner. In other instances where two or more liner layers partially overlap, the overall shape of the body liner may be defined by the two or more liner layers.

Figure 3A:
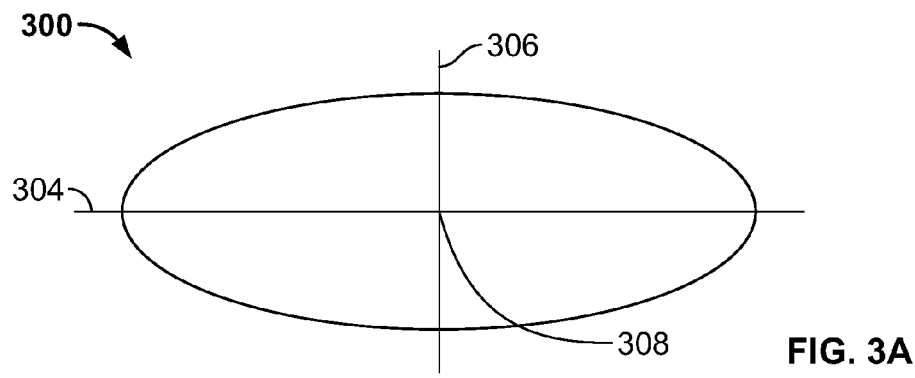
FIG. 3A depicts a top view of one variation of the body liners described here.

As mentioned above, in some variations, the body liners may have a circular or oval shape. For example, FIGS. 3A-3E depict variations of a body liner having an oval shape. Specifically, FIG. 3A shows a top view of body liner (300) having an oval shape. As shown there, body liner (300) may have a longitudinal axis (306) and a lateral axis (304) perpendicular to the longitudinal axis (306) and intersecting the longitudinal axis (306) at a target point (308). When the body liner (300) is placed at least partially within the intergluteal cleft the body liner (300) may be folded along the longitudinal axis (306) to position the target point (308) at or near the opening of the anus. While the target point (308) is shown in FIG. 3A as being positioned at the center of the body liner (300), it should be appreciated that the target point (308) may be positioned at any suitable location on the body liner. Additionally, while the longitudinal axis (306) is shown in FIGS. 3A-3E as positioned along the minor axis of the overall oval shape of the body liner (300), it should be appreciated that the longitudinal axis (306) may be positioned along any suitable portion of the body liner. The body liner (300) may comprise one or more adhesive regions (not shown), as will be described in more detail below.

Figure 3B:
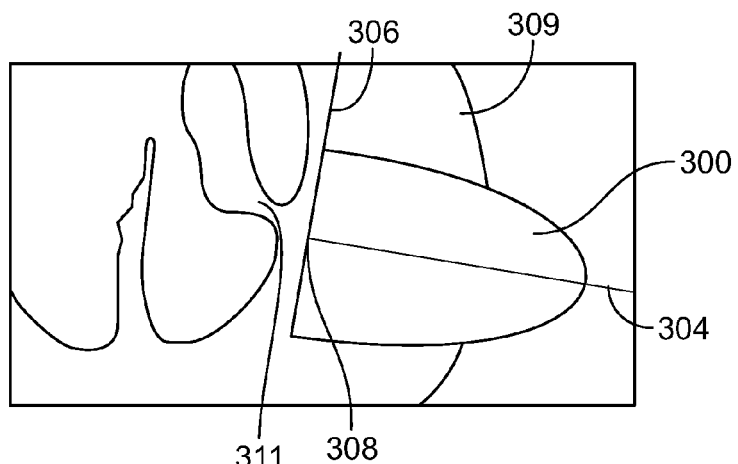
FIG. 3B depicts the body liner of FIG. 3A placed at least partially within the intergluteal cleft.

Generally, the body liner (300) may be sized such that when placed at least partially within the intergluteal cleft, at least a portion of the body liner (300) may extend out of the intergluteal cleft. For example, FIG. 3B shows a cross-sectional side view of a person with the body liner (300) placed partially within the intergluteal cleft (309). As shown there, the body liner (300) may be positioned such that the target point (308) is positioned at or near the anus (311) and the body liner (300) is folded substantially along the longitudinal axis (306). When positioned as shown in FIG. 3B, at least a portion of the body liner (300) extends outside of the intergluteal cleft (309). Generally, the exposed portion of the body liner (300) may extend far enough outside the intergluteal cleft enough to allow a wearer to grasp the body liner (300), but not so far that the body liner (300) is snagged by clothing, such as described in more detail above.

Figure 3C:
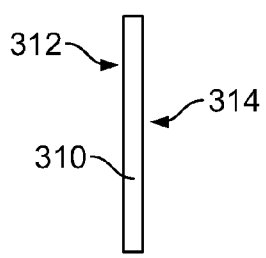
FIGS. 3C-3E depict cross-sectional side views of variations of the body liner shown in FIG. 3A.

The body liner (300) shown in FIGS. 3A and 3B may be made from one or more liner layers. For example, FIG. 3C shows a cross-sectional side view (taken along the longitudinal axis (306)) of a variation of the body liner (300) in which the body liner (300) comprises a single liner layer (310). In these variations, overall oval shape of the body liner (300) may be defined by the oval shape of the liner layer (310). Additionally, a body-facing side of the liner layer (310) may form the body-facing surface (312) of the body liner (300) and an opposite rear side of the liner layer (310) may form the rear surface (314) of the body liner (300). It should be appreciated that the body-facing surface (312) and rear surface (314) of the body liner (300) may be configured to have any respective coefficients of friction, such as described in more detail below.

The liner layer (310) may be configured to absorb fluid, such as described in more detail above. In some variations, the liner layer (310) may be configured to selectively transfer fluid as described above. For example, in some variations, the liner layer (310) may be configured to transfer fluid across the thickness of a body liner (e.g., in a "third direction" as discussed above, which may perpendicular to both the longitudinal axis (306) and the lateral axis (304)) at a wicking rate that is greater than wicking rates at which fluid is transferred within the plane of the body liner (e.g., in a "first direction" and "second direction" as discussed above). When the body liner (300) is folded over the longitudinal axis (306), a greater wicking rate across the thickness of the body liner (300) may promote transfer of fluid from a contact point on the body-facing surface (312) of the body liner on one side of the fold to the rear surface (314) on that side of the fold, and may further promote transfer from the rear surface (314) to a contacting rear surface (314) on the opposite side of the fold, as described in more detail above. Additionally or alternatively, the liner layer (310) may be configured to transfer fluid in a first direction in the plane of the body liner (300) at a wicking rate that is faster than the wicking rate in a second direction in the plane of the body liner (300) that is perpendicular to the first direction. For example, in some variations, the liner layer (310) may be configured to transfer fluid in a first direction parallel to the longitudinal axis (306) at a wicking rate that is faster than a wicking rate in a second direction parallel to the lateral axis (304). When the body liner (300) is placed at least partially in the intergluteal cleft as shown in FIG. 3B, fluid absorbed by the body liner (300) must travel parallel to the lateral axis (304) in order to reach the portions of the body liner (300) extending from the intergluteal cleft. Accordingly, having a faster wicking rate along the longitudinal axis (306) than a wicking rate along the lateral axis (304) may reduce the amount of fluid that the liner layer (302) transmits along the lateral axis (304) toward the portion of the exposed portions of the body liner (300), which may help prevent the wearer from grabbing a soiled portion of the body liner (300) during removal of the body liner.

Figure 3D:
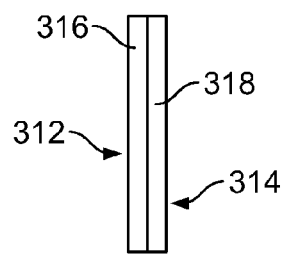

In other variations, the body liners described here may comprise two or more liner layers. For example, FIG. 3D shows a variation of body liner (300) in which the body liner is formed from a top sheet (316) and a core member (318) in contact with the top sheet (316). In some variations, the top sheet (316) and core member (318) may be the only liner layers of the body liner (300). The top sheet (316) and core member (318) may be any combination of top sheet and core member, such as those described in more detail above. In these variations, the top sheet (316) and core member (318) may have the same oval shape, which may be the overall shape of the body liner (300). As shown in FIG. 3D, a body-facing side of the top sheet (316) may form the body-facing surface (312) of the body liner (300) and a rear side of the core member may form the rear surface (314) of the body liner (300).

The top sheet (316) and/or core member (318) may be configured to be fluid absorbent, such as described in more detail above. In some variations, both the top sheet (316) and the core member (318) are configured to be fluid absorbent. In some variations, one or both of the top sheet (316) and core member (318) may be configured to selectively transfer fluid within the respective liner layers, such as described above. For example, in some variations, the top sheet (316) may be configured to transfer fluid across the thickness of a top sheet (316) (e.g., in a "third direction", which may be perpendicular to both the longitudinal axis (306) and the lateral axis (304)) at a wicking rate that is greater than wicking rates at which fluid is transferred within the plane of the top sheet (e.g., in a "first direction" and "second direction" as discussed above). This may promote transfer of fluid through the thickness of the top sheet (316) and into the core member (318). In some of these variations, the core member (318) may be configured to transfer fluid across the thickness of a core member (318) at a wicking rate that is greater than wicking rates at which fluid is transferred within the plane of the core member (318). When the body liner (300) is folded over the longitudinal axis (306), a greater wicking rate across the thickness of the core member (318) may promote transfer of fluid from between portions of the rear surface (314) on either side of the fold via rear surface-to-rear surface contact. In other variations, the core member (318) may be configured to distribute fluid evenly through the core member (318).

In some variations, the top sheet (316) may be configured to transfer fluid in a direction parallel to the longitudinal axis (306) at a wicking rate that is faster than a wicking rate in a direction parallel to the lateral axis (304). In these variations, fluid absorbed by the top sheet (316) may be less likely to reach portions of the body liner (300) extending from the intergluteal cleft, such as described above. Additionally or alternatively, the core member (318) may be configured to transfer fluid in a direction parallel to the longitudinal axis (306) at a wicking rate that is faster than a wicking rate in a direction parallel to the lateral axis (304). In these variations, fluid absorbed by the core member (318) may be less likely to reach portions of the body (300).

Figure 3E:
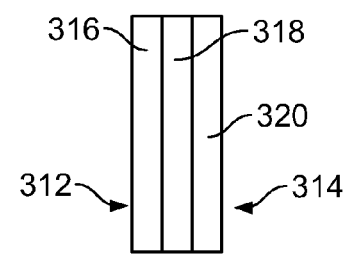

In other variations, the body liner (300) may comprise three or more liner layers. For example, FIG. 3E shows a variation of body liner (300) in which the body liner may be formed from a top sheet (316), a core member (318) in contact with the top sheet (316), and a back sheet (320) in contact with the core member (318). In some variations, the top sheet (316), core member (318), and back sheet (320) may be the only liner layers of the body liner (300). The top sheet (316), core member (318), and back sheet (320) may include any combination of top sheets, core members, and back sheets, such as those described in more detail above. In the variation shown in FIG. 3E, the top sheet (316), core member (318), and back sheet (320) may each have the same oval shape, which may be the same overall size and shape of the body liner (300). As shown there, a body-facing side of the top sheet (316) may form the body-facing surface (312) of the body liner (300) while a rear side of the back sheet (320) may form the rear surface (314) of the body liner (300). It should be appreciated that the body-facing surface (312) and rear surface (314) of the body liner (300) may be configured to have any respective coefficients of friction, such as described in more detail below.

The top sheet (316), core member (318), and/or back sheet (320) may be configured to be fluid absorbent, such as described in more detail above. In some variations, each of the top sheet (316), the core member (318), and back sheet (320) may be configured to be fluid absorbent. Some or all of the top sheet (316), core member (318), and back sheet (320) may be configured to selectively transfer fluid as described above. For example, in some variations, the top sheet (316) may be configured to transfer fluid across the thickness of a top sheet (316) (e.g., in a "third direction", which may be perpendicular to both the longitudinal axis (306) and the lateral axis (304)) at a wicking rate that is greater than wicking rates at which fluid is transferred within the plane of the top sheet (e.g., in a "first direction" and "second direction" as discussed above). This may promote quicker transfer of fluid through the thickness of the top sheet (316) and to the core member (318). In some of these variations, the core member (318) may be configured to transfer fluid across the thickness of a core member (318) at a wicking rate that is greater than a wicking rate or rates at which fluid is transferred within the plane of the core member (318), which may promote quicker transfer of fluid through the thickness of the core member (318) and to the back sheet (320). In some variations, the core member (318) may be configured to distribute fluid absorbed by the core member (318) evenly though the core member. In some variations, the back sheet (320) may also be configured to transfer fluid across the thickness of the back sheet (320) at a wicking rate that is greater than wicking rates at which fluid is transferred within the plane of the back sheet (320). When the body liner (300) is folded over the longitudinal axis (306), a greater wicking rate across the thickness of the back sheet (320) may promote transfer of fluid through the thickness of the back sheet (320) and transfer of fluid to a portion of the back sheet (320) on the opposite side of the fold via back sheet-to-back sheet contact.

In some variations, the top sheet (316) may be configured to transfer fluid in a direction parallel to the longitudinal axis (306) at a wicking rate that is faster than a wicking rate in a direction parallel to the lateral axis (304). Additionally or alternatively, the core member (318) may be configured to transfer fluid in a direction parallel to the longitudinal axis (306) at a wicking rate that is faster than a wicking rate in a direction parallel to the lateral axis (304). Additionally or alternatively, the back sheet (320) may be configured to transfer fluid in a direction parallel to the longitudinal axis (306) at a wicking rate that is faster than a wicking rate in a direction parallel to the lateral axis (304). In these variations, having a faster wicking rate parallel to the longitudinal axis in some or all of the top sheet, back sheet, and core member may reduce the likelihood the absorbed fluid will reach portions of the body liner (300) extending from the intergluteal cleft.

Figure 4A:
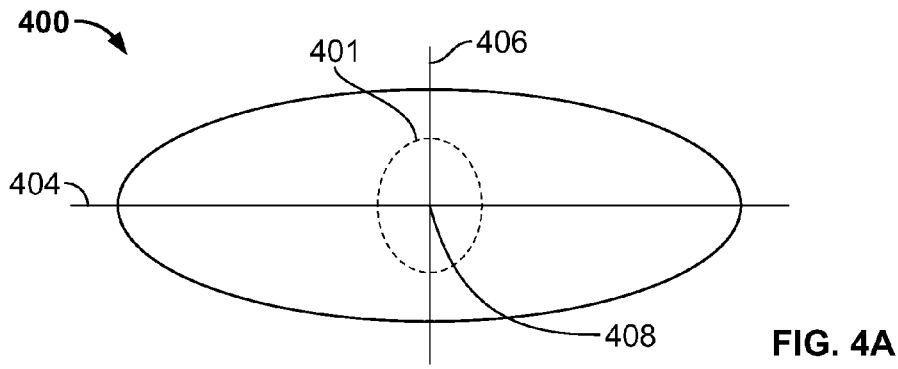
FIGS. 4A and 4E depict top views of variations of the body liners described here.

In some variations, the body liners may comprise a target zone which may have one or more different properties than surrounding portions of the body liner. For example, FIG. 4A shows a top view of body liner (400) having an oval shape and a target zone (401). As shown there, body liner (400) may have a longitudinal axis (406) and a lateral axis (404) perpendicular to the longitudinal axis (406) and intersecting the longitudinal axis (406) at a target point (408). When the body liner (400) is placed at least partially into the intergluteal cleft, such as described above with respect to body liner (300) in FIG. 3B, the body liner (400) may be folded along the longitudinal axis (406) to position the target point (408) at or near the anus. While the target point (408) is shown in FIG. 4A as being positioned at the center of the body liner (400), it should be appreciated that the target point (408) may be positioned at any suitable location on the body liner. Additionally, while the longitudinal axis (406) is shown in FIG. 4A as positioned along the minor axis of the oval, it should be appreciated that the longitudinal axis (406) may be positioned along any suitable portion of the body liner. The body liner (400) may comprise one or more adhesive regions (not shown), as will be described in more detail below.

Generally, the body liner (400) may be sized such that when placed at least partially within the intergluteal cleft, at least a portion of the body liner (400) may extend out of the intergluteal cleft. The body liner (400) may be positioned in the intergluteal cleft such as described above with respect to the body liner (300) shown in FIG. 3B. When so positioned, at least a portion of the body liner (400) may extend outside of the intergluteal cleft. Generally, the exposed portion of the body liner (400) extends far enough outside the intergluteal cleft enough to allow a wearer to grasp the body liner (400), but not so far that the body liner (400) is snagged by clothing, such as described in more detail above.

Figure 4B:
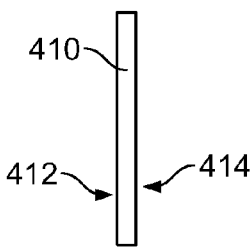
FIGS. 4B-4D depict cross-sectional side views of variations of the body liner shown in FIG. 4A.
Figure 4C:
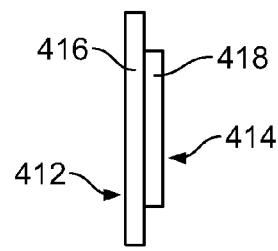
Figure 4D:
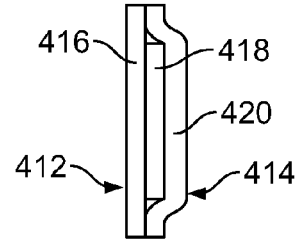
Figure 4E:
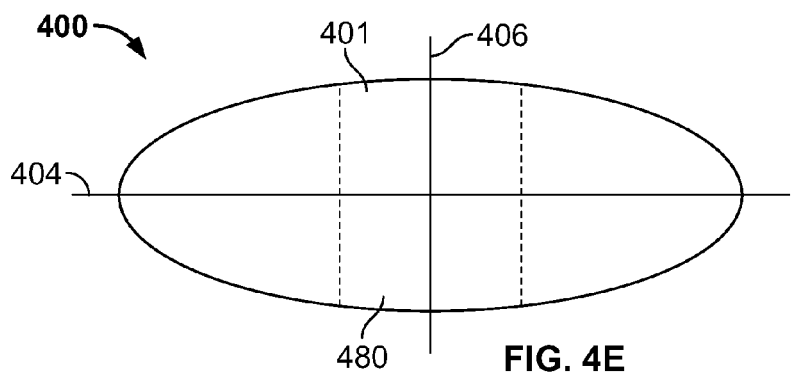

As mentioned previously, the body liner (400) may include a target zone (401). The target zone (401) may at least partially surround the target point (408) and may be configured to receive a load of anal leakage and absorb fluid therefrom. Generally, the target zone (401) may have any suitable size and shape such as described above. While shown in FIG. 4A as being oval in shape, the target zone (401) may have any suitable shape (e.g., a circle shape, a rectangular shape, an irregular shape or the like). When the target zone (401) is oval in shape, a major axis of the oval target zone (401) may be aligned parallel to the longitudinal axis (406). In other variations, the target zone (401) may be positioned such that the major axis of the oval target zone (401) is angled relative to the longitudinal axis (406) (e.g., perpendicular to longitudinal axis (406) or the like). Generally the target zone (401) may be sized such that it may fit entirely within the intergluteal cleft when the body liner (400) is placed as discussed above with respect to the variation of body liner (300) shown above in FIG. 3B. FIG. 4E shows another variation of the body liner (400) in which the target zone (401) is formed as a strip (480) that spans a length of the liner. In the variation shown in FIG. 4E, the strip (480) spans a height of the liner along the longitudinal axis (406), although it should be appreciated that in other instances the strip (480) may span a width of the liner (e.g., along the lateral axis (404)). In instances where the body liner (400) comprises a core member that defines the size and shape of the target zone (401), as will be discussed in detail below, the core member may be sized and shaped as the strip (480) shown in FIG. 4E.

The body liner (400) shown in FIG. 4A may be made from one or more liner layers. For example, FIG. 4B shows a cross-sectional side view (taken along the longitudinal axis (406)) of a variation of the body liner (400) in which the body liner (400) is formed from a single liner layer (410). In these variations, the liner layer (410) may have an oval shape that defines the overall shape of the body liner (400). Additionally, a body-facing side of the liner layer (410) may form the body-facing surface (412) of the body liner (400) and an opposite rear side of the liner layer (410) may form the rear surface (414) of the body liner (400). The body-facing surface (412) and/or rear surface (414) of the body liner (400) may be configured to have any respective coefficients of friction, such as described in more detail below.

The liner layer (410) may be configured to absorb fluid, such as described in more detail above. In some of these variations, the target zone (401) may have a different absorbency than surrounding portions of the body liner (400). In some of these variations, the absorbency of the target zone (401) may be greater than the absorbency of the surrounding portions of the body liner (400). For example, in some variations, the target zone (401) may be formed from a different material than the surrounding portions of the liner layer. Additionally or alternatively, the target zone (401) may be embedded with one or more absorbent materials, such as one or more super absorbent polymers, such as described in more detail above.

In some variations, the liner layer (410) may be configured to selectively transfer fluid, such as described above with respect to the variation of liner layer (310) shown in FIG. 3C. It should be appreciated that a wicking rate in a particular direction in the target zone (401) may be different than a wicking rate in the same direction in surrounding portions of the body liner (400). For example, in some variations the target zone (401) may be configured to transfer fluid within the target zone (401) faster than it is transferred within the surrounding portions of the body liner (400). In these instances, faster wicking within the target zone (401) may cause the target zone (401) to absorb more fluid than the surrounding portions of the body liner (400), which may limit the amount of fluid that may reach the periphery of the body liner (400).

In other variations, the body liners (400) may comprise two or more liner layers. For example, FIG. 4C shows a variation of the body liner (400) in which the body liner may be formed from a top sheet (416) and a core member (418) in contact with and attached to the top sheet (416). In some variations, the top sheet (416) and core member (418) may be the only liner layers of the body liner (400). The top sheet (416) and core member (418) may be any combination of top sheets and core members, such as those described in more detail above. In some of these variations, the top sheet (416) may have an oval shape that defines the overall size and shape of the body liner (400). In some variations, the core member (418) may be the same size and shape as the target zone (401), such that core member (418) may define the overall size and shape of the target zone (401). In these variations, the core member (418) may be any suitable size such as described in more detail above. In the variation shown in FIG. 4C, a body-facing side of the top sheet (416) may form the body-facing surface (412) of the body liner (400). The rear surface (414) of the body liner (400) may be formed from a combination of the rear side of core member (418) and the portion of the rear side of the top sheet (416) that is not covered by the core member (418). The body-facing surface (412) and/or rear surface (414) of the body liner (400) may be configured to have any respective coefficients of friction, such as described in more detail below.

The top sheet (416) and/or core member (418) may be configured to be fluid absorbent, such as described in more detail above. In some variations, both the top sheet (416) and the core member (418) are configured to be fluid absorbent. In these variations, the addition of the core member (418) to the target zone (401) may increase the absorbance of the body liner (400) in the target zone (401) relative to the surrounding portions of the body liner (400). The absorbency of the body liner (400) in the target zone (401) may be further modified by modification of the body liner materials in the target zone (401) and/or inclusion of one or more absorbent materials, such as described immediately above.

In some variations, one or both of the top sheet (416) and core member (418) may be configured to selectively transfer fluid as described in more detail above. For example, the top sheet (416) may be configured to selectively transfer fluid in any manner such as those described above with respect to top sheet (316) depicted in FIG. 3D, while the core member (418) may be configured to selectively transfer fluid in any manner such as those described above with respect to core member (318) depicted in FIG. 3D. In some variations, the core member (418) may be configured to distribute fluid more quickly than the top sheet (416). In these variations, fluid absorbed by the body liner (e.g., through the top sheet (316)) may be distributed more in the core member than the top sheet, which may reduce the likelihood the fluid reaches the periphery of the body liner (400).

In other variations, the body liner (400) may comprise three or more liner layers. For example, FIG. 4D shows a variation of body liner (400) in which the body liner is formed from a top sheet (416), a back sheet (420), and a core member (418) positioned between the top sheet (416) and the back sheet (420). In some variations, the top sheet (416), core member (418), and back sheet (420) may be the only liner layers of the body liner (400). The top sheet (416), core member (418), and back sheet (420) may be any combination of top sheets, core members, and back sheets, such as those described in more detail above. In the variation shown in FIG. 4D, the top sheet (416) and the back sheet (418) may each have the same oval shape, which may define the overall shape of the body liner (400). The core member (418) may be the same size and shape as the target zone (401), such that core member (418) may define the overall size and shape of the target zone (401). As shown in FIG. 4D, a body-facing side of the top sheet (416) may form the body-facing surface (412) of the body liner (400) while a rear side of the back sheet (420) may form the rear surface (414) of the body liner (400). Additionally, a body-facing side of the liner layer (410) may form the body-facing surface (412) of the body liner (400) and an opposite rear side of the liner layer (410) may form the rear surface (414) of the body liner (400). The body-facing surface (412) and/or rear surface (414) of the body liner (400) may be configured to have any respective coefficients of friction, such as described in more detail below.

The top sheet (416), core member (418), and/or back sheet (420) may be configured to be fluid absorbent, such as described in more detail above. In some of these variations, each of the top sheet (416), the core member (418), and back sheet (420) may be configured to be fluid absorbent. In these variations, the addition of the core member (418) to the target zone (401) may increase the absorbance of the body liner (400) in the target zone (401) relative to the surrounding portions of the body liner (400), which may include only the top sheet (416) and the back sheet (420). The absorbency of the body liner (400) in the target zone (401) may be further modified by altering the materials of the liner layers in the target zone (401) and/or inclusion of one or more absorbent materials, such as described immediately above.

In some variations, one, two, or each of the top sheet (416), core member (418), and back sheet (420) may be configured to selectively transfer fluid as described in more detail above. For example, the top sheet (416) may be configured to selectively transfer fluid in any manner such as those described above with respect to top sheet (316) depicted in FIG. 3D, while the core member (418) may be configured to selectively transfer fluid in any manner such as those described above with respect to core member (318) depicted in FIG. 3D, and the back sheet (420) may be configured to selectively transfer fluid in any manner such as those described above with respect to the back sheet (320) depicted in FIG. 3D. In some variations, the core member (418) may be configured to distribute fluid more quickly than the top sheet (416) and the back sheet (420). In these variations, fluid absorbed by the body liner (e.g., through the top sheet (316)) may be distributed more in the core member than the top sheet and back sheet, which may reduce the likelihood the fluid reaches the periphery of the body liner (400) (e.g., by spreading past the target zone (401) into surrounding portions of the body liner (400)).

Figure 5A:
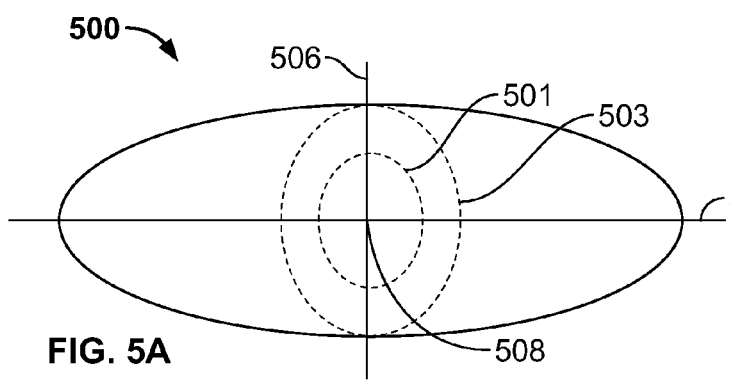
FIG. 5A depicts a top view of one variation of the body liners described here.

While the top sheet (416) and back sheet (420) are shown in FIG. 4C as having the same size and shape, it should be appreciated that the top sheet (416) and back sheet (420) may have a different size and/or shape. For example, FIG. 5A shows a top view of body liner (500) having an overall oval shape and a target zone (501). As shown there, body liner (500) may have a longitudinal axis (506) and a lateral axis (504) perpendicular to the longitudinal axis (506) and intersecting the longitudinal axis (506) at a target point (508). When the body liner (500) is placed at least partially into the intergluteal cleft, such as described above with respect to the body liner (300) depicted in FIG. 3B, the body liner (500) may be folded along the longitudinal axis (506) to position the target point (508) at or near the anus. While the target point (508) is shown in FIG. 5A as being positioned at the center of the body liner (500), it should be appreciated that the target point (508) may be positioned at any suitable location on the body liner. Additionally, while the longitudinal axis (506) is shown in FIG. 5A as positioned along the minor axis of the oval, it should be appreciated that the longitudinal axis (506) may be positioned along any suitable portion of the body liner. The body liner (500) may comprise one or more adhesive regions (not shown), as will be described in more detail below. Generally, the body liner (500) may be sized such that when placed at least partially within the intergluteal cleft, at least a portion of the body liner (500) may extend out of the intergluteal cleft, such as described in more detail above. In some variations, the exposed portion of the body liner (500) extends far enough outside the intergluteal cleft enough to allow a wearer to grasp the body liner (500), but not so far that the body liner (500) is snagged by clothing.

As mentioned above, the body liner (500) may include a target zone (501). The target zone (501) may at least partially surround the target point (508) and may be configured to receive a load of anal leakage and absorb fluid therefrom. Generally, the target zone (901) may have any suitable size and shape such as described above. While shown in FIG. 5A as being oval in shape, the target zone (501) may have any suitable shape (e.g., a circle shape, a rectangular shape, an irregular shape or the like). When the target zone (501) is oval in shape, a major axis of the oval target zone (501) may be aligned parallel to the longitudinal axis (506). In other variations, the target zone (501) may be positioned such that the major axis of the oval target zone (501) is angled relative to the longitudinal axis (506) (e.g., perpendicular to longitudinal axis (506) or the like).

Figure 5B:
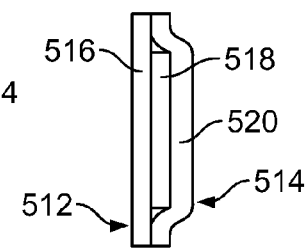
FIG. 5B depicts a cross-sectional side view of the body liner shown in FIG. 5A.

The body liner (500) shown in FIG. 5A may comprise three layers, including a top sheet (516), a core member (518), and a back sheet (520), as shown in a cross-sectional side view (taken along the longitudinal axis (506)) in FIG. 5B. In some variations, the top sheet (516), core member (518), and back sheet (520) may be the only liner layers of the body liner (500). The top sheet (516), core member (518), and back sheet (520) may be any combination of top sheets, core members, and back sheets, such as those described in more detail above. In the variation shown in FIG. 5B, the top sheet (516) have an oval shape, which may define the overall shape of the body liner (500) and the core member (518) may be the same size and shape as the target zone (501), such that core member (518) may define the overall size and shape of the target zone (501). In these variations, the back sheet (520) may have a shape larger than the target zone (501) yet smaller than that of the top sheet (516), such that the back sheet (520) may enclose the core member (518) between the top sheet (516) and the back sheet (520). The back sheet (520) and top sheet (516) may be connected in any suitable manner, such as described in more detail above. In these variations, a body-facing side of the top sheet (516) may form the body-facing surface (512) of the body liner (500). The rear surface (514) of the body liner (500) may be formed by a combination of a rear side of the back sheet (520) and the portions of the rear side of the top sheet (520) which are not covered by the back sheet (520).

The size and shape of the back sheet (520) may define the size and shape of a second zone (503) as indicated in FIG. 5A. While shown in FIG. 5A as being oval, the back sheet (520) (and with it, the second zone (503)) may have any suitable shape (e.g., a circle, a rectangle, an irregular shape, or the like). The second zone (503) may at least partially surround the target zone (501), and may have different properties from the target zone (501) and/or surrounding portions of the body liner (500), as will be described in more detail below.

The top sheet (516), core member (518), and/or back sheet (520) may be configured to be fluid absorbent. In some variations, each of the top sheet (516), the core member (518), and back sheet (520) may be configured to be fluid absorbent. In these variations, the inclusion of the top sheet (516), the core member (518), and the back sheet (520) in the target zone (501) may allow for greater absorbency in the target zone (501) relative to the second zone (503) (which may include just the top sheet (516) and the back sheet (520), which in turn may have greater absorbency than the surrounding portions of the body liner (500) (which may include just the top sheet (516). The absorbency of the body liner (500) in the target zone (501), the second zone (503), and/or the surrounding portions of the body liner may be further modified by modification of the materials in one or more of the liner layers and/or the inclusion of one or more absorbent materials in one or more of the liner layers, such as described in more detail above. It should also be appreciated any or all of the top sheet (516), core member (518), and back sheet (520) may be configured to selectively transfer fluid, and may be configured to do so in any manner or combination of manners as described in more detail above.

Figure 6A:
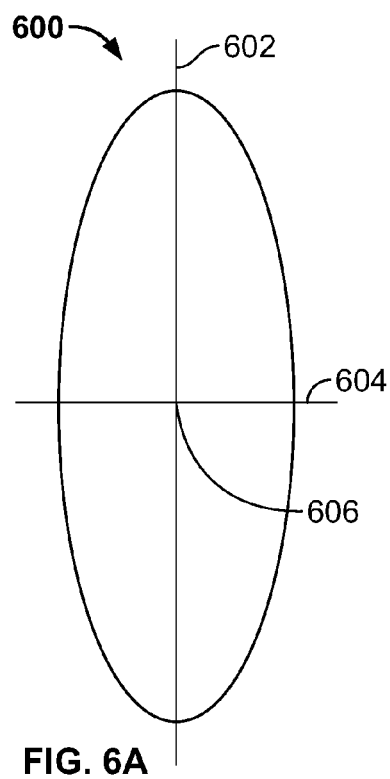
FIG. 6A depicts a top view of a variation of the body liners described here.
Figure 6B:
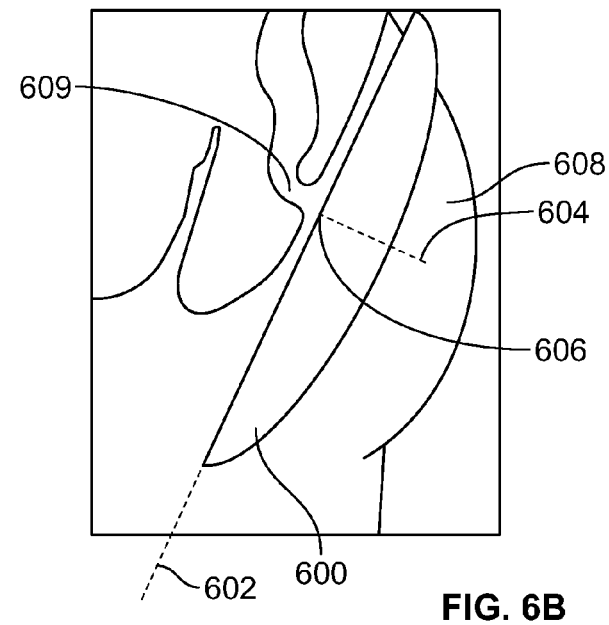
FIG. 6B depicts the body liner of FIG. 6A placed at least partially within the intergluteal cleft.

While the oval body liners depicted in FIGS. 3A-3E, 4A-4D, and 5A and 5B are shown in those figures as having a minor axis of the overall oval shape of the body liner aligned with a longitudinal axis of the body liner, it should be appreciated that in other instances the longitudinal axis may be aligned in any suitable manner relative to the body liner. For example, FIG. 6A a first variation of a body liner (600) having an oval shape, and having a longitudinal axis (602) and lateral axis (604) intersecting the longitudinal axis (602) at a target point (606). As shown there, a major axis of the overall oval shape of the body liner may be aligned with the longitudinal axis (602). The body liner (600) may be include any number of liner layers and may be configured in any suitable manner, such as described above with respect to FIGS. 3A-3E. When the body liner (600) is folded along the longitudinal axis (602)

and placed in the intergluteal cleft (608) to position the target point (606) at or near the anus (609), the body liner (600) may be sized such that a portion of the body liner (600) extends outside of intergluteal cleft (608), as depicted in FIG. 6B. As shown there, the portions of the body liner (600) that extend outside of the intergluteal cleft at one or both ends of the body liner (600) along the longitudinal axis (602). In variations where the body liner (600) (or one or more liner layers thereof) is configured to selectively transfer fluid in the plane of the body liner (600) (or one or more liner layers thereof), it may be desirable to configure the body liner (600) (or one or more liner layers thereof) to transfer fluid along the lateral axis (604) at a faster wicking rate than a wicking rate long the longitudinal axis (602). In these variations, more fluid may be transferred along the lateral axis (604) than the longitudinal axis (606), which may reduce the likelihood that fluid absorbed by the body liner (600) will reach the portions of the body liner (600) extending from the intergluteal cleft.

Figure 6C:
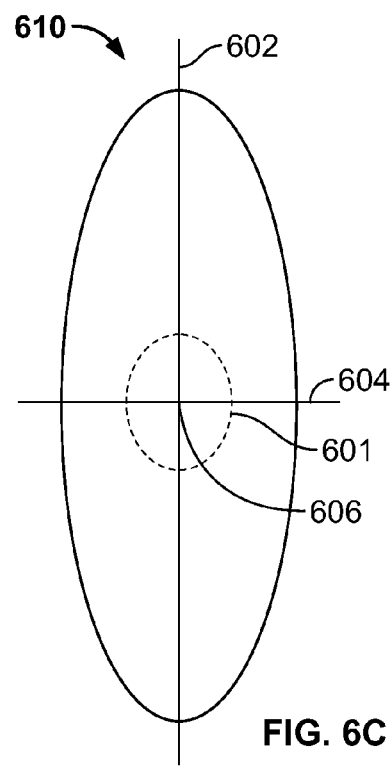
FIGS. 6C and 6D depict top views of variations of the body liners described here.

Similarly, FIG. 6C shows a variation of a body liner (610) having an oval shape and a target zone (601). The body liner may have a longitudinal axis (602) and lateral axis (604) intersecting the longitudinal axis (602) at a target point (606), and may be configured in any suitable manner such as those described above with respect to the variations of the body liner (400) depicted in FIGS. 4A-4D, except that the major axis of the overall oval shape of body liner (610) is aligned with the longitudinal axis (602) (instead of being aligned with the lateral axis, such as shown in FIG. 4A). Again, in these variations, it may be desirable to configure the body liner (600) (or one or more liner layers thereof) to transfer fluid along the lateral axis (604) at a faster wicking rate than a wicking rate long the longitudinal axis (602).

Figure 6D:
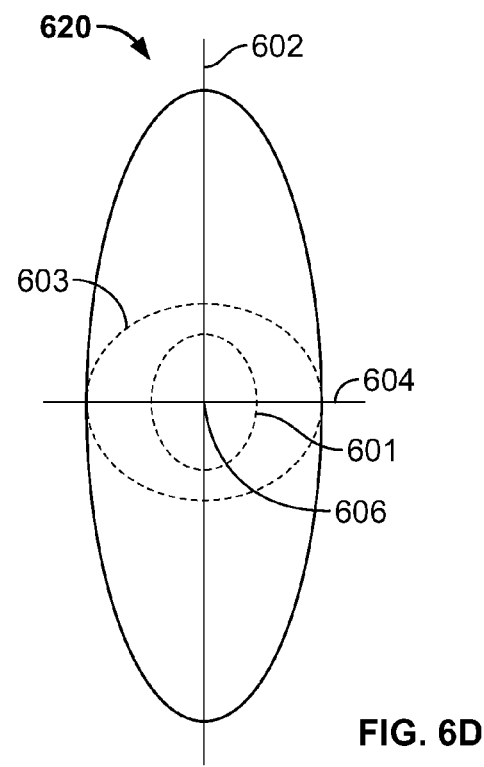

FIG. 6D shows a variation of a body liner (620) having an oval shape and a target zone (601) and a second zone (603). The body liner may have a longitudinal axis (602) and lateral axis (604) intersecting the longitudinal axis (602) at a target point (606), and may be configured in any suitable manner such as those described above with respect to the variations of the body liner (500) depicted in FIGS. 5A-5D, except that the major axis of the overall oval shape of body liner (610) is aligned with the longitudinal axis (602) (instead of being aligned with the lateral axis, such as shown in FIG. 5A). Again, in these variations, it may be desirable to configure the body liner (600) (or one or more liner layers thereof) to transfer fluid along the lateral axis (604) at a faster wicking rate than a wicking rate long the longitudinal axis (602).

Figure 7A:
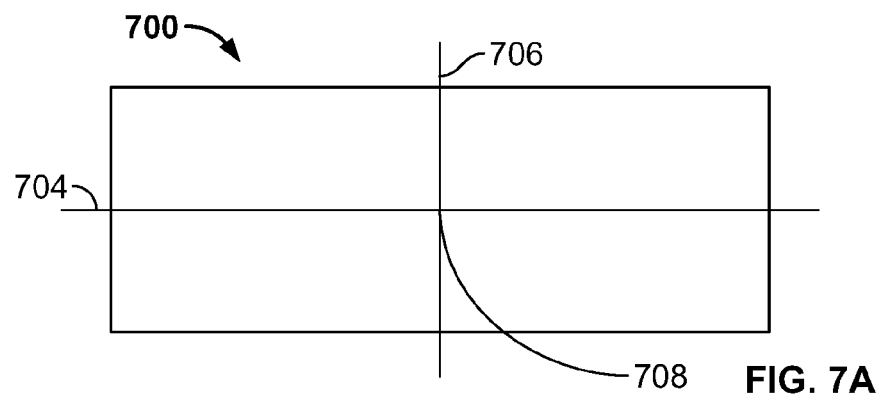
FIG. 7A depicts a top view of one variation of the body liners described here.

As mentioned above, in some variations, the body liners may have a rectangular shape. For example, FIGS. 7A-7E depict variations of a body liner having a rectangular shape. Specifically, FIG. 7A shows a top view of body liner (700) having a rectangular shape. As shown there, body liner (700) may have a longitudinal axis (706) and a lateral axis (704) perpendicular to the longitudinal axis (706) and intersecting the longitudinal axis (706) at a target point (708). When the body liner (700) is placed at least partially into the intergluteal cleft the body liner (700) may be folded along the longitudinal axis (706) to position the target point (708) at or near the opening of the anus. While the target point (708) is shown in FIG. 7A as being positioned at the center of the body liner (700), it should be appreciated that the target point (708) may be positioned at any suitable location on the body liner. Additionally, while the body liner (700) shown in FIGS. 7A-7E as having a height along the longitudinal axis (706) that is less than a width along the lateral axis (704), it should be appreciated that in some instances the body liner (700) may have equal height and width, or may have a width along the lateral axis (704) that is greater than a height along the longitudinal axis (706). The body liner (700) may comprise one or more adhesive regions (not shown), as will be described in more detail below.

Figure 7B:
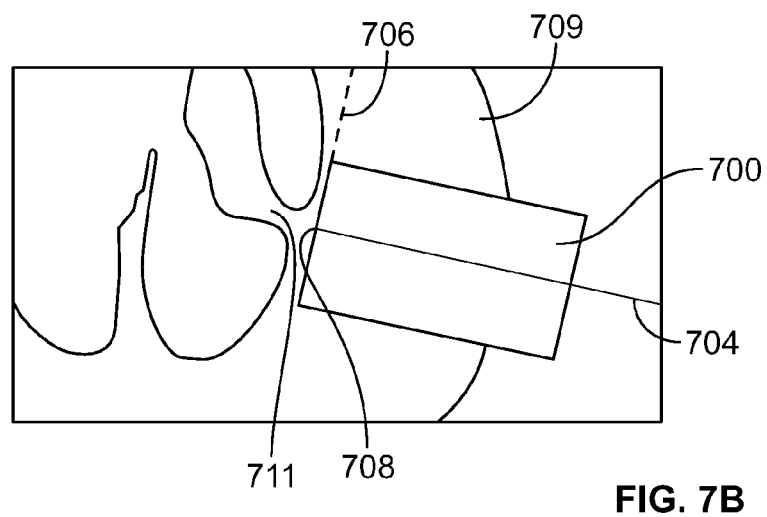
FIG. 7B depicts the body liner of FIG. 7A placed at least partially within the intergluteal cleft.

Generally, the body liner (700) may be sized such that when placed at least partially within the intergluteal cleft, at least a portion of the body liner (700) may extend out of the intergluteal cleft. For example, FIG. 7B shows the body liner (700) placed partially within the intergluteal cleft (709). As shown there, the body liner (700) may be positioned such that the target point (708) is positioned at or near the anus (711) and the body liner (700) is folded along the longitudinal axis (706). When positioned as shown in FIG. 7B, at least a portion of the body liner (700) extends outside of the intergluteal cleft (709). Generally, the exposed portion of the body liner (700) may extend far enough outside the intergluteal cleft enough to allow a wearer to grasp the body liner (700), but not so far that the body liner (700) is snagged by clothing, such as described in more detail above.

Figure 7C:
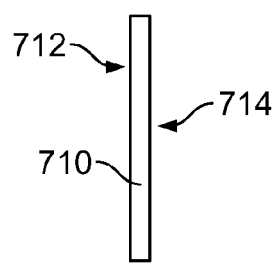
FIGS. 7C-7E depict cross-sectional side views of variations of the body liner shown in FIG. 7A.

The body liner (700) shown in FIGS. 7A and 7B may be made from one or more liner layers. For example, FIG. 7C shows a cross-sectional side view (taken along the longitudinal axis (706)) of a variation of the body liner (700) in which the body liner (700) comprises a single liner layer (710). In these variations, overall rectangular shape of the body liner (700) may be defined by the rectangular shape of the liner layer (710). Additionally, a body-facing side of the liner layer (710) may form the body-facing surface (712) of the body liner (700) and an opposite rear side of the liner layer (710) may form the rear surface (714) of the body liner (700). It should be appreciated that the body-facing surface (712) and rear surface (714) of the body liner (700) may be configured to have any respective coefficients of friction, such as described in more detail below.

The liner layer (710) may be configured to absorb fluid, such as described in more detail above. In some variations, the liner layer (710) may be configured to selectively transfer fluid as described above. For example, in some variations, the liner layer (710) may be configured to transfer fluid across the thickness of a body liner (e.g., in a "third direction" as discussed above, which may perpendicular to both the longitudinal axis (706) and the lateral axis (704)) at a wicking rate that is greater than wicking rates at which fluid is transferred within the plane of the body liner (e.g., in a "first direction" and "second direction" as discussed above). When the body liner (700) is folded over the longitudinal axis (706), a greater wicking rate across the thickness of the body liner (700) may promote transfer of fluid from a contact point on the body-facing surface (712) of the body liner on one side of the fold to the rear surface (714) on that side of the fold, and may further promote transfer from the rear surface (714) to a contacting rear surface (714) on the opposite side of the fold, as described in more detail above. Additionally or alternatively, the liner layer (710) may be configured to transfer fluid in a first direction in the plane of the body liner (700) at a wicking rate that is faster than the wicking rate in a second direction in the plane of the body liner (700) that is perpendicular to the first direction. For example, in some variations, the liner layer (710) may be configured to transfer fluid in a first direction parallel to the longitudinal axis (706) at a wicking rate that is faster than a wicking rate in a second direction parallel to the lateral axis (704). When the body liner (700) is placed at least partially in the intergluteal cleft as shown in FIG. 7B, fluid absorbed by the body liner (700) must travel parallel to the lateral axis (704) in order to reach the portions of the body liner (700) extending from the intergluteal cleft. Accordingly, having a faster wicking rate along the longitudinal axis (706) than a wicking rate along the lateral axis (704) may reduce the amount of fluid that the liner layer (702) transmits along the lateral axis (704) toward the portion of the exposed portions of the body liner (700), which may help prevent the wearer from grabbing a soiled portion of the body liner (700) during removal of the body liner.

Figure 7D:
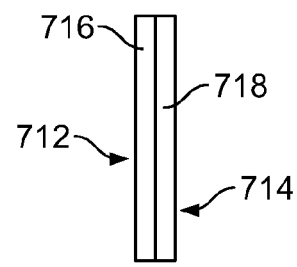

In other variations, the body liners described here may comprise two or more liner layers. For example, FIG. 7D shows a variation of body liner (700) in which the body liner is formed from a top sheet (716) and a core member (718) in contact with the top sheet (716). In some variations, the top sheet (716) and core member (718) may be the only liner layers of the body liner (700). The top sheet (716) and core member (718) may be any combination of top sheet and core member, such as those described in more detail above. In these variations, the top sheet (716) and core member (718) may have the same rectangular shape, which may be the overall shape of the body liner (700). As shown in FIG. 7D, a body-facing side of the top sheet (716) may form the body-facing surface (712) of the body liner (700) and a rear side of the core member may form the rear surface (714) of the body liner (700).

The top sheet (716) and/or core member (718) be configured to be fluid absorbent, such as described in more detail above. In some variations, both the top sheet (716) and the core member (718) are configured to be fluid absorbent. In some variations, one or both of the top sheet (716) and core member (718) may be configured to selectively transfer fluid within the respective liner layers, such as described above. For example, in some variations, the top sheet (716) may be configured to transfer fluid across the thickness of a top sheet (716) (e.g., in a "third direction", which may be perpendicular to both the longitudinal axis (706) and the lateral axis (704)) at a wicking rate that is greater than wicking rates at which fluid is transferred within the plane of the top sheet (e.g., in a "first direction" and "second direction" as discussed above). This may promote transfer of fluid through the thickness of the top sheet (716) and into the core member (718). In some of these variations, the core member (718) may be configured to transfer fluid across the thickness of a core member (718) at a wicking rate that is greater than wicking rates at which fluid is transferred within the plane of the core member (718). When the body liner (700) is folded over the longitudinal axis (706), a greater wicking rate across the thickness of the core member (718) may promote transfer of fluid from between portions of the rear surface (714) on either side of the fold via rear surface-to-rear surface contact. In other variations, the core member (718) may be configured to distribute fluid evenly through the core member (718).

In some variations, the top sheet (716) may be configured to transfer fluid in a direction parallel to the longitudinal axis (706) at a wicking rate that is faster than a wicking rate in a direction parallel to the lateral axis (704). In these variations, fluid absorbed by the top sheet (716) may be less likely to reach portions of the body liner (700) extending from the intergluteal cleft, such as described above. Additionally or alternatively, the core member (718) may be configured to transfer fluid in a direction parallel to the longitudinal axis (706) at a wicking rate that is faster than a wicking rate in a direction parallel to the lateral axis (704). In these variations, fluid absorbed by the core member (718) may be less likely to reach portions of the body (700).

Figure 7E:
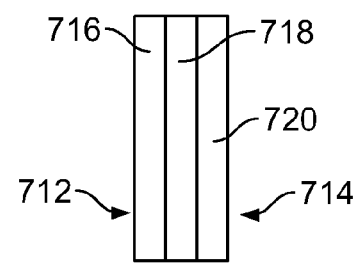

In other variations, the body liner (700) may comprise three or more liner layers. For example, FIG. 7E shows a variation of body liner (700) in which the body liner may be formed from a top sheet (716), a core member (718) in contact with the top sheet (716), and a back sheet (720) in contact with the core member (718). In some variations, the top sheet (716), core member (718), and back sheet (720) may be the only liner layers of the body liner (700). The top sheet (716), core member (718), and back sheet (720) may include any combination of top sheets, core members, and back sheets, such as those described in more detail above. In the variation shown in FIG. 7E, the top sheet (716), core member (718), and back sheet (720) may each have the same rectangular shape, which may be the same overall shape of the body liner (700). As shown there, a body-facing side of the top sheet (716) may form the body-facing surface (712) of the body liner (700) while a rear side of the back sheet (720) may form the rear surface (714) of the body liner (700). It should be appreciated that the body-facing surface (712) and rear surface (714) of the body liner (700) may be configured to have any respective coefficients of friction, such as described in more detail below.

The top sheet (716), core member (718), and/or back sheet (720) may be configured to be fluid absorbent, such as described in more detail above. In some variations, each of the top sheet (716), the core member (718), and back sheet (720) may be configured to be fluid absorbent. Some or all of the top sheet (716), core member (718), and back sheet (720) may be configured to selectively transfer fluid as described above. For example, in some variations, the top sheet (716) may be configured to transfer fluid across the thickness of a top sheet (716) (e.g., in a "third direction", which may be perpendicular to both the longitudinal axis (706) and the lateral axis (704)) at a wicking rate that is greater than wicking rates at which fluid is transferred within the plane of the top sheet (e.g., in a "first direction" and "second direction" as discussed above). This may promote quicker transfer of fluid through the thickness of the top sheet (716) and to the core member (718). In some of these variations, the core member (718) may be configured to transfer fluid across the thickness of a core member (718) at a wicking rate that is greater than wicking rate or rates at which fluid is transferred within the plane of the core member (718), which may promote quicker transfer of fluid through the thickness of the core member (718) and to the back sheet (720). In some variations, the core member (718) may be configured to distribute fluid absorbed by the core member (718) evenly though the core member. In some variations, the back sheet (720) may also be configured to transfer fluid across the thickness of the back sheet (720) at a wicking rate that is greater than wicking rates at which fluid is transferred within the plane of the back sheet (720). When the body liner (700) is folded over the longitudinal axis (706), a greater wicking rate across the thickness of the back sheet (720) may promote transfer of fluid through the thickness of the back sheet (720) and transfer of fluid to a portion of the back sheet (720) on the opposite side of the fold via back sheet-to-back sheet contact.

In some variations, the top sheet (716) may be configured to transfer fluid in a direction parallel to the longitudinal axis (706) at a wicking rate that is faster than a wicking rate in a direction parallel to the lateral axis (704). Additionally or alternatively, the core member (718) may be configured to transfer fluid in a direction parallel to the longitudinal axis (706) at a wicking rate that is faster than a wicking rate in a direction parallel to the lateral axis (704). Additionally or alternatively, the back sheet (720) may be configured to transfer fluid in a direction parallel to the longitudinal axis (706) at a wicking rate that is faster than a wicking rate in a direction parallel to the lateral axis (704). In these variations, having a faster wicking rates parallel to the longitudinal axis in some or all of the top sheet, back sheet, and core member may reduce the likelihood the absorbed fluid will reach portions of the body liner (700) extending from the intergluteal cleft.

Figure 8A:
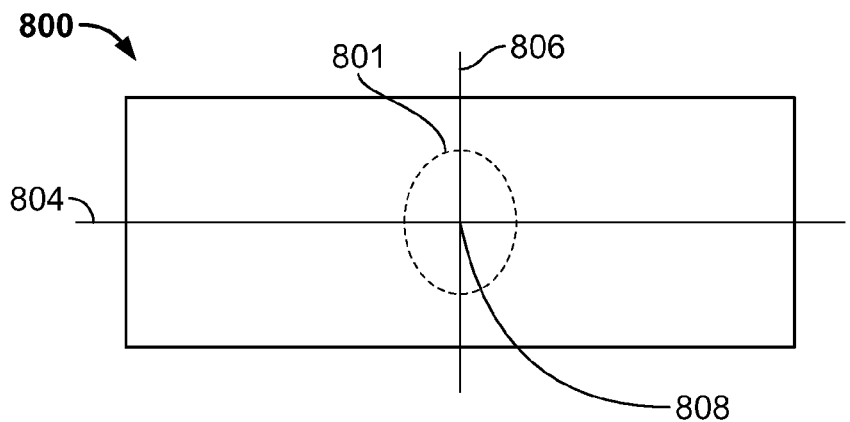
FIGS. 8A and 8E depict top views of variations of the body liners described here.

In some variations, the body liners may comprise a target zone which may have one or more different properties than surrounding portions of the body liner. For example, FIG. 8A shows a top view of body liner (800) having a rectangular shape and a target zone (801). As shown there, body liner (800) may have a longitudinal axis (806) and a lateral axis (804) perpendicular to the longitudinal axis (806) and intersecting the longitudinal axis (806) at a target point (808). When the body liner (800) is placed at least partially into the intergluteal cleft, such as described above with respect to body liner (700) in FIG. 7B, the body liner (800) may be folded along the longitudinal axis (806) to position the target point (808) at or near the anus. While the target point (808) is shown in FIG. 8A as being positioned at the center of the body liner (800), it should be appreciated that the target point (808) may be positioned at any suitable location on the body liner. Additionally, while the body liner (800) is shown in FIG. 8A as having a height along the longitudinal axis (806) smaller than a width along the lateral axis (804), it should be appreciated that in some instances the body liner (800) may have equal height and width, or may have a width along the lateral axis (804) smaller than a height along the longitudinal axis (806). The body liner (800) may comprise one or more adhesive regions (not shown), as will be described in more detail below.

Generally, the body liner (800) may be sized such that when placed at least partially within the intergluteal cleft, at least a portion of the body liner (800) may extend out of the intergluteal cleft. The body liner (800) may be positioned in the intergluteal cleft such as described above with respect to the body liner (700) shown in FIG. 7B. When so positioned, at least a portion of the body liner (800) may extend outside of the intergluteal cleft. Generally, the exposed portion of the body liner (800) extends far enough outside the intergluteal cleft enough to allow a wearer to grasp the body liner (800), but not so far that the body liner (800) is snagged by clothing, such as described in more detail above.

Figure 8B:
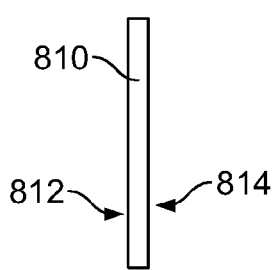
FIGS. 8B-8D depict cross-sectional side views of variations of the body liner shown in FIG. 8A.
Figure 8C:
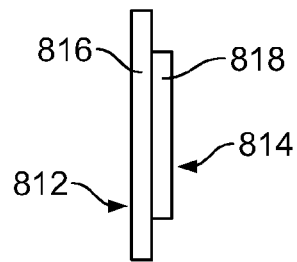
Figure 8D:
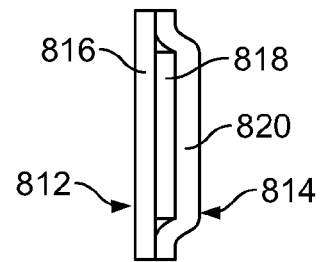
Figure 8E:
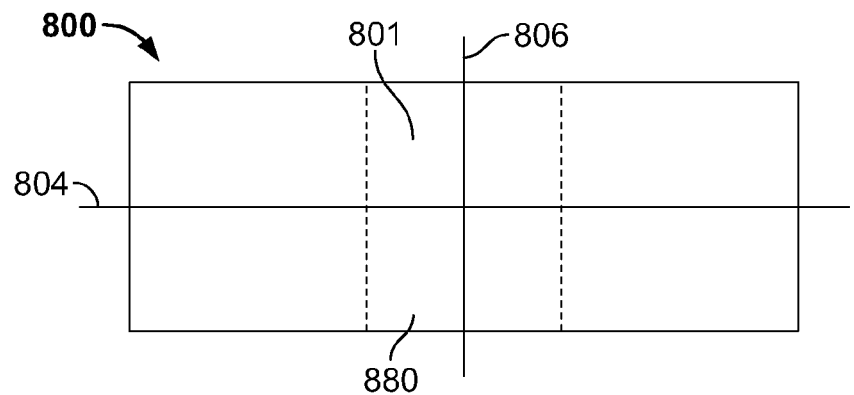

As mentioned previously, the body liner (800) may include a target zone (801). The target zone (801) may at least partially surround the target point (808) and may be configured to receive a load of anal leakage and absorb fluid therefrom. Generally, the target zone (901) may have any suitable size and shape such as described above. While shown in FIG. 8A as being oval in shape, the target zone (801) may have any suitable shape (e.g., a circle shape, a rectangular shape, an irregular shape or the like). When the target zone (801) is oval in shape, a major axis of the oval target zone (801) may be aligned parallel to the longitudinal axis (806). In other variations, the target zone (801) may be positioned such that the major axis of the oval target zone (801) is angled relative to the longitudinal axis (806) (e.g., perpendicular to longitudinal axis (806) or the like). Generally the target zone (801) may be sized such that it may fit entirely within the intergluteal cleft when the body liner (800) is placed as discussed above with respect to the variation of body liner (700) shown above in FIG. 7B. FIG. 8E shows another variation of the body liner (800) in which the target zone (801) is formed as a strip (880) that spans a length of the liner. In the variation shown in FIG. 8E, the strip (880) spans a height of the liner along the longitudinal axis (806), although it should be appreciated that in other instances the strip (880) may span a width of the liner (e.g., along the lateral axis (804)). In instances where the body liner (800) comprises a core member that defines the size and shape of the target zone (801), as will be discussed in detail below, the core member may be sized and shaped as the strip (880) shown in FIG. 8E.

The body liner (800) shown in FIG. 8A may be made from one or more liner layers. For example, FIG. 8B shows a cross-sectional side view (taken along the longitudinal axis (806)) of a variation of the body liner (800) in which the body liner (800) is formed from a single liner layer (810). In these variations, the liner layer (810) may have a rectangular shape that defines the overall shape of the body liner (800). Additionally, a body-facing side of the liner layer (810) may form the body-facing surface (812) of the body liner (800) and an opposite rear side of the liner layer (810) may form the rear surface (814) of the body liner (800). The body-facing surface (812) and/or rear surface (814) of the body liner (800) may be configured to have any respective coefficients of friction, such as described in more detail below.

The liner layer (810) may be configured to absorb fluid, such as described in more detail above. In some of these variations, the target zone (801) may have a different absorbency than surrounding portions of the body liner (800). In some of these variations, the absorbency of the target zone (801) may be greater than the absorbency of the surrounding portions of the body liner (800). For example, in some variations, the target zone (801) may be formed from a different material than the surrounding portions of the liner layer. Additionally or alternatively, the target zone (801) may be embedded with one or more absorbent materials, such as one or more super absorbent polymers, such as described in more detail above.

In some variations, the liner layer (810) may be configured to selectively transfer fluid, such as described above with respect to the variation of liner layer (710) shown in FIG. 7C. It should be appreciated that a wicking rate in a particular direction in the target zone (801) may be different than a wicking rate in the same direction in surrounding portions of the body liner (800). For example, in some variations the target zone (801) may be configured to transfer fluid within the target zone (801) faster than it is transferred within the surrounding portions of the body liner (800). In these instances, faster wicking within the target zone (801) may cause the target zone (801) to absorb more fluid than the surrounding portions of the body liner (800), which may limit the amount of fluid that may reach the periphery of the body liner (800).

In other variations, the body liners (800) may comprise two or more liner layers. For example, FIG. 8C shows a variation of the body liner (800) in which the body liner may be formed from a top sheet (816) and a core member (818) attached to the top sheet (816). In some variations, the top sheet (816) and core member (818) may be the only liner layers of the body liner (800). The top sheet (816) and core member (818) may be any combination of top sheets and core members, such as those described in more detail above. In some of these variations, the top sheet (816) may have a rectangular shape that defines the overall size and shape of the body liner (800). In some variations, the core member (818) may be the same size and shape as the target zone (801), such that core member (818) may define the overall size and shape of the target zone (801). In these variations, the core member (818) may be any suitable size such as described in more detail above. In the variation shown in FIG. 8C, a body-facing side of the top sheet (816) may form the body-facing surface (812) of the body liner (800). The rear surface (814) of the body liner (800) may be formed from a combination of the rear side of core member (818) and the portion of the rear side of the top sheet (816) that is not covered by the core member (818). The body-facing surface (812) and/or rear surface (814) of the body liner (800) may be configured to have any respective coefficients of friction, such as described in more detail below.

The top sheet (816) and/or core member (818) may be configured to be fluid absorbent, such as described in more detail above. In some variations, both the top sheet (816) and the core member (818) are configured to be fluid absorbent. In these variations, the addition of the core member (818) to the target zone (801) may increase the absorbance of the body liner (800) in the target zone (801) relative to the surrounding portions of the body liner (800). The absorbency of the body liner (800) in the target zone (801) may be further modified by modification of the body liner materials in the target zone (801) and/or inclusion of one or more absorbent materials, such as described immediately above.

In some variations, one or both of the top sheet (816) and core member (818) may be configured to selectively transfer fluid as described in more detail above. For example, the top sheet (816) may be configured to selectively transfer fluid in any manner such as those described above with respect to top sheet (716) depicted in FIG. 7D, while the core member (818) may be configured to selectively transfer fluid in any manner such as those described above with respect to core member (718) depicted in FIG. 7D. In some variations, the core member (818) may be configured to distribute fluid more quickly than the top sheet (816). In these variations, fluid absorbed by the body liner (e.g., through the top sheet (716)) may be distributed more in the core member than the top sheet, which may reduce the likelihood the fluid reaches the periphery of the body liner (800).

In other variations, the body liner (800) may comprise three or more liner layers. For example, FIG. 8D shows a variation of body liner (800) in which the body liner is formed from a top sheet (816), a back sheet (820), and a core member (818) positioned between the top sheet (816) and the back sheet (820). In some variations, the top sheet (816), core member (818), and back sheet (820) may be the only liner layers of the body liner (800). The top sheet (816), core member (818), and back sheet (820) may be any combination of top sheets, core members, and back sheets, such as those described in more detail above. In the variation shown in FIG. 8D, the top sheet (816) and the back sheet (818) may each have the same rectangular shape, which may define the overall shape of the body liner (800). The core member (818) may be the same size and shape as the target zone (801), such that core member (818) may define the overall size and shape of the target zone (801). As shown in FIG. 8D, a body-facing side of the top sheet (816) may form the body-facing surface (812) of the body liner (800) while a rear side of the back sheet (820) may form the rear surface (814) of the body liner (800). Additionally, a body-facing side of the liner layer (810) may form the body-facing surface (812) of the body liner (800) and an opposite rear side of the liner layer (810) may form the rear surface (814) of the body liner (800). The body-facing surface (812) and/or rear surface (814) of the body liner (800) may be configured to have any respective coefficients of friction, such as described in more detail below.

The top sheet (816), core member (818), and/or back sheet (820) may be configured to be fluid absorbent, such as described in more detail above. In some of these variations, each of the top sheet (816), the core member (818), and back sheet (820) may be configured to be fluid absorbent. In these variations, the addition of the core member (818) to the target zone (801) may increase the absorbance of the body liner (800) in the target zone (801) relative to the surrounding portions of the body liner (800), which may include only the top sheet (816) and the back sheet (820). The absorbency of the body liner (800) in the target zone (801) may be further modified by altering the materials of the liner layers in the target zone (801) and/or inclusion of one or more absorbent materials, such as described immediately above.

In some variations, one, two, or each of the top sheet (816), core member (818), and back sheet (820) may be configured to selectively transfer fluid as described in more detail above. For example, the top sheet (816) may be configured to selectively transfer fluid in any manner such as those described above with respect to top sheet (716) depicted in FIG. 7D, while the core member (818) may be configured to selectively transfer fluid in any manner such as those described above with respect to core member (718) depicted in FIG. 7D, and the back sheet (820) may be configured to selectively transfer fluid in any manner such as those described above with respect to the back sheet (720) depicted in FIG. 7D. In some variations, the core member (818) may be configured to distribute fluid more quickly than the top sheet (816) and the back sheet (820). In these variations, fluid absorbed by the body liner (e.g., through the top sheet (716)) may be distributed more in the core member than the top sheet and back sheet, which may reduce the likelihood the fluid reaches the periphery of the body liner (800) (e.g., by spreading past the target zone (801) into surrounding portions of the body liner (800)).

Figure 9A:
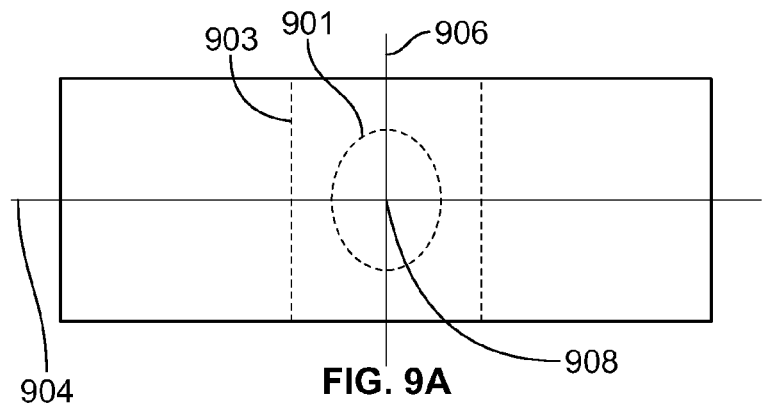
FIG. 9A depicts a top view of one variation of the body liners described here.

While the top sheet (816) and back sheet (820) are shown in FIG. 8C as having the same size and shape, it should be appreciated that the top sheet (816) and back sheet (820) may have a different size and/or shape. For example, FIG. 9A shows a top view of body liner (900) having an overall rectangular shape and a target zone (901). As shown there, body liner (900) may have a longitudinal axis (906) and a lateral axis (904) perpendicular to the longitudinal axis (906) and intersecting the longitudinal axis (906) at a target point (908). When the body liner (900) is placed at least partially into the intergluteal cleft, such as described above with respect to the body liner (700) depicted in FIG. 7B, the body liner (900) may be folded along the longitudinal axis (906) to position the target point (908) at or near the anus. While the target point (908) is shown in FIG. 9A as being positioned at the center of the body liner (900), it should be appreciated that the target point (908) may be positioned at any suitable location on the body liner. Additionally, while the body liner (900) shown in FIG. 9A as having a height along the longitudinal axis (906) smaller than a width along the lateral axis (904), it should be appreciated that in some instances the body liner (900) may have equal height and width, or may have a width along the lateral axis (904) smaller than a height along the longitudinal axis (906). The body liner (900) may comprise one or more adhesive regions (not shown), as will be described in more detail below. Generally, the body liner (900) may be sized such that when placed at least partially within the intergluteal cleft, at least a portion of the body liner (900) may extend out of the intergluteal cleft, such as described in more detail above. In some variations, the exposed portion of the body liner (900) extends far enough outside the intergluteal cleft enough to allow a wearer to grasp the body liner (900), but not so far that the body liner (900) is snagged by clothing.

As mentioned above, the body liner (900) may include a target zone (901). The target zone (901) may at least partially surround the target point (908) and may be configured to receive a load of anal leakage and absorb fluid therefrom. Generally, the target zone (901) may have any suitable size and shape such as described above. While shown in FIG. 9A as being oval in shape, the target zone (901) may have any suitable shape (e.g., a circle shape, a rectangular shape, an irregular shape or the like). When the target zone (901) is oval in shape, a major axis of the oval target zone (901) may be aligned parallel to the longitudinal axis (906). In other variations, the target zone (901) may be positioned such that the major axis of the oval target zone (901) is angled relative to the longitudinal axis (906) (e.g., perpendicular to longitudinal axis (906) or the like).

Figure 9B:
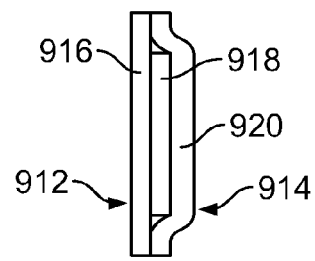
FIG. 9B depicts a cross-sectional side view of the body liner shown in FIG. 9A.

The body liner (900) shown in FIG. 9A may comprise three layers, including a top sheet (916), a core member (918), and a back sheet (920), as shown in a cross-sectional side view (taken along the longitudinal axis (906)) in FIG. 9B. In some variations, the top sheet (916), core member (918), and back sheet (920) may be the only liner layers of the body liner (900). The top sheet (916), core member (918), and back sheet (920) may be any combination of top sheets, core members, and back sheets, such as those described in more detail above. In the variation shown in FIG. 9B, the top sheet (916) have a rectangular shape, which may define the overall shape of the body liner (900) and the core member (918) may be the same size and shape as the target zone (901), such that core member (918) may define the overall size and shape of the target zone (901). In these variations, the back sheet (920) may have a shape larger than the target zone (901) yet smaller than that of the top sheet (916), such that the back sheet (920) may enclose the core member (918) between the top sheet (916) and the back sheet (920). The back sheet (920) and top sheet (916) may be connected in any suitable manner, such as described in more detail above. In these variations, a body-facing side of the top sheet (916) may form the body-facing surface (912) of the body liner (900). The rear surface (914) of the body liner (900) may be formed by a combination of a rear side of the back sheet (920) and the portions of the rear side of the top sheet (920) which are not covered by the back sheet (920).

The size and shape of the back sheet (920) may define the size and shape of a second zone (903) as indicated in FIG. 9A. While shown in FIG. 9A as being rectangular, the back sheet (920) (and with it, the second zone (903)) may have any suitable shape (e.g., a circle, an oval, an irregular shape, or the like). The second zone (903) may at least partially surround the target zone (901), and may have different properties from the target zone (901) and/or surrounding portions of the body liner (900), as will be described in more detail below.

The top sheet (916), core member (918), and/or back sheet (920) may be configured to be fluid absorbent. In some variations, each of the top sheet (916), the core member (918), and back sheet (920) may be configured to be fluid absorbent. In these variations, the inclusion of the top sheet (916), the core member (918), and the back sheet (920) in the target zone (901) may allow for greater absorbency in the target zone (901) relative to the second zone (903) (which may include just the top sheet (916) and the back sheet (920), which in turn may have greater absorbency than the surrounding portions of the body liner (900) (which may include just the top sheet (916)). The absorbency of the body liner (900) in the target zone (901), the second zone (903), and/or the surrounding portions of the body liner may be further modified by modification of the materials in one or more of the liner layers and/or the inclusion of one or more absorbent materials in one or more of the liner layers, such as described in more detail above. It should also be appreciated any or all of the top sheet (916), core member (918), and back sheet (920) may be configured to selectively transfer fluid, and may be configured to do so in any manner or combination of manners as described in more detail above.

Figure 10A:
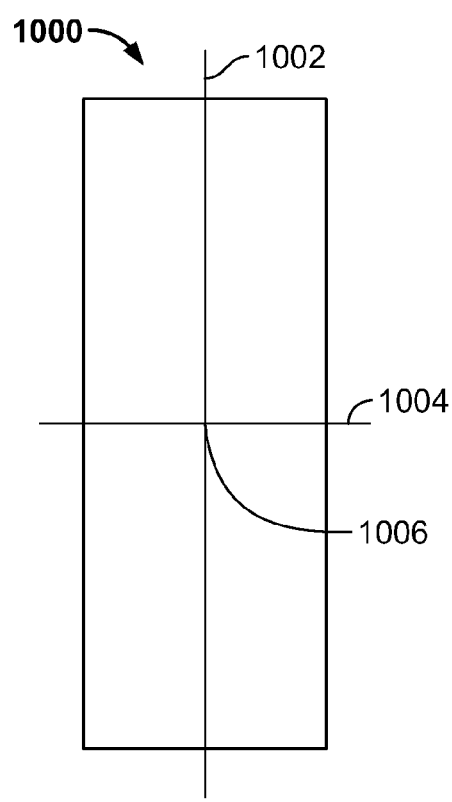
FIG. 10A depicts a top view of a variation of the body liners described here.
Figure 10B:
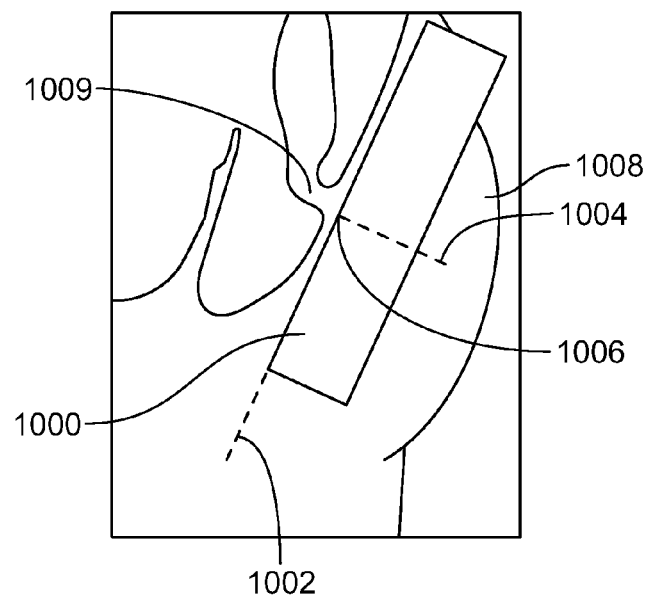
FIG. 10B depicts the body liner of FIG. 10A placed at least partially within the intergluteal cleft.

While the rectangular body liners depicted in FIGS. 7A-7E, 4A-4D, and 5A and 5B are shown in those figures as having a height along a longitudinal axis smaller than a width along a lateral axis, it should be appreciated that the body liners may have any suitable height and width. For example, FIG. 10A a first variation of a body liner (1000) having a rectangular shape, and having a longitudinal axis (1002) and lateral axis (1004) intersecting the longitudinal axis (1002) at a target point (1006). The body liner (1000) may be include any number of liner layers and may be configured in any suitable manner, such as described above with respect to FIGS. 7A-7E, except that the height of the body liner (1000) along the longitudinal axis (1002) is greater than the width along the lateral axis (1004). When the body liner (1000) is folded along the longitudinal axis (1002) and placed in the intergluteal cleft (1008) to position the target point (1006) at or near the anus (1009), the body liner (1000) may be sized such that a portion of the body liner (1000) extends outside of intergluteal cleft (1008), as depicted in FIG. 10B. As shown there, the portions of the body liner (1000) that extend outside of the intergluteal cleft at one or both ends of the body liner (1000) along the longitudinal axis (1002). In variations where the body liner (1000) (or one or more liner layers thereof) is configured to selectively transfer fluid in the plane of the body liner (1000) (or one or more liner layers thereof), it may be desirable to configure the body liner (1000) (or one or more liner layers thereof) to transfer fluid along the lateral axis (1004) at a faster wicking rate than a wicking rate long the longitudinal axis (1002). In these variations, more fluid may be transferred along the lateral axis (1004) than the longitudinal axis (1006), which may reduce the likelihood that fluid absorbed by the body liner (1000) will reach the portions of the body liner (1000) extending from the intergluteal cleft.

Figure 10C:
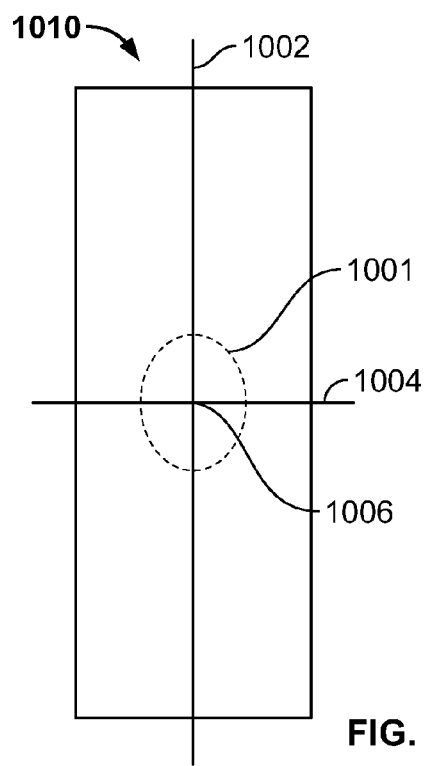
FIGS. 10C and 10D depict top views of variations of the body liners described here.

Similarly, FIG. 10C shows a variation of a body liner (1010) having a rectangular shape and a target zone (1001). The body liner may have a longitudinal axis (1002) and lateral axis (1004) intersecting the longitudinal axis (1002) at a target point (1006), and may be configured in any suitable manner such as those described above with respect to the variations of the body liner (800) depicted in FIGS. 8A-8D, except that the height of the body liner (1000) along the longitudinal axis (1002) is greater than the width along the lateral axis (1004). Again, in these variations, it may be desirable to configure the body liner (1000) (or one or more liner layers thereof) to transfer fluid along the lateral axis (1004) at a faster wicking rate than a wicking rate long the longitudinal axis (1002).

Figure 10D:
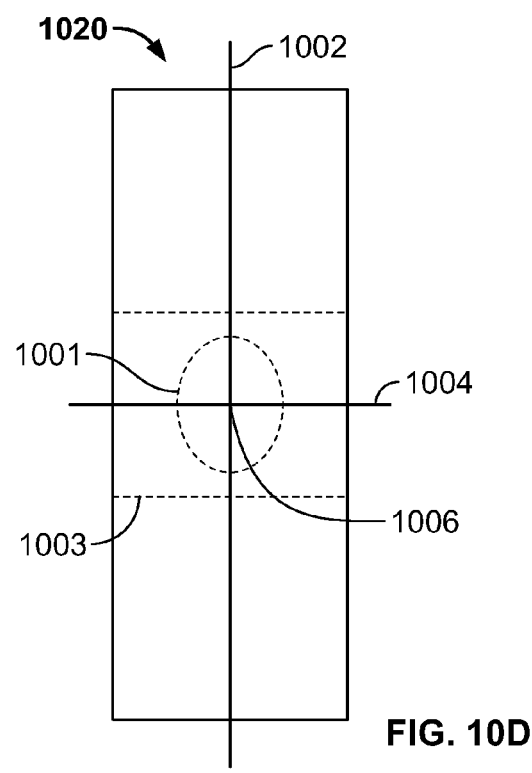

FIG. 10D shows a variation of a body liner (1020) having a rectangular shape and a target zone (1001) and a second zone (1003). The body liner may have a longitudinal axis (1002) and lateral axis (1004) intersecting the longitudinal axis (1002) at a target point (1006), and may be configured in any suitable manner such as those described above with respect to the variations of the body liner (900) depicted in FIGS. 9A-9D, except that the height of the body liner (1000) along the longitudinal axis (1002) is greater than the width along the lateral axis (1004). Again, in these variations, it may be desirable to configure the body liner (1000) (or one or more liner layers thereof) to transfer fluid along the lateral axis (1004) at a faster wicking rate than a wicking rate long the longitudinal axis (1002).

In some variations, the body liner may have a shape including one or more lobes. In these variations, the body liner may have a body portion and one or more lobes extending from the body portion. One or more of the lobes may extend from the intergluteal cleft when the body liner is placed at least partially in the intergluteal cleft, which may provide for a retrieval portion such as described in more detail above. In some variations, the body liner may comprise two or more lobes extending from the body portion. In some of these variations, the body liner may comprise two or more lobes extending from a body portion on a first side of the lateral axis of the body liner. In some of these variations, the at least one of the two or more lobes may extend from the body portion on a first side of the longitudinal axis and at least one of the two or more lobes may extend from the body portion on a second side of the longitudinal axis. In others variations, the body liner may comprise at least one lobe extending from a body portion on a first side of the lateral axis and at least one lobe extending from a body portion on a second side of the lateral axis.

In some variations, the body liner may have a shape including at least four lobes. In some of these variations, a first lobe and a second lobe may extend from a body portion on a first side of the longitudinal axis and a third lobe and a fourth lobe may extend from the body portion on a second side of the longitudinal axis. In some of these variations, the first and third lobes may extend from the body portion on a first side of the lateral axis and the second and fourth lobes may extend from the body portion a second side of the lateral axis.

Figure 11B:
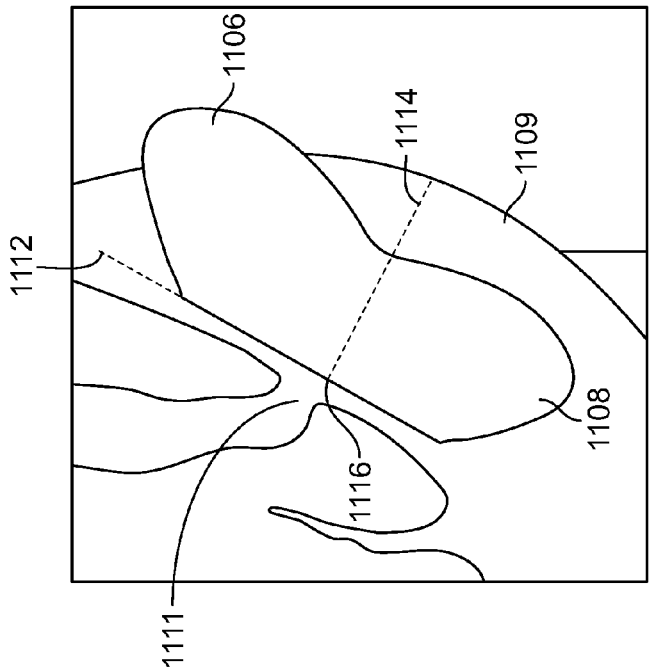
FIG. 11B depicts the body liner of FIG. 11A placed at least partially within the intergluteal cleft.
Figure 11A:
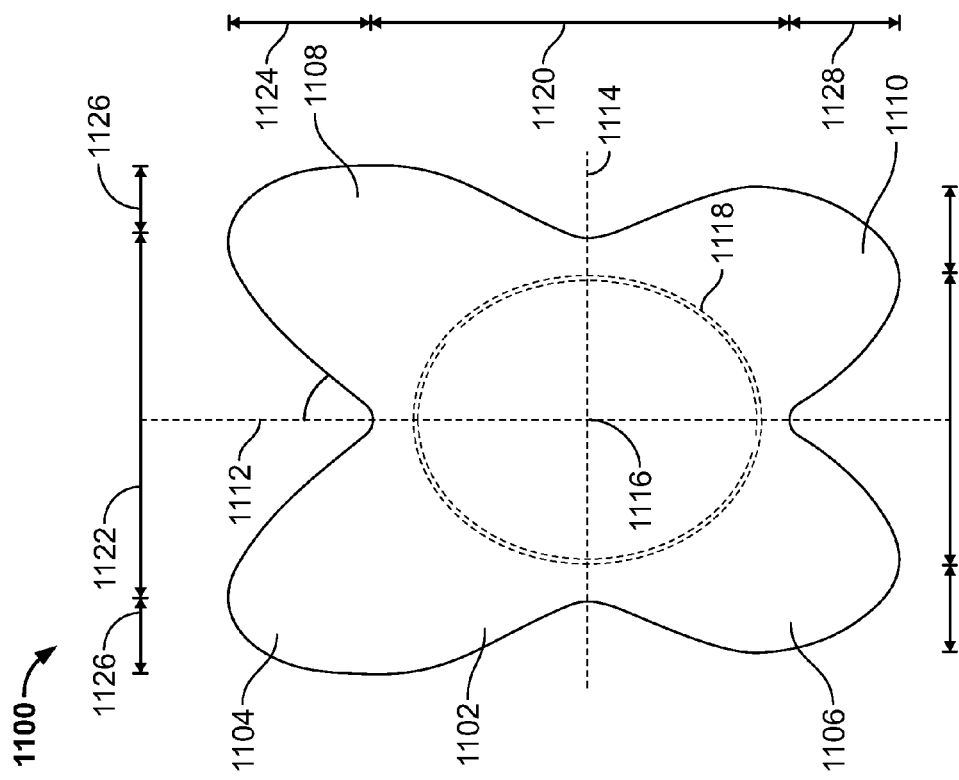
FIGS. 11A and 11F depict top views of variations of the body liners described here.

FIG. 11A shows a top view one variation of a body liner (1100) having a shape comprising a plurality of lobes. As shown there, the body liner (1100) may have a body portion (1102) and first, second, third, and fourth lobes (labeled (1104), (1106), (1108), and (1110), respectively) extending from the (1102). The body liner (1100) may further have a longitudinal axis (1112) and lateral axis (1114) perpendicularly intersecting the longitudinal axis (1112) at a target point (1116), such as described in more detail above. The first (1104) and second (1106) lobes may extend from the body portion (1102) on a first side of the longitudinal axis (1112) and the third (1108) and fourth (1110) lobes may extend from the body portion (1102) on a second side of the longitudinal axis (1112). Additionally, the first lobe (1104) and the third lobe (1108) may extend from the body portion (1102) on a first side of the lateral axis (1114) and the second lobe (1106) and the fourth lobe (1110) may extend from the body portion a second side of the lateral axis. In the variation of body liner (1100) shown in FIG. 11A, the body liner may further comprise a target zone (1118), which may have one or more properties that may differ from surrounding portions of the body liner (1100), although in some variations the body liner (1100) does not include a target zone (1118). Additionally, in some variations, the body liner (1100) may comprise one or more adhesive regions (not shown), as will be described in more detail below.

Generally, the body liner (1100) may be sized such that when placed at least partially within the intergluteal cleft, at least a portion of the body liner (1100) may extend out of the intergluteal cleft. For example, FIG. 11B depicts the body liner (1100) placed partially within the intergluteal cleft (1109). As shown there, the body liner (1100) may be positioned such that the target point (1116) is positioned at or near the anus (1111) and the body liner (1100) is folded along the longitudinal axis (1112). When positioned as shown in FIG. 11B, at least a portion of the body liner (1100) extends outside of the intergluteal cleft (1109). In the variation shown in FIG. 11B, the first (1104) and/or third lobe (1106) may be configured to extend from the intergluteal cleft (only the third lobe (1106) is shown in FIG. 11B). Generally, the exposed portion of the first (1104) and third lobes (1106) may extend far enough to be grasped by a user, but not so far that the first (1104) or third lobes (1106) is snagged by clothing, such as described in more detail above.

The body liner (1100) and lobes thereof may be any suitable dimensions. For example, as shown in FIG. 11A, the body portion (1102) may have a height (1120) along the longitudinal axis (1112) and a width (1122) along the lateral axis (1114). In some variations, the height (1120) may be at least about 5.1 cm, and may preferably be between about 7 and 8.3 cm. In some variations, the width (1122) may be at least about 5.1 cm, and may also preferably be between about 7 and 8.3 cm. The height (1102) may be greater than width (1104) (e.g., the height-to-width ratio of the body portion (1102) may be at least 1.1 or the like), may be equal to width (1104), or may be less than the width (1104) (e.g., the width-to-height ration of the body portion (1102) may be at least 1.1 or the like).

The first (1104) and third (1108) lobes may extend a distance (1126) beyond the body portion (1102) along the longitudinal axis (1112), and may extend a distance (1124) beyond the body portion (1102) along the lateral axis (1114). Similarly, the second (1106) and fourth (1110) may extend a distance (1128) beyond the body portion (1102) along the longitudinal axis (1112), and may extend a distance (1130) beyond the body portion (1102) along the lateral axis (1114). In some variations, the distance (1126) of the first (1104) and third lobes (1108) along the longitudinal axis may be longer than the distance (1128) of the second (1106) and fourth (1108) lobes. This may provide utility in instances where the first (1104) and third (1108) lobes are configured to extend at least partially from the intergluteal cleft after placement of the body liner (1100), and when the second (1106) and fourth (1108) lobes are configured to avoid contact with the genitals of the wearer. In some of these variations, the distance (1128) of the second lobe (1106) along the longitudinal axis may be less than or equal to about 90 percent of the distance (1124) of the first lobe (1104) along the longitudinal axis. In other variations, the distance (1128) may be less than about 1.9 cm. In some of these variations, the distance (1128) may be less than about 0.65 cm.

In some variations, the distance (1124) of the first (1104) and third (1108) lobes may be at least about 5 percent of the height (1120) of the body portion. In some of these variations, the distance (1124) of the first (1104) and third (1108) lobes may be preferably at least about 15 percent of the height (1120) of the body portion. In some of these variations, the distance (1124) of the first (1104) and third (1108) lobes may be preferably about 30 percent of the height (1120) of the body portion. For example, in variations where the height (1120) is about 7.6 cm, the distance (1124) may be about 2.3 cm. In some variations, the width (1126) of the lobes beyond the width (1122) of the body portion (1102) may be any suitable value (e.g., at least about 1 cm, between about 1 cm and about 2.5 cm, greater than about 2.5 cm, or the like).

The first (1104) and third (1108) lobes may each extend away from the body portion (1102) at an angle (1132) relative to the longitudinal axis (1112) of the body liner (1100). In some of these variations, it may be desirable for the angle (1132) to be less than about 45 degrees. Because the intergluteal cleft is deepest at the anal opening and becomes shallower towards the coccyx, configuring the angle (1132) to be less than about 45 degrees may reduce the overall exit length needed for the first (1104) and/or third (1108) lobes to extend at least partially out of the intergluteal cleft to act as a retrieval portion of the body liner (1100). In some variations it may also be desirable for the angle to be greater than about 10 degrees, which may help reduce the possibility that the first (1104) and third (1108) lobes may catch on each other and bunch. Accordingly, in some variations the angle (1132) may be between about 10 degrees and about 45 degrees. In some of these variations, the angle (1132) may preferably be about 40 degrees.

Figure 11C:
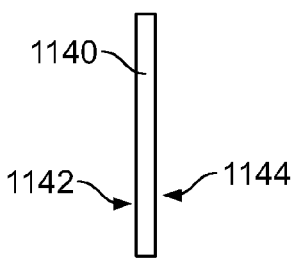
FIGS. 11C-11E depict cross-sectional side views of variations of the body liner shown in FIG. 11A.
Figure 11D:
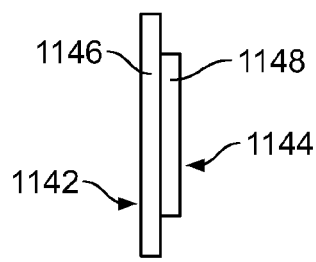
Figure 11E:
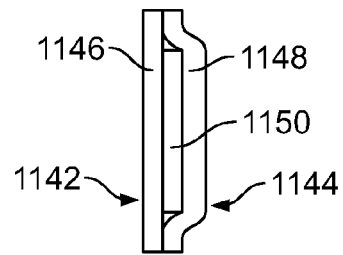
Figure 11F:
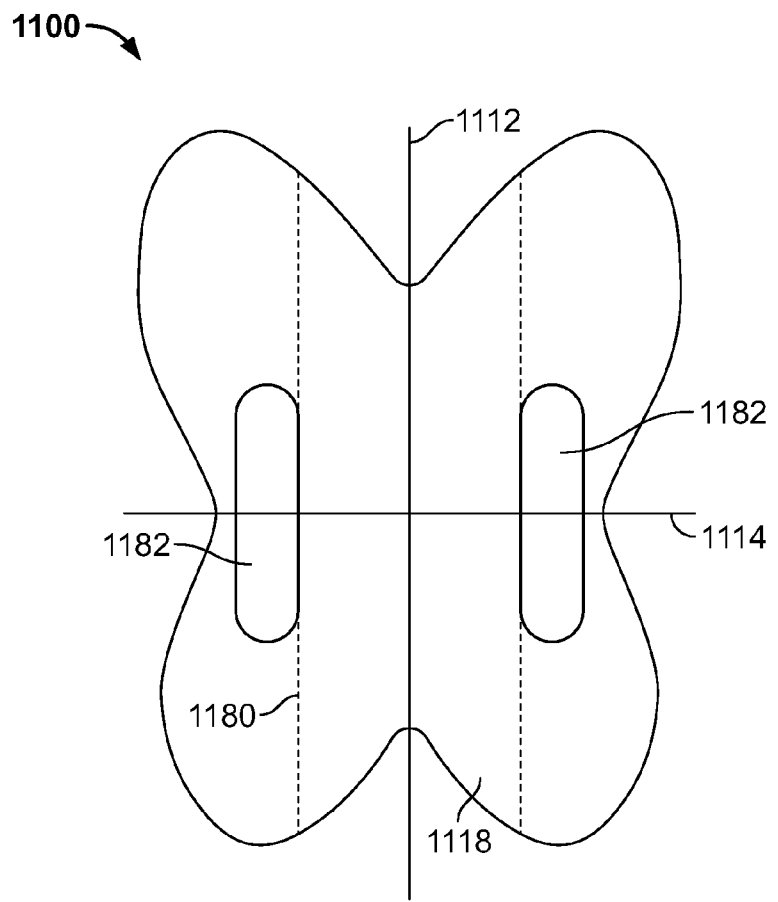

As mentioned previously, the body liner (1100) may include a target zone (1118). The target zone (1118) may at least partially surround the target point (1116) and may be configured to receive a load of anal leakage and absorb fluid therefrom. Generally, the target zone (901) may have any suitable size and shape such as described above. While shown in FIG. 11A as being oval in shape, the target zone (1118) may have any suitable shape (e.g., a circle shape, a rectangular shape, an irregular shape or the like). When the target zone (1118) is oval in shape, a major axis of the oval target zone (1118) may be aligned parallel to the longitudinal axis (1112). In other variations, the target zone (1118) may be positioned such that the major axis of the oval target zone (1118) is angled relative to the longitudinal axis (1112) (e.g., perpendicular to longitudinal axis (1112) or the like). Generally the target zone (1118) may be sized such that it may fit entirely within the intergluteal cleft when the body liner (1100) is placed as discussed above with respect to FIG. 11B. FIG. 11F shows another variation of the body liner (1100) in which the target zone (1118) is formed as a strip (1180) that spans a length of the liner. In the variation shown in FIG. 11F, the strip (1180) spans a height of the liner along the longitudinal axis (1112), although it should be appreciated that in other instances the strip (1180) may span a width of the liner (e.g., along the lateral axis (1114)). In instances where the body liner (1100) comprises a core member that defines the size and shape of the target zone (1118), as will be discussed in detail below, the core member may be sized and shaped as the strip (1180) shown in FIG. 4F. Also shown there are adhesive regions (1182), such as those described below.

The body liner (1100) shown in FIG. 11A may be made from one or more liner layers. For example, FIG. 11C shows a cross-sectional side view (taken along the longitudinal axis (1112)) of a variation of the body liner (1100) in which the body liner (1100) is formed from a single liner layer (1140). In these variations, the liner layer (1140) may have a lobed shape (the four-lobed shape shown in FIG. 11A may be a butterfly shape) that defines the overall shape of the body liner (1100). Additionally, a body-facing side of the liner layer (1140) may form the body-facing surface (1142) of the body liner (1100) and an opposite rear side of the liner layer (1140) may form the rear surface (1144) of the body liner (1100). The body-facing surface (1142) and/or rear surface (1144) of the body liner (1100) may be configured to have any respective coefficients of friction, such as described in more detail below.

The liner layer (1140) may be configured to absorb fluid, such as described in more detail above. In some of these variations, the target zone (1118) may have a different absorbency than surrounding portions of the body liner (1100). In some of these variations, the absorbency of the target zone (1118) may be greater than the absorbency of the surrounding portions of the body liner (1100). For example, in some variations, the target zone (1118) may be formed from a different material than the surrounding portions of the liner layer. Additionally or alternatively, the target zone (1118) may be embedded with one or more absorbent materials, such as one or more super absorbent polymers, such as described in more detail above.

In some variations, the liner layer (1140) may be configured to selectively transfer fluid, such as described above. For example, in some variations, the liner layer (1140) may be configured to transfer fluid across the thickness of a body liner (e.g., in a "third direction" as discussed above, which may perpendicular to both the longitudinal axis (1112) and the lateral axis (1114)) at a wicking rate that is greater than wicking rates at which fluid is transferred within the plane of the body liner (e.g., in a "first direction" and "second direction" as discussed above). When the body liner (1100) is folded over the longitudinal axis (1112), a greater wicking rate across the thickness of the body liner (1100) may promote transfer of fluid from a contact point on the body-facing surface (1142) of the body liner on one side of the fold to the rear surface (1144) on that side of the fold, and may further promote transfer from the rear surface (1144) to a contacting rear surface (1144) on the opposite side of the fold, as described in more detail above. Additionally or alternatively, the liner layer (1140) may be configured to transfer fluid in a first direction in the plane of the body liner (1100) at a wicking rate that is faster than the wicking rate in a second direction in the plane of the body liner (1100) that is perpendicular to the first direction. For example, in some variations, the liner layer (1140) may be configured to transfer fluid in a first direction parallel to the longitudinal axis (1112) at a wicking rate that is slower than a wicking rate in a second direction parallel to the lateral axis (1114). When the body liner (1100) is placed at least partially in the intergluteal cleft as shown in FIG. 11B, fluid absorbed by the body liner (1100) may need to travel parallel to the longitudinal axis (1112) in order to reach the portions of the body liner (1100) extending from the intergluteal cleft. Accordingly, having a faster wicking rate along the lateral axis (1114) than a wicking rate along the longitudinal axis (1112) may reduce the amount of fluid that the liner layer (1140) transmits along the longitudinal axis (1112) toward the portion of the exposed portions of the body liner (1100), which may help prevent the wearer from grabbing a soiled portion of the body liner (1100) during removal of the body liner.

It should be appreciated that a wicking rate in a particular direction in the target zone (1118) may be different than a wicking rate in the same direction in surrounding portions of the body liner (1100). For example, in some variations the target zone (1118) may be configured to transfer fluid within the target zone (1118) faster than it is transferred within the surrounding portions of the body liner (1100). In these instances, faster wicking within the target zone (1118) may cause the target zone (1118) to absorb more fluid than the surrounding portions of the body liner (1100), which may limit the amount of fluid that may reach the periphery of the body liner (1100).

In other variations, the body liners (1100) may comprise two or more liner layers. For example, FIG. 11D shows a variation of the body liner (1100) in which the body liner may be formed from a top sheet (1146) and a core member (1148) attached to the top sheet (1146). In some variations, the top sheet (1146) and core member (1148) may be the only liner layers of the body liner (1100). The top sheet (1146) and core member (1148) may be any combination of top sheets and core members, such as those described in more detail above. In some of these variations, the top sheet (1146) may be a lobed shape that defines the overall size and shape of the body liner (1100). In some variations, the core member (1148) may be the same size and shape as the target zone (1118), such that core member (1148) may define the overall size and shape of the target zone (1118). In these variations, the core member (1148) may be any suitable size such as described in more detail above. In the variation shown in FIG. 11D, a body-facing side of the top sheet (1146) may form the body-facing surface (1142) of the body liner (1100). The rear surface (1144) of the body liner (1100) may be formed from a combination of the rear side of core member (1148) and the portion of the rear side of the top sheet (1146) that is not covered by the core member (1148). The body-facing surface (1142) and/or rear surface (1144) of the body liner (1100) may be configured to have any respective coefficients of friction, such as described in more detail below.

The top sheet (1146) and/or core member (1148) may be configured to be fluid absorbent, such as described in more detail above. In some variations, both the top sheet (1146) and the core member (1148) are configured to be fluid absorbent. In these variations, the addition of the core member (1148) to the target zone (1118) may increase the absorbance of the body liner (1100) in the target zone (1118) relative to the surrounding portions of the body liner (1100). The absorbency of the body liner (1100) in the target zone (1118) may be further modified by modification of the body liner materials in the target zone (1118) and/or inclusion of one or more absorbent materials, such as described immediately above.

In some variations, one or both of the top sheet (1146) and core member (1148) may be configured to selectively transfer fluid as described in more detail above. For example, in some variations, the top sheet (1146) may be configured to transfer fluid across the thickness of a top sheet (1146) (e.g., in a "third direction", which may be perpendicular to both the longitudinal axis (1112) and the lateral axis (1114)) at a wicking rate that is greater than wicking rates at which fluid is transferred within the plane of the top sheet (e.g., in a "first direction" and "second direction" as discussed above). This may promote transfer of fluid through the thickness of the top sheet (1146) and into the core member (1148). In some of these variations, the core member (1148) may be configured to transfer fluid across the thickness of a core member (1148) at a wicking rate that is greater than wicking rates at which fluid is transferred within the plane of the core member (1148). When the body liner (1100) is folded over the longitudinal axis (1112), a greater wicking rate across the thickness of the core member (1148) may promote transfer of fluid from between portions of the rear surface (1144) on either side of the fold via rear surface-to-rear surface contact. In other variations, the core member (1148) may be configured to distribute fluid evenly through the core member (1148).

In some variations, the top sheet (1146) may be configured to transfer fluid in a direction parallel to the longitudinal axis (1112) at a wicking rate that is slower than a wicking rate in a direction parallel to the lateral axis (1114). In these variations, fluid absorbed by the top sheet (1146) may be less likely to reach portions of the body liner (1100) extending from the intergluteal cleft, such as described above. Additionally or alternatively, the core member (1148) may be configured to transfer fluid in a direction parallel to the longitudinal axis (1146) at a wicking rate that is slower than a wicking rate in a direction parallel to the lateral axis (1114). In these variations, fluid absorbed by the core member (1148) may be less likely to reach portions of the body (1100).

In other variations, the body liner (1100) may comprise three or more liner layers. For example, FIG. 11E shows a variation of body liner (1100) in which the body liner is formed from a top sheet (1146), a back sheet (1140), and a core member (1148) positioned between the top sheet (1146) and the back sheet (1140). In some variations, the top sheet (1146), core member (1148), and back sheet (1140) may be the only liner layers of the body liner (1100). The top sheet (1146), core member (1148), and back sheet (1140) may be any combination of top sheets, core members, and back sheets, such as those described in more detail above. In the variation shown in FIG. 4D, the top sheet (1146) and the back sheet (1148) may each have the same oval shape, which may define the overall shape of the body liner (1100). The core member (1148) may be the same size and shape as the target zone (1118), such that core member (1148) may define the overall size and shape of the target zone (1118). As shown in FIG. 11E, a body-facing side of the top sheet (1146) may form the body-facing surface (1142) of the body liner (1100) while a rear side of the back sheet (1140) may form the rear surface (1144) of the body liner (1100). Additionally, a body-facing side of the liner layer (1140) may form the body-facing surface (1142) of the body liner (1100) and an opposite rear side of the liner layer (1140) may form the rear surface (1144) of the body liner (1100). The body-facing surface (1142) and/or rear surface (1144) of the body liner (1100) may be configured to have any respective coefficients of friction, such as described in more detail below.

The top sheet (1146), core member (1148), and/or back sheet (420) may be configured to be fluid absorbent, such as described in more detail above. In some of these variations, each of the top sheet (1146), the core member (1148), and back sheet (1140) may be configured to be fluid absorbent. In these variations, the addition of the core member (1148) to the target zone (1118) may increase the absorbance of the body liner (1100) in the target zone (1118) relative to the surrounding portions of the body liner (1100), which may include only the top sheet (1146) and the back sheet (1140). The absorbency of the body liner (1100) in the target zone (1118) may be further modified by altering the materials of the liner layers in the target zone (1118) and/or inclusion of one or more absorbent materials, such as described immediately above.

In some variations, one, two, or each of the top sheet (1146), core member (1148), and back sheet (1140) may be configured to selectively transfer fluid as described in more detail above. For example, in some variations, the top sheet (1146) may be configured to transfer fluid across the thickness of a top sheet (1146) (e.g., in a "third direction", which may be perpendicular to both the longitudinal axis (1112) and the lateral axis (1114)) at a wicking rate that is greater than wicking rates at which fluid is transferred within the plane of the top sheet (e.g., in a "first direction" and "second direction" as discussed above). This may promote quicker transfer of fluid through the thickness of the top sheet (1146) and to the core member (1148). In some of these variations, the core member (1148) may be configured to transfer fluid across the thickness of a core member (1148) at a wicking rate that is greater than wicking rate or rates at which fluid is transferred within the plane of the core member (1148), which may promote quicker transfer of fluid through the thickness of the core member (1148) and to the back sheet (1140). In some variations, the core member (1148) may be configured to distribute fluid absorbed by the core member (1148) evenly though the core member. In some variations, the back sheet (1140) may also be configured to transfer fluid across the thickness of the back sheet (1140) at a wicking rate that is greater than wicking rates at which fluid is transferred within the plane of the back sheet (1140). When the body liner (1100) is folded over the longitudinal axis (1112), a greater wicking rate across the thickness of the back sheet (1140) may promote transfer of fluid through the thickness of the back sheet (1140) and transfer of fluid to a portion of the back sheet (1140) on the opposite side of the fold via back sheet-to-back sheet contact.

In some variations, the top sheet (1146) may be configured to transfer fluid in a direction parallel to the longitudinal axis (1112) at a wicking rate that is slower than a wicking rate in a direction parallel to the lateral axis (1124). Additionally or alternatively, the core member (1148) may be configured to transfer fluid in a direction parallel to the longitudinal axis (1112) at a wicking rate that is slower than a wicking rate in a direction parallel to the lateral axis (1114). Additionally or alternatively, the back sheet (1140) may be configured to transfer fluid in a direction parallel to the longitudinal axis (1112) at a wicking rate that is slower than a wicking rate in a direction parallel to the lateral axis (1114). In these variations, having a faster wicking rates parallel to the lateral axis in some or all of the top sheet, back sheet, and core member may reduce the likelihood the absorbed fluid will reach portions of the body liner (1100) extending from the intergluteal cleft.

In some variations, the core member (1148) may be configured to distribute fluid more quickly than the top sheet (1146) and the back sheet (420). In these variations, fluid absorbed by the body liner (e.g., through the top sheet (316)) may be distributed more in the core member than the top sheet and back sheet, which may reduce the likelihood the fluid reaches the periphery of the body liner (1100) (e.g., by spreading past the target zone (1118) into surrounding portions of the body liner (1100)).

Body Liner Retention

When the body liners described here are folded over and placed at least partially in the intergluteal cleft, movement of the wearer may apply one or more forces to the body liner, which may have a tendency to bunch, dislodge or otherwise displace the body liner. For example, movement of the legs during routine movement (such as walking) may cause the buttocks to rub against one another. When a body liner is folded along its longitudinal axis, this movement may cause the rear surface of the body liner on one side of the folded longitudinal axis to rub against the rear surface of the body liner on the other side of the longitudinal axis. Friction between folded-over rear surfaces may cause the body liner to slip relative to skin of the buttocks, which may result in bunching or displacement of the body liner. Bunching may result in discomfort to the wearer, and may reduce the ability of the body liner to absorb and/or immobilize anal leakage. Accordingly, it may be desirable to configure the body liners described here to minimize displacement or bunching the body liner during movement of a wearer.

In some variations, it may be desirable to configure the rear surface of the body liner to maximize slip between opposing segments of the rear surface when the body liner is folded over as described above, which may reduce the likelihood of bunching or displacement of the body liner. In these variations it may be desirable to reduce or minimize the coefficient of friction of the rear surface of the body liner. For example, in some variations a body liner may comprise a rear surface having a coefficient of friction less than about 0.15. In some of these variations, the rear surface preferably has a coefficient of friction less than about 0.1. The coefficient of friction of the rear surface of the body liner may be minimized in any suitable manner. In some variations, the rear surface of the body liner may be formed from a material or materials comprising a low coefficient of friction. Additionally or alternatively, the rear surface of the body liner may be polished to reduce the coefficient of friction of the rear surface. In some variations, the rear surface of the body liner may be coated with one or more materials (e.g., one or more powders or silicones) which may reduce the coefficient of friction of the rear surface. With a reduced coefficient of friction, the rear surface of the body liner may have a silkiness that encourages slip. Thus, when the body liner is folded along a longitudinal axis and positioned at least in the intergluteal cleft (e.g., to position the rear surface in contact with itself), the rear surface of the body liner on one side of the longitudinal axis may be more likely to slip relative to the rear surface of the body liner on the other side of the longitudinal axis, which may reduce the likelihood of body liner bunching or movement of the body liner relative to the skin of the buttocks.

As described in more detail above, one or more liner layers may form the rear surface of the body liners described here. For example, in variations where the body liner comprises a single liner layer, a rear side of the liner layer may form the rear surface of the body liner. In some these variations, the rear side of the single liner layer may be configured to have a reduced coefficient of friction such as described immediately above (e.g., the rear side of the single liner layer may be formed from a material have a low free-fiber index, may be polished, and/or may include one or more coatings). In other variations, the body liner may comprise a plurality of liner layers, and the rear surface of the body liner may be formed by portions of the rear sides of the some or all of the liner layers. In these variations, the portions of the rear sides of the liner layers forming the rear surface of the body liner may be configured to have a reduced coefficient of friction such as described immediately above. For example, in variations in which a body liner comprises a back sheet and a rear side of the back sheet forms the rear surface of the body liner, the back sheet may be configured to have a reduce coefficient of friction such as described in more detail above (e.g., the rear side of the single liner layer may be formed from a material have a low free-fiber index, may be polished, and/or may include one or more coatings).

In some variations, it may be desirable to configure to minimize slip between the body-facing surface of the body liner and the skin of a wearer when the body liner is folded over and placed into the intergluteal cleft. When the body liners comprise one or more adhesive regions on a body-facing surface, such as will be described in more detail below, the adhesive regions may help prevent movement between the body-facing surface and the skin. In some these variations, it may be desirable to lower the coefficient of friction (e.g., in one of the manners as described above) of the portions of the body-facing surface not covered by adhesive regions, which may increase the comfort level provided by the body liner (e.g., by providing a smooth or silky surface to the tissue). In other instances, it may be desirable to maximize or otherwise increase the coefficient of friction of the body-facing surface of the body liner to reduce the likelihood of movement between the body liner and skin of the user. This may find particular utility in instances where the body liner does not include one or more adhesive regions. For example, in some variations a body liner may comprise a body-facing surface having a coefficient of friction greater than about 0.25. In some of these variations, the body-facing surface preferably has a coefficient of friction greater than about 0.3. The coefficient of friction of the body-facing surface of the body liner may be maximized or otherwise increased in any suitable manner. In some variations, the body-facing surface of the body liner may be formed from a material or materials comprising a higher coefficient of friction. Additionally or alternatively, the body-facing surface of the body liner may be roughened or textured (e.g., via carding, needle punching, burnishing, or the like) to increase the coefficient of friction of the body-facing surface. In some variations, the body-facing surface of the body liner may be coated with one or more materials (e.g., a tacky spray or the like) which may increase the coefficient of friction of the body-facing surface. With an increased coefficient of friction, the body-facing surface of the body liner may move tend to move with the skin, and may be less likely to move relative to the skin when the rear surface is rubbing against itself. This may reduce body liner bunching or displacement of the body liner relative to wearer. Additionally, the increased coefficient of friction may result in a fluffier/softer body-facing surface, which may provide greater comfort to a wearer when the body-facing surface is placed in contact with skin of the wearer.

As described in more detail above, one or more liner layers may form the body-facing surface of the body liners described here. For example, in variations where the body liner comprises a single liner layer, a body-facing side of the liner layer may form the body-facing surface of the body liner. In some of these variations, the body-facing side of the single liner layer may be configured to have an increased coefficient of friction such as described immediately above (e.g., the body-facing side of the single liner layer may be formed from a material have a high free-fiber index, may be roughened/textured, and/or may include one or more friction-increasing coatings). In other variations, the body liner may comprise a plurality of liner layers, and the body-facing surface of the body liner may be formed by portions of the body-facing sides of some or all of the liner layers. In these variations, the portions of the body-facing sides of the liner layers forming the body-facing surface of the body liner may be configured to have an increased coefficient of friction such as described immediately above. For example, in variations in which a body liner comprises a top sheet and a body-facing side of the top sheet forms the body-facing surface of the body liner, the top sheet may be configured to have an increased coefficient of friction such as described above (e.g., the body-facing side of the single liner layer may be formed from a material have a high free-fiber index, may be roughened/textured, and/or may include one or more friction-increasing coatings).

In some instances, it may be desirable to both maximize slip between opposing portions of the rear surface of a body liner and minimize slip between the body-facing surface of the body liner and the skin of a wearer. In some variations, the body-facing surface of a body liner may have a coefficient of friction larger than a coefficient of friction of the rear surface of the body liner. The body-facing surface and rear surface may have any suitable coefficients of frictions, such as described immediately above. For example, in some variations the body liner may have a body-facing surface having a coefficient of friction greater than about 0.25, and a rear surface having a coefficient of less than about 0.15. In some of these variations, the body-facing surface preferably has a coefficient of friction greater than about 0.30, and the rear surface preferably has a coefficient of friction less than about 0.1. The coefficient of friction of each surface of the body liner may be altered based on the materials, polishing or texturing, and/or friction-altering coatings such as described immediately above.

In variations where the body liner comprises a single liner layer, a body-facing side of the liner layer may form the body-facing surface of the body liner while a rear side of the liner layer may form the rear surface of the body liner. In some of these variations, the materials used to form the single liner layer may be altered along the thickness of the liner layer such that the liner layer may have a free-fiber index on a body-facing side of the liner layer that is larger than the free-fiber index on the rear side of the liner layer. Additionally or alternatively, the body-facing side of the liner layer may roughened or textured to increase the coefficient of friction of the body-facing surface of the body liner (e.g., the body-facing side may be formed with a textured pattern, ridges, and/or bumps which may enhance the coefficient of friction of the body-facing surface). Additionally or alternatively, the rear side of the liner layer may be polished to decrease the coefficient of friction of the rear surface of the body liner. Additionally or alternatively, one or more sides of the liner layer may include a coating which may alter the coefficient of friction of the body-facing surface and/or the rear surface of the body liner (e.g., the body-facing side may comprise a friction-enhancing coating, the rear side may comprise a friction-reducing coating, combinations thereof and the like).

In variations where a body liner comprises a plurality of liner layers, the body-facing surface of the body liner may be formed by portions of the rear sides of some or all of the liner layers, such as described in more detail above. Similarly, the rear surface of the body liner may be formed by portions of the rear sides of some or all of the liner layers. In these variations, the body-facing surface and/or the rear surface of the body liner configured in any manner as described above to achieve a larger coefficient of friction in the body-facing surface of the body liner than the rear surface. For example, in some variations in which a body liner comprises a top sheet and a back sheet, a body-facing side of the top sheet may form the body-facing surface of the body liner, and a rear side of the back sheet may form the rear surface of the body liner. In these variations, the back sheet may be configured to have a lower coefficient of friction than the top sheet. For example, the back sheet may be formed from a material or materials having a lower free-fiber index than the material or materials forming the top sheet. In some of these variations, or in variations in which the top sheet and back sheet are formed from the same material or materials, the back sheet may be polished and/or may comprise one or more friction-reducing coatings, such as described in more detail above. Additionally or alternatively, the top sheet may be roughened or texture and/or may comprise one or more friction-enhancing coatings, such as described in more detail above.

As mentioned above, the body liners may comprise one or more adhesive regions, which may help to hold the body liner in place relative to body tissue. When a body liner is placed within the intergluteal cleft, differential motion of the buttocks during movement (e.g., walking) may have a tendency to drive the body liner out of the intergluteal cleft. Additionally, when a wearer sits (e.g., to urinate), squats, or otherwise moves in a manner that separates the buttocks, gravity may act to pull a body liner from the intergluteal cleft. Accordingly, when a body liner comprises one or more adhesive regions, the adhesive regions may be configured to adhere the body liner to the skin of the buttocks. The adherence provided by the adhesive regions may help prevent movement between the body liner and the buttocks during wearer movement, and may suspend the body liner against gravitational forces when the buttocks are separated. Thus, when a wearer sits down on a toilet, the body liner may be retained in place, which may allow the wearer to urinate without dislodgement of the body liner.

Generally, the adhesive regions described may comprise one or more adherent materials which may applied to one or more surfaces of the body liner. The adherent materials may be any suitable skin-safe material. In some variations, the adhesive regions may comprise one or more adhesives. In some of these variations, the adhesive regions may comprise a pressure-sensitive adhesive. The pressure-sensitive adhesive may include an acrylic adhesive (such as, for example, 3M™ MSX-6674C adhesive tape), a rubber adhesive, a silicone adhesive, a polyurethane adhesive, a polyester adhesive, a polyether adhesive, a hydrogel adhesive, a glycerin or tarpene-based adhesive, combinations thereof and the like. In some variations, the adhesive regions may comprise one or more non-adhesive materials that may have a tack that sticks/adheres the body liner to the tissue. For example, in some variations the adhesive regions may comprise one or more waxes (e.g., such as a paraffin wax). It should be appreciated that in some instances, an adhesive region may include a combination of two or more adherent materials, such as those described immediately above.

The adhesive regions may be configured to have any suitable adhesion strength. It may be desirable to configure the adhesive region to be strong enough to resist or prevent movement of the body liner during movement of the wearer (which may help to maintain a target point of the body liner at or near the anus), yet not be so strong as to cause pain or damage skin when the body liner is peeled off of skin and hair during removal of the body liner. For example, in some variations, the adhesive regions of a body liner may have an adhesion strength between about 5 oz/in and about 48 oz/in when bonded to SST. In some variations, the adhesion strength is preferably between about 20 oz/in and about 40 oz/in when bonded to SST. In these variations, the adhesion strength may provide feedback to a wearer which gives the wearer a sense of security that the body liner is securely held in place.

The adhesive regions are generally placed on a body-facing surface of the body liner, such that when the body liner is placed in the intergluteal cleft, the adhesive regions are positioned between the body liner and the skin of the intergluteal cleft to adhere the body liner to the wearer's skin. When the body comprises one or more liner layers, the adherent materials of the adhesive region may be applied to any suitable liner layer. For example, in variation in which the body liner comprises a single liner layer, such as described in more detail above, the adhesive region may be located on a body-facing side of the single liner layer.

When the body liner comprises multiple liner layers (e.g., a top sheet and a core member and/or back sheet), the adhesive regions of the body liner may be located on a body-facing side of some or all of the liner layers. For example, in some variations, an adhesive region may be positioned on a body-facing side of a top sheet. In other variations, an adhesive region may be positioned at least partially on a body-facing side of a back sheet. In some of these variations, because the top sheet is generally positioned between the back sheet and the skin of the intergluteal cleft, the top sheet may comprise one or more apertures which may expose a portion of a body-facing side of the back sheet. The adhesive material may be disposed on the exposed portion of the body-facing side of the back sheet. This may find particular utility in instances where the back sheet is formed from a strong material than the top sheet. Because the adhesive region may resist removal of the body liner when a wearer pulls on a portion of the body liner, attaching the adhesive region to the stronger back sheet may reduce the likelihood that the body liner will rip or tear during body liner removal.

Figure 12A:
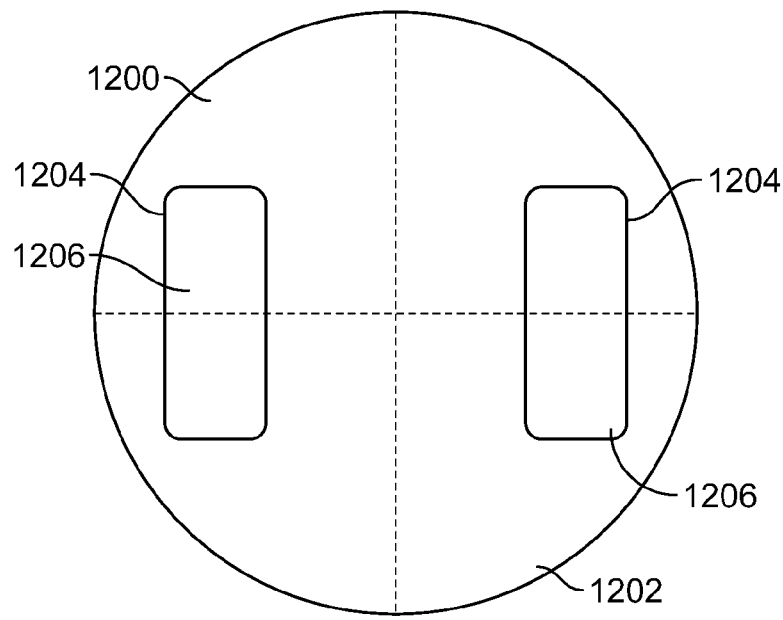
FIGS. 12A and 12B, 13A and 13B, and 14 depict variations of body liners comprising one or more adhesive regions.
Figure 12B:
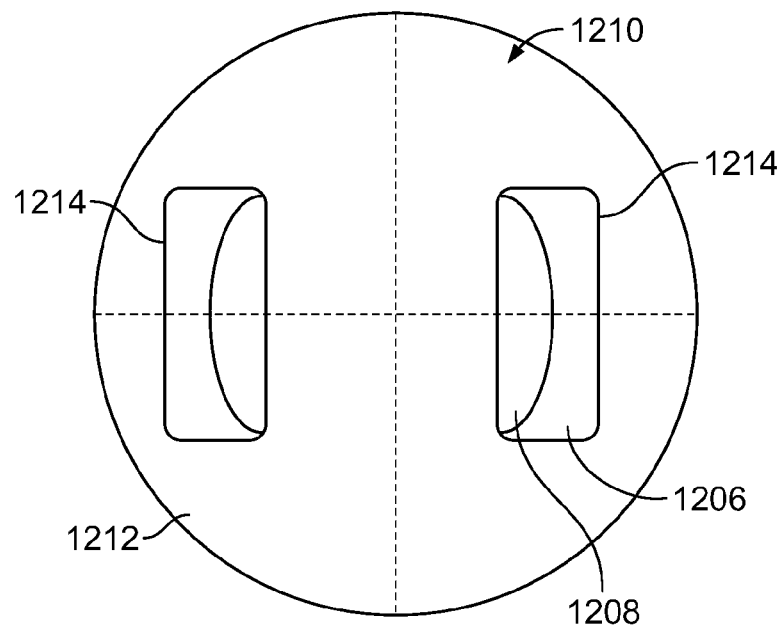

It should be appreciated that an aperture in a top sheet may also expose a portion of a body-facing side of a core member (e.g., in variations where the body liner comprises a top sheet, a back sheet, and a core member). In some of these variations, the exposed portion of the core member may also be removed such that only the body-facing side of the back sheet is exposed through the aperture in the top sheet. In these variations, adhesive material applied in the aperture of the top sheet may only be applied on the body-facing side of the back sheet. For example, FIG. 12A shows a portion of a variation of a body liner (1200) comprising a top sheet (1202) having an aperture (1204) therethrough to expose a body-facing side of a back sheet (1206). An adhesive material (not shown) may be placed on the back sheet (1206) through the aperture (1204) to form an adhesive region on the back sheet (1206). In others of these variations, the portion of the core member exposed through the aperture in the top sheet may be left in place, and adhesive material placed through the aperture in the top sheet may be applied to the body-facing side of the back sheet and the body-facing side of the core member. For example, FIG. 12B shows a portion of a variation of a body liner (1210) comprising a top sheet (1212) having an aperture (1214) therethrough to expose a portion of the body-facing side of a back sheet (1206) and a portion of the body-facing side of a core member (1208). An adhesive material (not shown) may be placed on both the back sheet (1206) and the core member (1208) to form an adhesive region on the back sheet and core member. In still other variations, an aperture in a top sheet may expose only a portion of a body-facing side of a core member (e.g., in variations in which a body liner comprises a top sheet and a core member, or variations in which a body liner comprises a top sheet, a core member, and back sheet). In these variations, the adhesive material may be placed in the aperture to dispose the adhesive material on the core member. It should be appreciated when an adhesive material or materials are placed in an aperture in a top sheet to create an adhesive region on a body-facing side of a core member and/or back sheet, the adhesive material or materials may also be applied to the top sheet around the aperture to increase the area of adhesive region beyond the boundary of the aperture.

The adhesive materials described above may be attached to a body liner in any suitable manner. In some variations, an adhesive tape may be attached to the body liner in the form an adhesive region. For example, 3M™ MSX-6674C adhesive tape may include a dual-adhesive tape having an acrylic adhesive on one side of the tape and a synthetic rubber adhesive on an opposite of the tape. The rubber adhesive may be applied to a body-facing surface of the body liner to attach the adhesive tape thereto and to position the acrylic adhesive to face away from the body-facing surface of the body liner to allow for adherence to a wearer's skin. In other variations, an adhesive may be applied as a hot melt adhesive. In these variations, the adhesive may be applied the body liner at a high temperature, and may form a strong bond with the body liner. As the adhesive cools, the tackiness of the adhesive may decrease to a level suitable for adherence to the skin, such as discussed above. In other variations, an adhesive may be cross-linked into place relative to the body liner (e.g., by application of heat, ultraviolet and/or ionizing energy, combinations thereof and the like).

Generally, the body liner comprises at least one adhesive region on each side of the longitudinal axis, although it should be appreciated that in some instances, the body liners described here may comprise adhesive regions only on one side of the longitudinal axis. When the body liner comprises at least one adhesive region on each side of the longitudinal axis, and the body liner is folded along the longitudinal axis during placement of the body liner in the intergluteal cleft, separation of the buttocks (e.g., during sitting on a toilet) may pull the body liner at the adhesive regions. This may flatten the body liner between the adhesive regions during separation of the buttocks, which may allow still allow the body liner to capture leakage from the anus. The adherence between adhesive regions and the buttocks may suspend the body liner, allowing the body liner to remain in place.

Figure 13A:
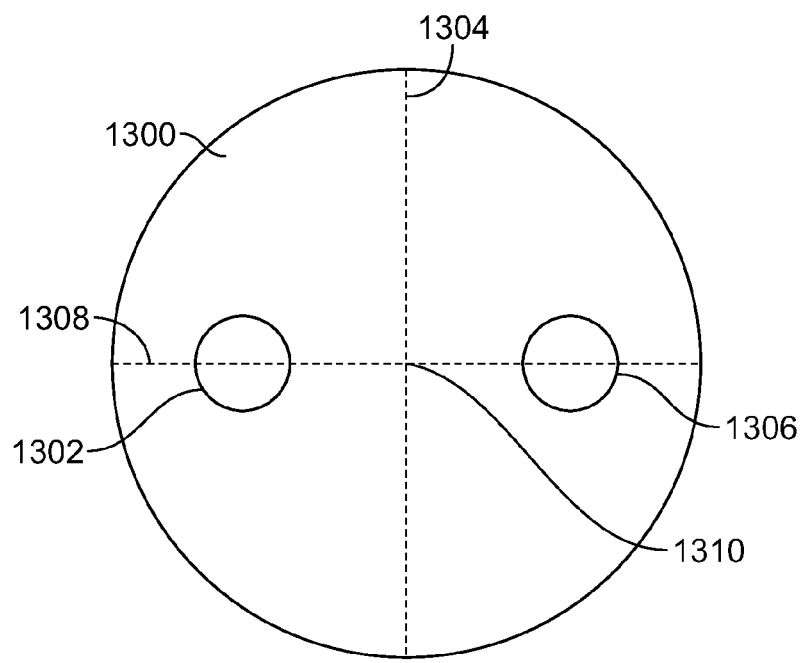
Figure 13B:
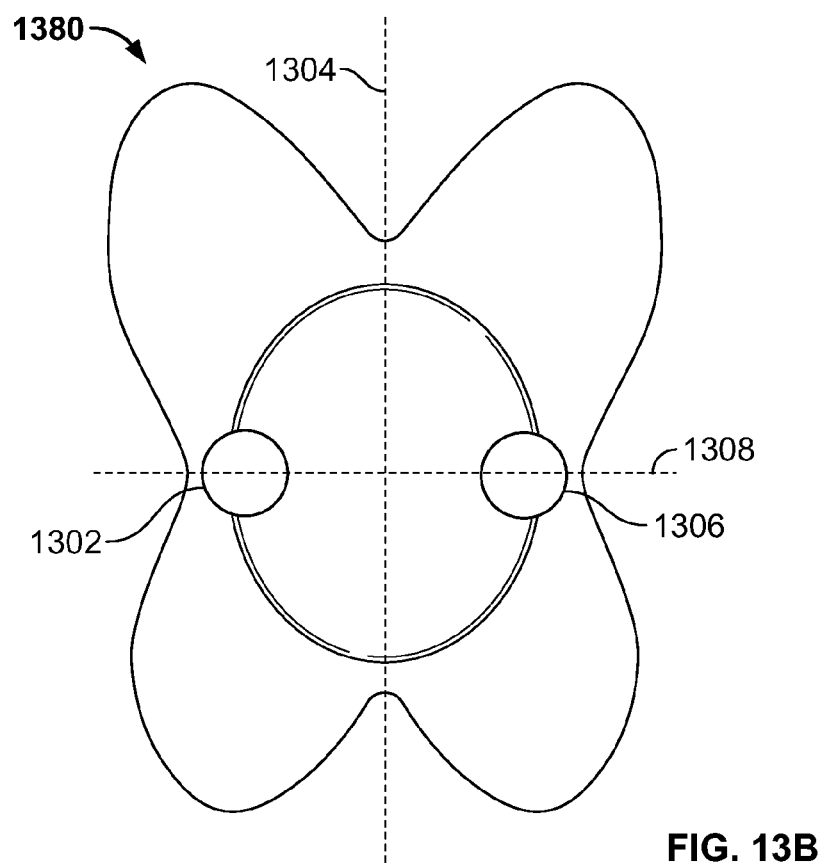

The adhesive regions described here may have any suitable size or shape. For example, in some variations, an adhesive region may have a circular or oval shape. FIG. 13A shows a variation of a portion of a body liner (1300) comprising a first adhesive region (1302) on a first side of a longitudinal axis (1304) of the body liner (1300) and a second adhesive region (1306) on a second side of the longitudinal axis (1304). As shown there, the first (1302) and second (1306) adhesive regions may be circular in shape. Also shown there is a lateral axis (1308) perpendicularly intersecting the longitudinal axis (1304) at a target point (1310), such as described in more detail above. The first and second adhesive regions are preferably centered on the lateral axis (1308). In some variations, both of the first and second adhesive regions intersect the lateral axis (1308), but at least one of the first and second adhesive regions are not centered on the lateral axis (1308). In other variations, one or both of the first and second adhesive regions do not intersect the lateral axis (1308). FIG. 13B shows a variation of a butterfly-shaped body liner (1380) having first (1302) and second (1306) circular adhesive regions as described with respect to FIG. 13A.

In variations where a body liner comprises a circular adhesive region (such as the first (1302) and second (1306) adhesive regions shown in FIG. 13A), the adhesive region may have any suitable diameter. In some variations, the adhesive region may have a diameter less than or equal to about 0.65 cm. In other variations, the adhesive region may have a diameter less than or equal to about 1.3 cm. While shown in FIG. 13A as having two circular adhesive regions (one on each side of the longitudinal axis (1304)), it should be appreciated that the body liner may include one or more additional adhesive regions, which may have any shape or shapes such as described hereinthroughout.

In some variations, one or both of first (1302) and second (1306) adhesive regions may have an oval shape. In these variations, an oval adhesive region may be oriented in any suitable manner relative to the longitudinal (1304) and lateral (1308) axes. In some variations, a major axis of an oval adhesive region may be parallel to the longitudinal axis (1304). In other variations, the major axis of the oval adhesive region may be angled relative to the longitudinal axis. In some of these variations, the major axis of the oval adhesive region may be perpendicular to the longitudinal axis (1304) (i.e., the major axis of the oval adhesive region may parallel to the lateral axis (1308)). In variations of the body liners described here that include an oval adhesive region, the oval adhesive region may have any suitable dimensions. For example, in some variations, an oval adhesive region may have a minor axis less than or equal to about 1.3 cm. In some of these variations, the minor axis may be less than or equal to about 0.65 cm. In some variations, the oval adhesive region may have a major axis that is less than or equal to about 3.8 cm. In some of these variations, the major axis may be less than or equal to about 3.2 cm.

Figure 14:
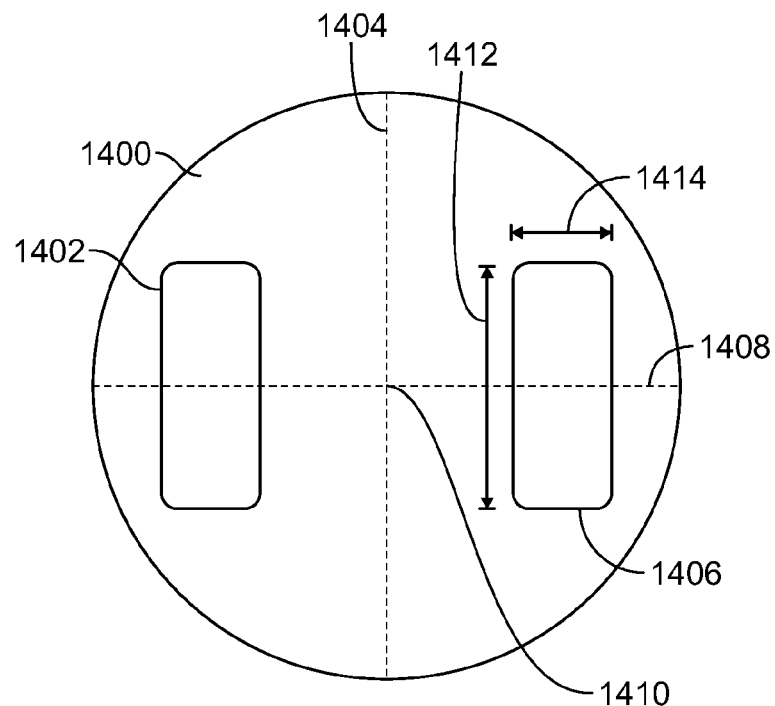

In some variations, the body liners described here may comprise one or more adhesive regions that have a substantially rectangular shape. For example, FIG. 14 shows a variation of a portion of a body liner (1400) comprising a first adhesive region (1402) on a first side of a longitudinal axis (1404) of the body liner (1400) and a second adhesive region (1406) on a second side of the longitudinal axis (1404). As shown there, the first (1402) and second (1406) adhesive regions may be rectangular in shape (although it should be appreciated that the adhesive regions may have rounded corners as shown in FIG. 14. Also shown there is a lateral axis (1408) perpendicularly intersecting the longitudinal axis (1404) at a target point (1410), such as described in more detail above. The first and second adhesive regions are preferably centered on the lateral axis (1408). In some variations, both of the first and second adhesive regions intersect the lateral axis (1408), but at least one of the first and second adhesive regions are not centered on the lateral axis (1408). In other variations, one or both of the first and second adhesive regions do not intersect the lateral axis (1408).

The rectangular adhesive region may have a height (1412) along the longitudinal axis (1404) and a width (1414) along the lateral axis (1408). In the variation shown in FIG. 14, height (1412) may greater than its width (1414). These variations may find particular utility in variations where the height of the body liner along the longitudinal axis (1404) is greater than the width of the body liner (1408) along the lateral axis (1408). When the height (1412) is greater than the width (1414), the rectangular adhesive region may have any suitable height-to-width ratio. For example, in some variations a rectangular adhesive region may have a height-to-width ratio that is at least about 1.1. In some of these variations, height-to-width ratio is at least about 2.5. In some of these variations, height-to-width ratio is at least about 5. In some variations, the width (1414) and height (1412) may be about 0.65 cm and about 3.2 cm respectively. In other variations, the width (1414) and height (1412) may be about 1.3 cm and about 3.2 cm respectively. In still other variations, the width (1414) and height (1412) may be about 0.95 cm and about 3.5 cm respectively.

In other variations, a rectangular adhesive region may have a height (1412) equal to its width (1414) (i.e., is square shaped). In still other variations, a rectangular adhesive region may have a width (1414) greater than its height (1412). These variations may find particular utility in variations where the body liner (1400) has a width along the lateral axis (1408) greater than a height along the longitudinal axis (1404). When the height (1412) is greater than the width (1414), the rectangular adhesive region may have any suitable width-to-height ratio. For example, in some variations a rectangular adhesive region may have a width-to-height ratio that is at least about 1.1. In some of these variations, width-to-height ratio is at least about 2.5. In some of these variations, width-to-height ratio is at least about 5. In some variations, the height (1412) and width (1414) may be about 0.65 cm and about 3.2 cm respectively. In other variations, the height (1412) and width (1414) may be about 1.3 cm and about 3.2 cm respectively. In still other variations, the height (1412) and width (1414) may be about 0.95 cm and about 3.5 cm respectively.

Figure 17A:
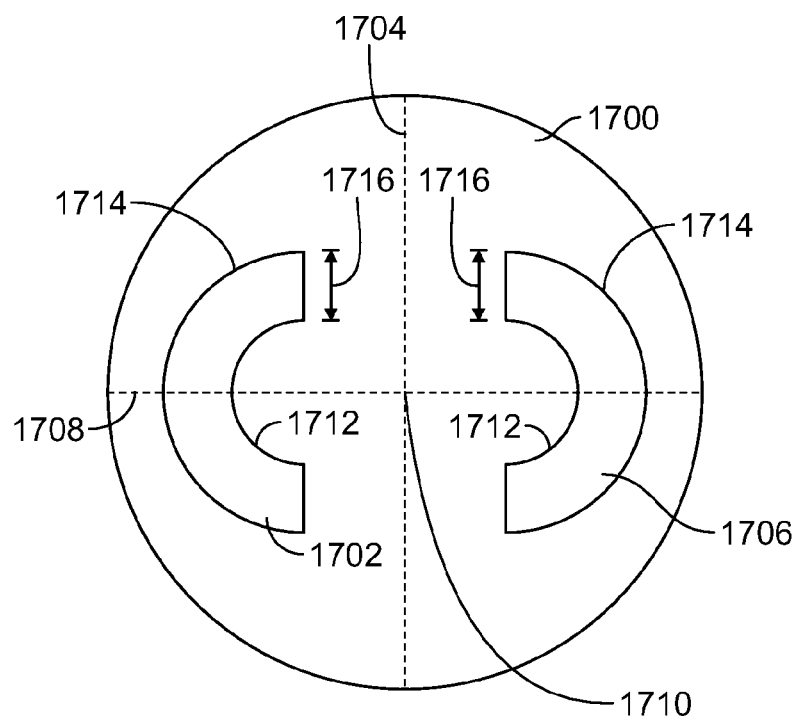
FIGS. 17A-17C depict variations of a body liner comprising one or more adhesive regions.
Figure 17C:
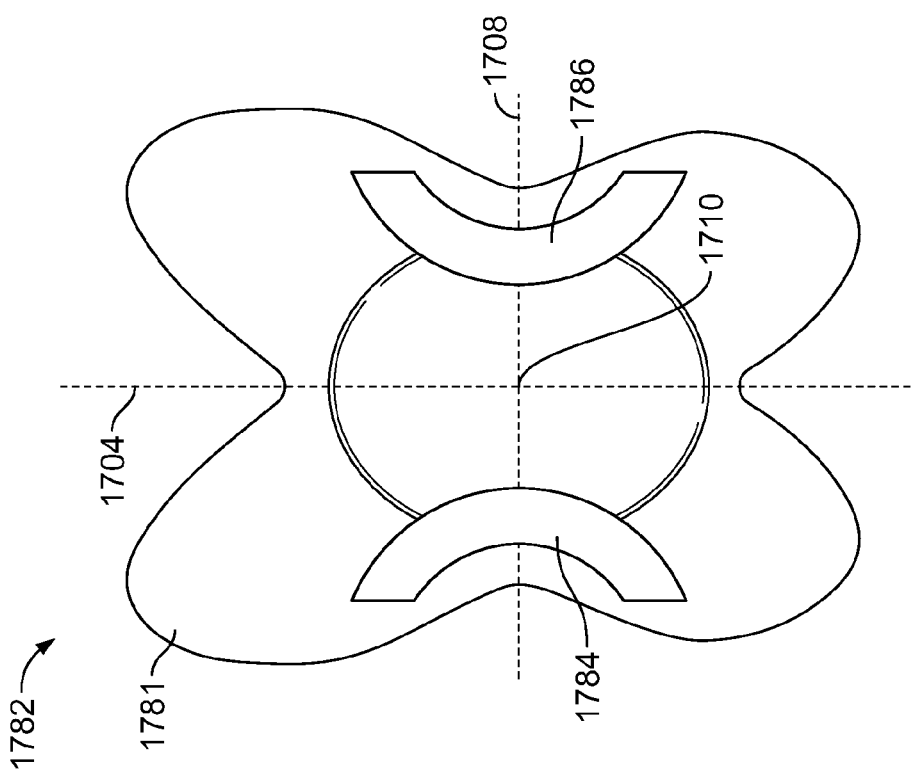
Figure 17B:
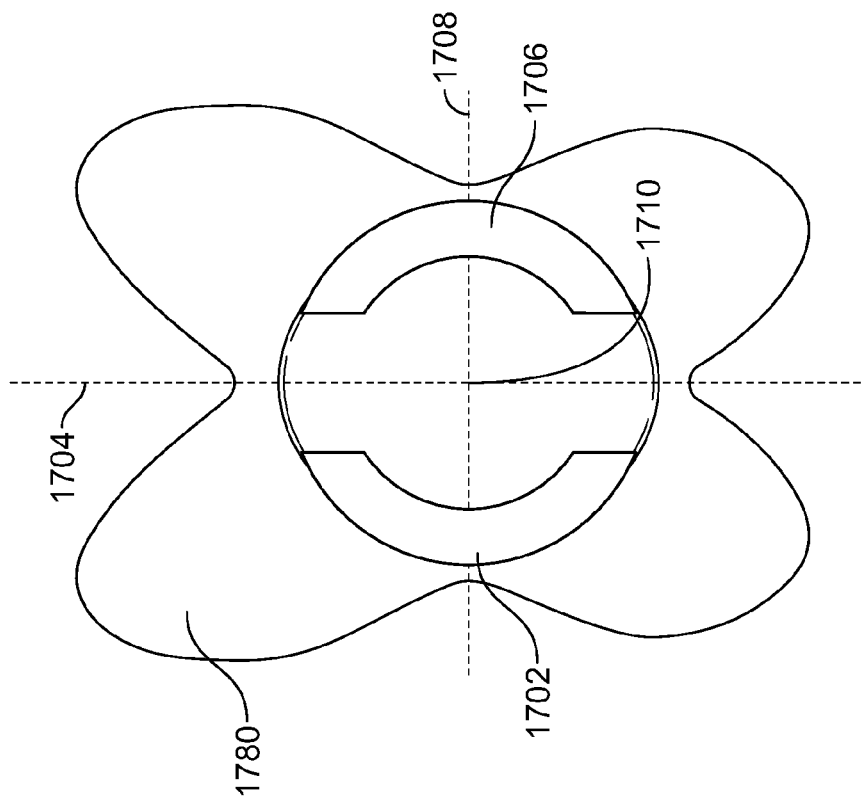

In some variations, an adhesive region may have a shape that is an arc segment, which may be an arc segment of an oval or a circle. FIG. 17A shows a variation of a portion of a body liner (1700) comprising a first adhesive region (1702) on a first side of a longitudinal axis (1704) of the body liner (1700) and a second adhesive region (1706) on a second side of the longitudinal axis (1704). Also shown there is a lateral axis (1708) perpendicularly intersecting the longitudinal axis (1704) at a target point (1710), such as described in more detail above. As shown there, each of the first (1702) and second (1706) adhesive regions may be an arc segment having an inner radius of curvature (1712), an outer radius of curvature (1714), and a thickness (1716). In some variations, the target point (1710) may be the center of curvature of the inner radius of curvature, the outer radius of curvature, or both the inner and outer radii of curvature. The thickness (1716) may be any suitable value, such as for example, about 0.65 cm, about 0.95 cm, or the like. Additionally, the arc segment of the first and second adhesive regions may be subtend any angle of the circle and/or oval. In some variations, the arc segment may subtend an angle less than 180 degrees. In some of these variations, the arc segment may subtend an angle less than 135 degrees. In some of these variations, the arc may subtend an angle less than 90 degrees. In some of these variations, the arc may subtend an angle less than 45 degrees. Additionally, in some variations, the inner radius of curvature may be at least about 1 cm, and the outer radius of curvature may be less than or equal to about 5 cm. FIG. 17B shows a variation of a butterfly-shaped body liner (1780) having first (1702) and second (1706) adhesive regions as described above with respect to FIG. 17A. Additionally, while shown in FIG. 17B as curving toward the target point (1710), it should be appreciated that one or both of the adhesive regions may curve away from the target point (1710). For example, FIG. 17C shows a variation of a body liner (1781) having first (1784) and second (1786) arc-shaped adhesive regions, wherein the adhesive regions curve away from the target point (1710).

When the body liners described here comprise one or more adhesive regions, such as those described immediately above, it may be desirable to limit the placement of the adhesive regions relative to a target point on the body liner and/or the longitudinal and lateral axes of the body liner. For example, the skin immediately surrounding the anus is highly innervated, such that placement of an adhesive on this skin may cause unnecessary pain or discomfort. Accordingly it may be desirable to space any adhesive regions a minimum distance away from a target point which will placed at or near the anus. For example, in some variations, the adhesive regions of the body liner may each be spaced at least 1 cm from a target point of the body liner.

Additionally or alternatively, it may be desirable to configure a body liner that such that any adhesive regions are positioned within a certain distance of the target point. For example, it may be desirable to ensure that the adhesive regions are within the intergluteal cleft when the target point is positioned at or near the anus. Additionally, placing the adhesive region closer to the anus will reduce the movement of the adhesive regions during movement of the body liner, since the buttocks tend to move more relative the anus closer to the anus than the edge of the intergluteal cleft. For example, in some variations each of the adhesive regions of a body liner may be positioned within about 5.1 cm from the target point. In some of these variations, each of the adhesive regions of the body liner may be positioned within about 3.5 cm from the target point. In some of these variations, each of the adhesive regions of the body liner may be positioned within about 3.2 cm from the target point.

Additionally or alternatively, it may be desirable to configure the body liner such that any adhesive regions do not cross the longitudinal axis of the body liner. This may allow the body liner to fold and flatten when the wearer stands and sits, respectively. In some variations, each of the adhesive regions may be positioned such that they are spaced at least 0.65 cm from the longitudinal axis. In some of these variations, each of the adhesive regions may be position such they are spaced at least 1 cm from the longitudinal axis.

Figure 18A:
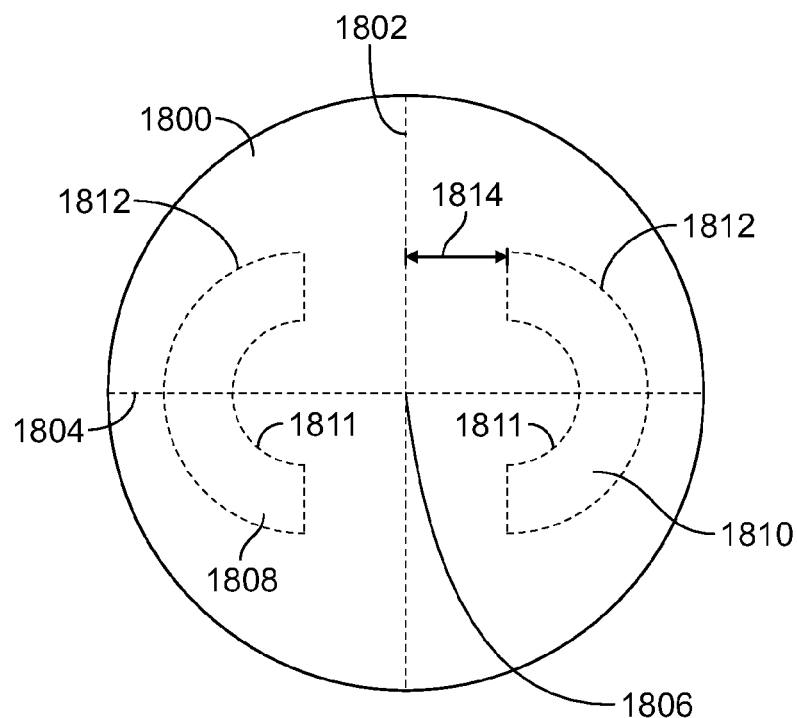
FIGS. 18A and 18B depict variations of a body liner comprising one or more adhesive zones.
Figure 18B:
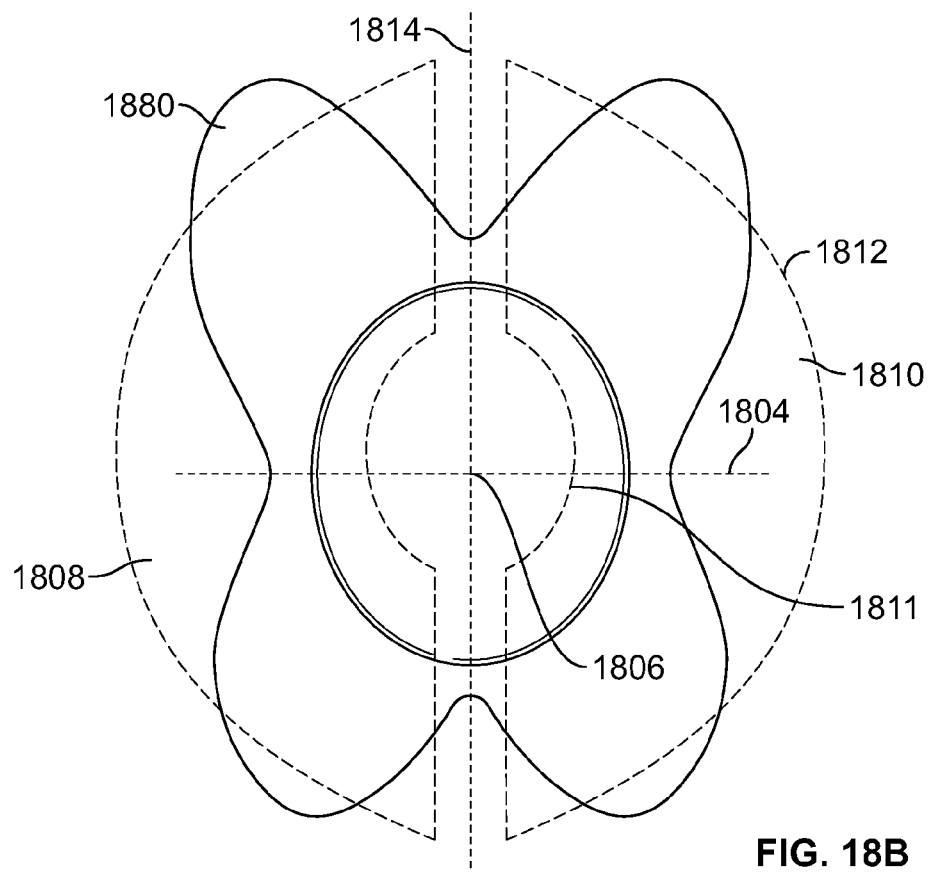

In some variations, some or all of the above placement locations described above may be combined to define one or more adhesive zones. In these variations, the body liner may be configured such that any adhesive zones of the body liner are positioned within the adhesive zone (e.g., there are no adhesive regions outside of the adhesive zones). For example, FIG. 18A shows a portion of a variation of a body liner (1800) having a longitudinal axis (1802) and a lateral axis (1804) perpendicularly intersecting the longitudinal axis (1802) at a target point (1806). Further shown there are a first adhesive zone (1808) on a first side of the longitudinal axis (1802) and a second adhesive zone (1810) on a second side of the longitudinal axis (1806). As shown there, the first and second adhesive zones may have a shape of an arc segment having an inner curve (1811) and an outer curve (1812), and may be positioned a distance (1814) away from the longitudinal axis (1806). The target point (1806) may be the center of curvature of the inner curve (1811) and the outer curve (1812). The radius of curvature of the outer curve (1812) may represent the outer boundary in which the adhesive regions may be located, and may be any suitable value. In some variations, radius of the curvature of the outer curve (1812) may be less than or equal to about 5.1 cm. In other variations, radius of the curvature of the outer curve (1812) may be less than or equal to about 3.5 cm. In still other variations, radius of the curvature of the outer curve (1812) may be less than or equal to about 3.2 cm. Similarly, the radius of curvature of the inner curve (1811) may represent the inner boundary of placement of the adhesive regions, and may have any suitable value. In some variations, the radius of curvature of the inner curve (1811) may be at least about 1 cm. The distance (1814) between the adhesive zones and the longitudinal axis (1802) may be any suitable value. In some variations, the distance (1814) may be at least 0.65 cm. In some of these variations, the adhesive may be at least about 1 cm. FIG. 18B shows a variation of a butterfly-shaped body liner (1880) having first (1808) and second (1810) adhesive zones such as described with respect to FIG. 18A.

Fold Lines

When the body liners described here are folded along a longitudinal axis to place the body liner at least partially within the intergluteal cleft, it may be desirable to configure the body liner to promote folding along the longitudinal axis. In some variations, it may be desirable to increase the rigidity of the body liner along a longitudinal axis of the body liner. By increasing the rigidity of along the longitudinal axis, the body liner is more likely to fold along the longitudinal axis rather than across or at an angle to the longitudinal axis. Additionally, increasing the rigidity of the longitudinal axis of the may facilitate placement of the body liner within the intergluteal cleft. When a wearer uses one or more fingers to push the body liner within the intergluteal cleft, force applied to a portion of the longitudinal axis may be transmitted along the rigid longitudinal axis, which may help to push the longitudinal axis closer to the base of the intergluteal cleft.

Figure 16A:
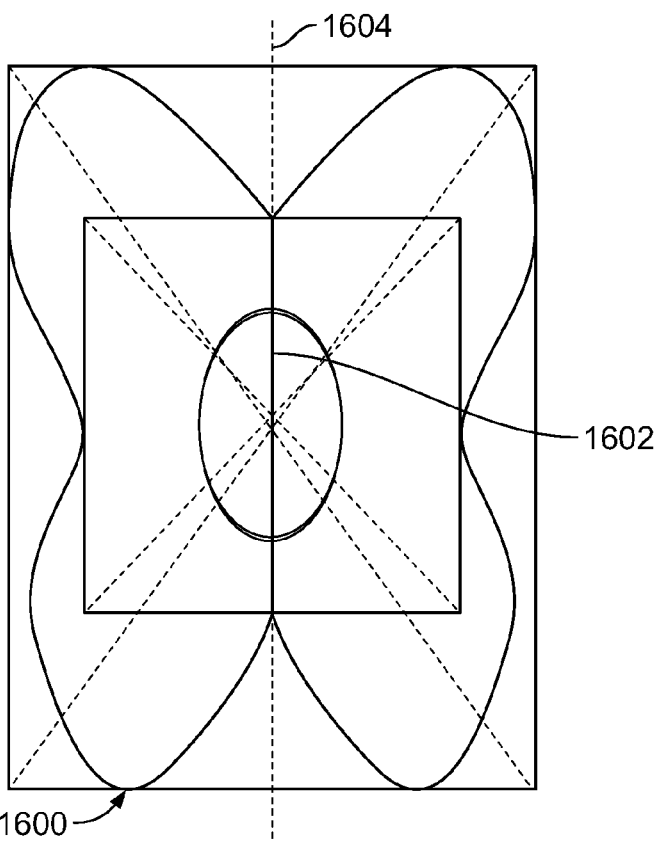
FIGS. 16A and 16B depict top views of variations of body liners comprising score lines.
Figure 16B:
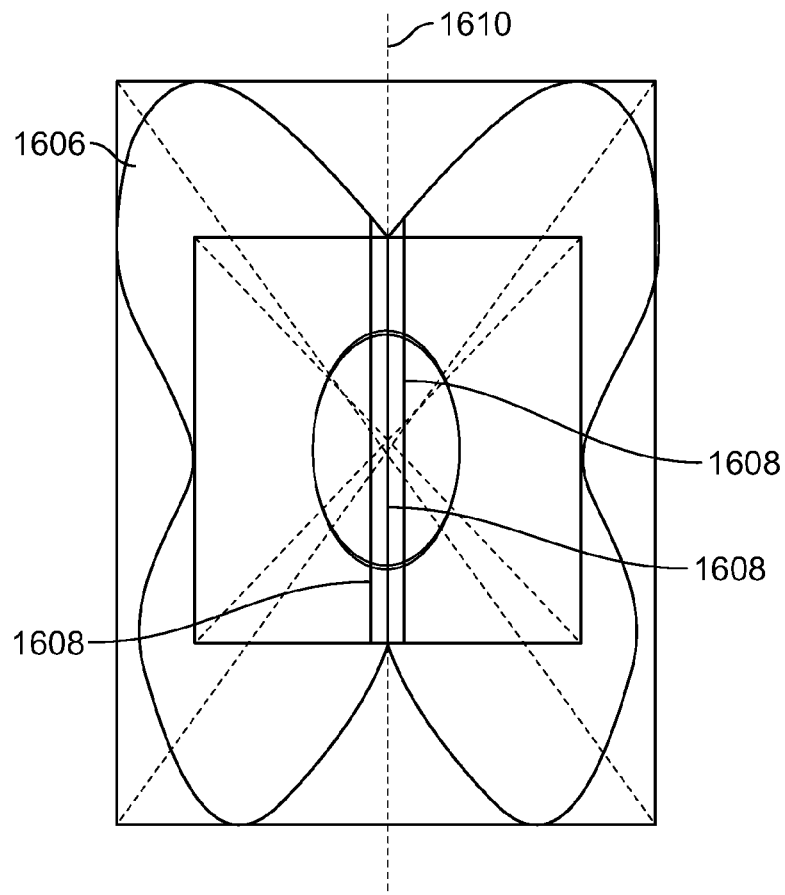

Preferential folding along the longitudinal axis may be achieved in any suitable manner. In some variations, the body liner may be scored or crushed along the longitudinal axis. For example, FIG. 16A shows a variation of a body liner (1600) having a score line (1602) along a longitudinal axis (1604) in which the material forming the body liner (1600) has been scored. In other variations, the score line (1602) may be replaced with a crush line along the longitudinal axis, in which the material forming the body liner is crushed or otherwise compressed along the longitudinal axis. In still other variations, a body liner may comprise both a crush line and a score line. While shown in FIG. 16A as having a single crush line (1602), the body liner (1600) may have any suitable number of score and/or crush lines (e.g., one, two, or three or more score or crush lines). For example, FIG. 16B shows another variation of body liner (1606) comprising three score lines (1608) along a longitudinal axis (1610) of the body liner (1606). In these variations, scoring and/or crushing on either side of the longitudinal axis may open up a portion of the body liner to face the anus when placed in the intergluteal cleft. In some instances it may be desirable to limit the width of scoring and/or crushing to the width of the anus, as a larger width may result in bunching of the body liner or discomfort.

Barrier Members

When the body liners described here are placed in the intergluteal cleft, and an anal leakage load contacts the body liner, gravity may have a tendency to pull the leakage in a downward direction. If the body liner is not able to immobilize the fluid quickly enough (e.g., via fluid absorption to dewater the leakage), the load of anal leakage may travel along the body liner toward the front of the liner, and may flow off the front of the liner, thereby creating a soiling issue. Accordingly, in some variations the body liners described here may be configured to have one or more features which may help to restrict, slow, or otherwise prevent flow of a leakage load toward the front of the body liner.

Figure 15A:
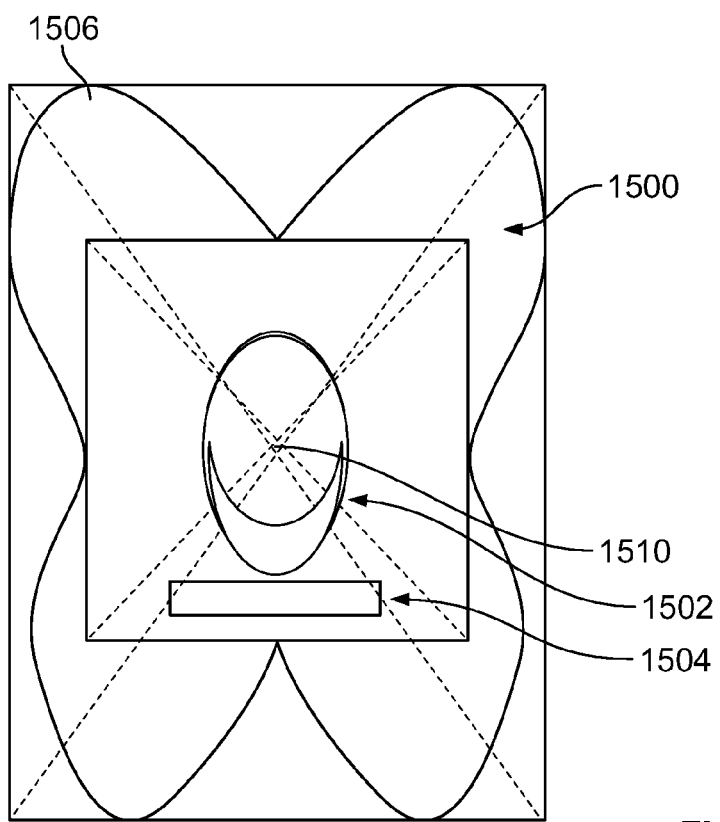
FIG. 15A shows a top view of a body liner comprising barrier elements.

For example, in some variations, the body liner may comprise a barrier element. For example, FIG. 15A shows a variation of a body liner (1500) comprising a first barrier element (1502) and a second barrier element (1504). It should be appreciated that although shown in FIG. 15A as having both a first barrier element (1502) and a second barrier element (1504), the body liners described here may comprise one barrier element (e.g., either barrier element (1502), barrier element (1504), or another suitable barrier element), or may comprise three or more barrier elements.

When the body liners described here include a barrier element, the barrier element may form a raised portion of the body liner, and typically extend away from a body-facing side of the body liner. The barrier element provide a barrier to fluid flow as fluid moves relative to the body liner (e.g., when gravity pulls fluid toward the front of the body liner), which may give the body liner more time to absorb the anal leakage. Additionally, in some variations, the barrier element may be formed from one or more fluid-absorbent materials, such as the materials described in more detail above. In these variations, when fluid contacts the barrier element, the barrier element may provide a physical barrier to fluid flow and may additionally absorb some or all of the fluid sample.

The barrier element may have any suitable size or shape. For example, in some variations, the barrier element may be shaped as a bar, a curved lip, or the like. For example, in the variation of body liner (1500) shown in FIG. 15A, the first barrier element (1502) may comprise a curved lip which may extend from a body-facing surface (1506) of the body liner (1500). In some variations, the width of the first barrier element (1502) may taper as the barrier element (1502) extends away from the body liner (1500). Also shown in FIG. 15A, the second barrier element (1504) may comprise a bar structure which may extend from the body-facing surface (1506). In some variations, the width of the second barrier element (1504) may taper as the barrier element (1504) extends away from the body liner (1500).

While the first (1502) and second (1504) barrier elements shown in FIG. 15A are shown as attached to the body-facing surface (1506) of the body liner (1500), it should be appreciated that a barrier element may be connected to a body liner in any suitable manner. For example, in variations where a body liner comprises two or more liner layers, one or more barrier elements may be positioned between two or more liner layers. For example, in variations where a body liner comprises a top sheet, a back sheet, and a core member positioned between the top sheet and the back sheet, a barrier may be positioned between the top sheet and the back sheet. In some instances, the barrier may also be positioned between the top sheet and the core member or may be positioned between the core member and the back sheet. In still other variations, the barrier element may be integrally formed with a liner layer of the body liner. In these variations, the thickness of the liner layer may be increased at a portion thereof to form a barrier element. Any suitable liner layer of a body liner (e.g., a top sheet, a back sheet, a core member, or the like) may be formed with a barrier element.

Figure 15B:
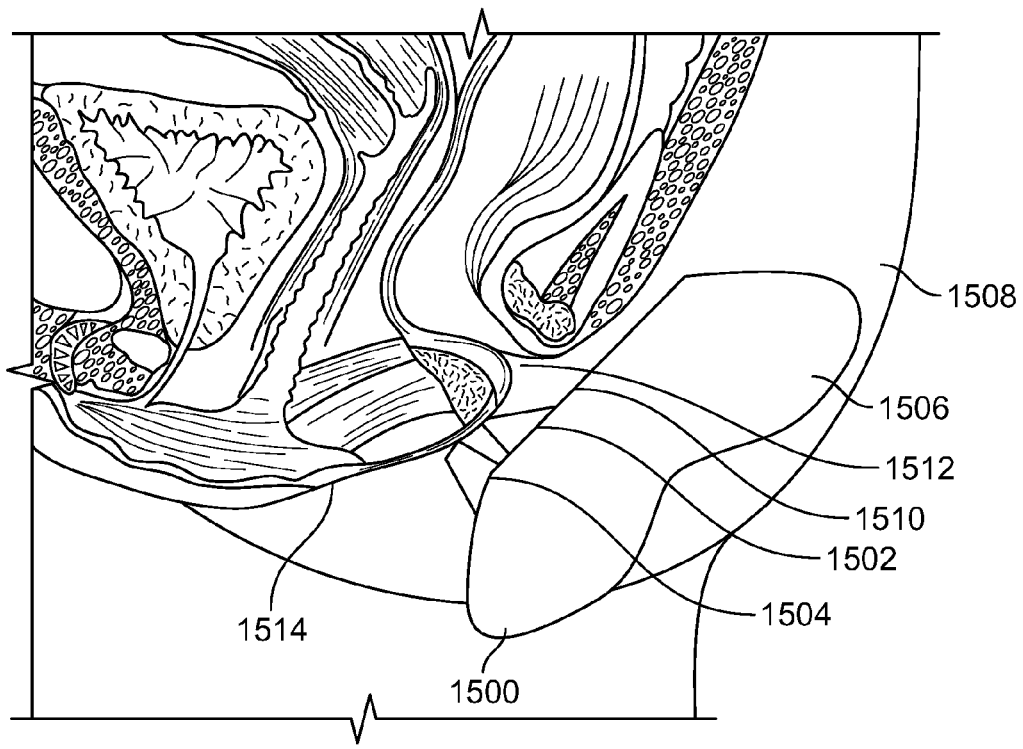
FIG. 15B shows the body liner of FIG. 15A positioned at least partially in the intergluteal cleft.

When a body liner comprises one or more barrier element such as described immediately above, the barrier elements may be positioned at any suitable location relative to the body liner. In some variations, one or more barrier elements may be positioned frontward of a target point on the body liner. In these variations, when the target point is positioned at or near the anus, such as described hereinthroughout, the one or more barrier elements may be positioned closer to the front of the body. In some instances, the barrier elements may contact or otherwise press against the skin of the wearer between the anus and the genitals (i.e., the scrotum or the vagina). This contact may provide tactile feedback to the wearer, which may provide the wearer with a sense of security, and may further provide an indication that the body liner is properly positioned. Positioning a barrier element frontward of the anus may help stop downward and frontward movement of anal leakage when the wearer is upright. For example, FIG. 15B shows the body liner (1500) described above with respect to FIG. 15A positioned at least partially in the intergluteal cleft (1508) to position a target point (1510) of the body liner (1500) at or near the anus (1512). Since the first (1502) and second (1504) barrier members are positioned forward of the target point (1510), the first (1502) and second (1504) barrier members may be positioned between the anus (1512) and the genitals (1514). In some variations, one or more barrier elements may positioned rearward of the target point. In these variations, when the target point is positioned at or near the anus, the one or more barrier elements positioned rearward of the target point may help stop rearward movement of fluid of anal leakage that may occur if the wearer is prone.

Placement Aids

In some variations, the body liner may be configured to assist a wearer in placing the body liner at least partially within the intergluteal cleft. For example, in some variations where a body liner comprises a top sheet, a back sheet, and a core member positioned therebetween, the body liner may be configured such that the contours of the core member may be visible through the top sheet and/or back sheet. For example, in some variations the top sheet and/or the back sheet may be configured such that the core member may be at least partially visualized therethrough, such that the core member may be visually located. In some variations, the core member may be colored, which may contribute to visual location of the core member. Additionally or alternatively, the thickness of the core member between the top sheet and back sheet may create variations in the thickness of the body liner which allow for visual location of the core member. When a wearer is placing a body liner with a visually-locatable core member, the wearer may place one or more fingers on the core member, and may advance the body liner member into the intergluteal cleft. If the wearer advances his or her fingers toward the anus, the wearer may center the core member around the anus to position a target point at or near the anus in a blind manner (e.g., does not require direct visualization of the body liner placement).

In some variations, the body liner may comprise one or more markings which may indicate a target point of the body liner. For example, in some variations a rear surface of the body liner may comprise an arrow pointing to toward a target point of the body liner. In other variations, the rear surface of the body liner may comprise cross-hairs, a bulls-eye, or another shape that may be centered on a target point of the body liner. In still other variations, one or more patterns may be embossed in the rear surface of the body liner which may indicate a target point on the body liner. In the above variations, the wearer may place one or more fingers on the target point (as indicated by the markings and/or embossed patterns), and may advance the body liner into the intergluteal cleft to position the target point at or near the anus.

In still other variations, the body liner may comprise one or more barrier members or one or more crimped zones, such as described in more detail above, one or more barrier members or crimped zones may be positioned to provide tactile feedback to the wearer to indicate proper placement of the body liner. For example, when the body liner is placed at least partially within the intergluteal cleft, one or more barrier members or crimped zones may contact the skin of the wearer between the anus and the genitals, and may feedback that the body liner is properly placed.

Substance Delivery

In some variations, the body liner may comprise one or more compounds or compositions. In some variations, the body liner may comprise one or more lotions or skin care compositions. Additionally or alternatively, the body liner may comprise one or more drugs are active agents (e.g., aloe, glycerin, a silicon oil such as polydimehtylsiloxane, combinations thereof and the like) which may be delivered to the skin of the wearer (e.g., via the skin-facing surface of the body liner). Additionally or alternatively, the body liner may comprise one or more anti-odor compounds which may minimize the odors associated with an incidence of ABL.

Packaging

The body liners described here may be packaged in any suitable manner. For example, in some variations, a body liner may be packaged in a pouch or container. In some instances, the body liners may be individually packaged (i.e., one body liner per pouch/container). In other variations, multiple body liners may be packaged together. For example, in some variations multiple body liners may be packaged within a resealable container, such that individual body liners may be removed as needed.

As mentioned above, the body liners described here may be packaged with a release liner. The release liner may be temporarily attached to a body liner via one or more adhesive regions of the body liner. The release liner may be the same shape as or may be a different shape from the body liner. The release liner may be configured as a single piece, or may be configured as two or more separate pieces.

In some variations, the body liners may be packaged without a release liner. In some of these variations, a portion of the packaging may act as a release liner. Specifically, in some variations a body liner having one or more adhesive regions may be releasably attached to one or more portions of the packaging via one or more of the adhesive regions. In these variations, the packaging may be opened to provide access to the body liner, and the body liner may be peeled or otherwise removed from the packaging to reveal the adhesive regions.

The body liners described here may be provided in a merchandising array. The array may comprise a sequence of body liner configurations for users having different physical characteristics. The physical characteristics may be any suitable characteristic, such as, for example, waist size, dress size, or underwear size. The array may comprise a first sequence of body liner configurations for female users. Additionally or alternatively, the array may comprise a second sequence of body liner configurations for male users. Each body liner configuration may have an indicia (pictorial and/or text based) disposed on the packaging to identify the intended user of that specific body liner configuration. Consumers may use the indicia to select an appropriate body liner configuration for their needs.

Generally, the sequence of body liner configurations comprises body liners having different sizes. As mentioned above, it may be desirable for the body liner to at least partially extend from the intergluteal cleft when the body liner is positioned therein. As such, as the size of a user's intergluteal cleft changes, the size of the body liner may be altered accordingly to provide for a retrieval portion of the body liner. Because the size of intergluteal cleft may be at least partially dependent on one or more physical characteristics of a user, such as the user's dress size, waste size, and/or underwear size, providing different sized body liners for users having different dress, waste, and/or underwear sizes may allow a user to select a body liner that will be properly sized for that user. For example, in some variations a sequence of body liner configurations may comprise a first body liner configuration for users having a first range of dress sizes and a second body liner configuration for users having a second range of dress sizes. For example, the first range of dress sizes may be dress size 12 or less and the second range of dress sizes may be dress size greater than 12, and the first body liner configuration may have a first size and a second body liner configuration may have a second size. In other variations, a sequence of body liner configurations may comprise a first body liner configuration for users having a first range of waist sizes and a second body liner configuration for users having a second range of waist sizes. In some of these variations, the array may comprise sequences of body liner configurations for both male and female users. For example, an array may have a first body liner configuration for male users having a first range of waist sizes and a second body liner configuration for male users having a second range of waist sizes, a third body liner configuration for female users having a third range of waist sizes, and a fourth body liner configuration for female users having a fourth range of waist sizes. In yet other variations, the array may comprise a sequence of body liners having a first body liner configuration for users having a first underwear size and a second body liner configuration for users having a second underwear size. The sequence may further comprise a third body liner configuration for users having a third underwear size.

Methods

As mentioned above, the body liners described here may be used to fecal incontinence. Generally, the methods described here may comprise placing one of the body liners described above at least partially in the intergluteal cleft. In some variations, placing a body liner at least partially in the intergluteal cleft may comprise folding the body liner along the longitudinal axis, and may comprise positioning a target point at or near the anus. In some of these variations, it may be desirable to place the target point within about 2 cm of the anus.

In some variations, placing the body liner at least partially within the intergluteal cleft may comprise positioning the body liner such that at least a portion of the body liner extends out of the intergluteal cleft. In some of these variations, at least a portion of the body liner that extends out of the intergluteal cleft may extend at least about 1 cm of the intergluteal cleft. In some variations, the body liner may be placed such that at least a portion of the body liner extends out of the intergluteal cleft, and such that any portion extending out of the intergluteal cleft extends out of the intergluteal cleft less than about 2.5 cm.

In some variations, placing the body liner at least partially within the intergluteal cleft may comprise placing a body-facing surface of the body liner in contact with the skin of the buttocks. In some of these variations, the body liner may comprise one or more adhesive regions on the body-facing surface of the body liner, and wherein placing the body-facing surface of the body liner in contact with the skin of the buttocks may comprise adhering the body-facing surface to skin of the buttocks via the one or more adhesive regions. The adhesive regions may be any suitable adhesive regions, such as described in more detail above.

What is claimed is:

1. A device for treating fecal incontinence comprising:
   a body liner sized and configured to be placed at least partially within the intergluteal cleft, the body liner having a longitudinal axis along which the body liner is folded when placed at least partially within the intergluteal cleft, a latitudinal axis perpendicular to the longitudinal axis and intersecting the longitudinal axis at a target point, a body-facing surface, and a rear surface opposite the body-facing surface, wherein the body-facing surface has a higher coefficient of friction than a coefficient of friction of the rear surface, wherein the body liner is formed from at least one liner layer, and every liner layer of the at least one liner layer is fluid absorbent, wherein the body liner has a butterfly shape comprising a body portion, and a first lobe, a second lobe, a third lobe, and a fourth lobe extending from the body portion, wherein the first and second lobes are positioned on a first side of the longitudinal axis and the third and fourth lobes are positioned on a second side of the longitudinal axis, and wherein heights of the first and third lobes along the longitudinal axis are at least 15% of a height of the body portion along the longitudinal axis.

2. The device of claim 1 wherein the first and third lobes are positioned on a first side of the latitudinal axis, and the second and fourth lobes are positioned on a second side of the latitudinal axis.

3. The device of claim 2 wherein the height of the first lobe along the longitudinal axis is greater than a height of the second lobe along the longitudinal axis.

4. The device of claim 2 wherein the height of the third lobe along the longitudinal axis is greater than a height of the fourth lobe along the longitudinal axis.

5. The device of claim 1 wherein the at least one liner layer comprises a top sheet and a core member.

6. The device of claim 5 wherein the core member has a circular or oval shape, and wherein the shape of the top sheet is the same as the shape of the body liner.

7. The device of claim 6 wherein the at least one liner layer further comprises a back sheet.

8. The device of claim 7 wherein the core member is positioned between the back sheet and the top sheet.

9. The device of claim 7 wherein the back sheet and the top sheet are at least partially bonded together.

10. The device of claim 9, wherein the back sheet and top sheet are bonded together around a periphery of the top sheet.

11. The device of claim 10, wherein the back sheet and top sheet are bonded together such that at least 80 percent of the top sheet remains unbonded.

12. The device of claim 1 wherein the body liner is configured to be flushable.

13. The device of claim 1 further comprising at least one adhesive region on the skin-facing surface.

14. The device of claim 13 further comprising a release liner removably attached to the body liner.

15. The device of claim 1 wherein the body liner is configured to move fluid within the body liner at a first wicking rate in a first direction, a second wicking rate in a second direction, and a third wicking rate in a third direction, wherein the first and second directions are within a plane of the body liner, the first direction is perpendicular to the second direction, and the third direction is perpendicular to the plane of the body liner.

16. The device of claim 15 wherein the body liner is configured such that the third wicking rate in the body liner is greater than the first and second wicking rates in the body liner.

17. The device of claim 15 wherein the body liner is configured such that the first wicking rate in the body liner is greater than the second wicking rate in the body liner.

* * * * *